United States Patent
Little et al.

(10) Patent No.: US 11,430,111 B2
(45) Date of Patent: *Aug. 30, 2022

(54) COMPUTER PROCESSES BEHIND AN ENHANCED VERSION OF AQUA

(71) Applicant: Novartis AG, Basel (CH)

(72) Inventors: Brian Little, Carlsbad, CA (US); Jennifer Bordeaux, Carlsbad, CA (US)

(73) Assignee: Novartis AG, Basel (CH)

( * ) Notice: Subject to any disclaimer, the term of this patent is extended or adjusted under 35 U.S.C. 154(b) by 239 days.

This patent is subject to a terminal disclaimer.

(21) Appl. No.: 16/823,291

(22) Filed: Mar. 18, 2020

(65) Prior Publication Data
US 2020/0286230 A1    Sep. 10, 2020

Related U.S. Application Data

(63) Continuation of application No. 15/769,731, filed as application No. PCT/US2016/058280 on Oct. 21, 2016, now Pat. No. 10,621,721.
(Continued)

(51) Int. Cl.
*G06T 7/00* (2017.01)
*G16B 15/00* (2019.01)
(Continued)

(52) U.S. Cl.
CPC ....... *G06T 7/0012* (2013.01); *G01N 21/6456* (2013.01); *G01N 33/574* (2013.01);
(Continued)

(58) Field of Classification Search
CPC ............. G06T 7/0012; G06T 7/10; G06T 2207/10064; G16B 15/00; G01N 21/6456;
(Continued)

(56) References Cited

U.S. PATENT DOCUMENTS

| 6,215,892 B1 | 4/2001 | Douglass et al. |
| 7,555,150 B2 | 6/2009 | Ikeda |

(Continued)

FOREIGN PATENT DOCUMENTS

| JP | 2004-532410 A | 10/2004 |
| JP | 2009-229274 A | 10/2009 |

(Continued)

OTHER PUBLICATIONS

Thresholding, Morse, 2000, http://homepages.inf.ed.ac.uk/rbf/CVonline/LOCAL_COPIES/MORSE/threshold.pdf (Year: 2000).*
(Continued)

*Primary Examiner* — Jianxun Yang
(74) *Attorney, Agent, or Firm* — Foley & Lardner LLP

(57) ABSTRACT

The invention relates, in part, to systems and methods for scoring a sample containing tumor tissue from a cancer patient. The score obtained from these methods can be indicative of a likelihood that a patient may respond positively to immunotherapy. The invention also relates, in part, to methods of deriving a value for % biomarker positivity (PBP) for all cells or optionally, one or more subsets thereof, present in a field of view of a tissue sample from a cancer patient. The values for PBP can be indicative of a patient's response to immunotherapy.

19 Claims, 42 Drawing Sheets

Related U.S. Application Data

(60) Provisional application No. 62/301,037, filed on Feb. 29, 2016, provisional application No. 62/259,328, filed on Nov. 24, 2015, provisional application No. 62/245,938, filed on Oct. 23, 2015.

(51) Int. Cl.

| | | |
|---|---|---|
| *G01N 33/574* | (2006.01) | |
| *G01N 21/64* | (2006.01) | |
| *G06T 7/155* | (2017.01) | |
| *G06T 7/62* | (2017.01) | |
| *G06T 7/60* | (2017.01) | |
| *G06V 20/69* | (2022.01) | |

(52) U.S. Cl.
CPC .............. *G06T 7/155* (2017.01); *G06T 7/60* (2013.01); *G06T 7/62* (2017.01); *G06V 20/698* (2022.01); *G16B 15/00* (2019.02); *G06T 2207/10056* (2013.01); *G06T 2207/10064* (2013.01); *G06T 2207/20036* (2013.01); *G06T 2207/30024* (2013.01); *G06T 2207/30096* (2013.01)

(58) Field of Classification Search
CPC ............. G01N 33/574; G01N 21/6458; G01N 33/57434; G01N 33/743; G01N 2333/723; G01N 2800/52; G01N 2800/7028; G01J 3/4406; C12Q 1/6886; C12Q 2600/118; C12Q 2600/156; Y02A 90/26; A61N 5/10; A61K 31/593; A61K 31/567
See application file for complete search history.

(56) References Cited

U.S. PATENT DOCUMENTS

| | | |
|---|---|---|
| 7,583,403 B2 | 9/2009 | Ito et al. |
| 8,571,353 B2 | 10/2013 | Watanabe |
| 2006/0013478 A1 | 1/2006 | Ito et al. |
| 2008/0046190 A1 | 2/2008 | Rimm et al. |
| 2012/0053447 A1 | 3/2012 | Duchesne |
| 2013/0177928 A1 | 7/2013 | Peterson et al. |
| 2013/0330325 A1 | 12/2013 | Grabe et al. |
| 2014/0003702 A1 | 1/2014 | McCulloch et al. |
| 2014/0055364 A1 | 2/2014 | Sze et al. |
| 2014/0275709 A1 | 9/2014 | Khorrami et al. |
| 2015/0086541 A1 | 3/2015 | Aguilar-Cordova |
| 2016/0035100 A1* | 2/2016 | Bamford .................. G06T 7/10 382/131 |
| 2016/0146819 A1* | 5/2016 | Ince ..................... A61K 31/567 514/167 |
| 2016/0266126 A1* | 9/2016 | Shipitsin ................ G06T 7/136 |

FOREIGN PATENT DOCUMENTS

| | | |
|---|---|---|
| JP | 2012-021904 A | 2/2012 |
| WO | WO 2004/032524 A1 | 2/2006 |
| WO | WO 2015/088930 A1 | 6/2015 |
| WO | WO 2015/124777 A1 | 8/2015 |

OTHER PUBLICATIONS

International Search Report and Written Opinion issued in related International Patent Application No. PCT/US2016/058280, dated Feb. 8, 2017.
Thresholding, Morse, 2000, http://homepages.inf.ed.ac.uk/rbf/CVonline/LOCAL_COPIES/MORSE/threshold.pdf (2000).
Johnson, et al., "Quantitative Spatial Profiling of PD-1/PD-L1 Interaction and HLA-DR/IDO-1 Predicts Improved Outcomes of Anti-PD-1 Therapies in Metastatic Melanoma," *Clinical Cancer Research*, vol. 24, No. 21, pp. 5250-5260 (2018).
Kluger, et al., "Characterization of PD-L1 Expression and Associated T-cell Infiltrates in Metastatic Melanoma Samples from Variable Anatomic Sites," *Clinical Cancer Research*, vol. 21, pp. 3052-3060 (2015).
Wimberly, et al., PD-L1 Expression Correlates with Tumor-Infiltrating Lymphocytes and Response to Neoadjuvant Chemotherapy in Breast Cancer, Cancer Immunology Research, vol. 3, No. 4, pp. 326-332 (2015).
Office Action issued in co-pending Japanese Patent Application No. 2018-521296, dated Sep. 1, 2020.
Examination Report issued in Australia Patent Application No. 2016341306, dated Oct. 18, 2021.

\* cited by examiner

COMPUTER PROCESSES BEHIND AN ENHANCED VERSION OF AQUA

CROSS-REFERENCE TO RELATED APPLICATIONS

This application is a continuation of U.S. patent application Ser. No. 15/769,731, filed Apr. 19, 2018, which is the U.S. National Stage of International Patent Application No. PCT/US2016/058280, filed Oct. 21, 2016, which claims priority from U.S. Provisional Patent Application No. 62/245,938, filed Oct. 23, 2015, U.S. Provisional Patent Application No. 62/259,328, filed Nov. 24, 2015, and U.S. Provisional Patent Application No. 62/301,037, filed Feb. 29, 2016, all of which are hereby incorporated by reference in their entirety.

BACKGROUND

The present invention relates generally to the field of cancer treatment.

SUMMARY OF THE INVENTION

Disclosed herein, in one aspect, are imaging systems comprising an image processing controller comprising a processing circuit configured to execute instructions stored on a computer-readable medium which cause the controller of the image processing system to: configured to receive image data from an imaging device, the image data describing a sample of tumor tissue taken from a cancer patient; and determine, using the image data, a score representative of a nearness between at least one pair of cells in the tumor tissue, a first member of the at least one pair of cells expressing a first biomarker and a second member of the at least one pair of cells expressing a second biomarker that is different from the first biomarker; wherein the score is indicative of a likelihood that the cancer patient will respond positively to immunotherapy. In some embodiments, the score representative of a nearness between at least one pair cells is representative of an extent that the pair of cells are within a predetermined proximity of one another. In some embodiments, the nearness is assessed on a pixel scale. In some embodiments, the predetermined proximity between the pair of cells ranges from about 1 pixel to about 100 pixels. In some embodiments, the predetermined proximity between the pair of cells ranges from about 5 pixel to about 40 pixels. In some embodiments, the predetermined proximity between the pair of cells ranges from about 0.5 µm to about 50 µm. In some embodiments, the predetermined proximity between the pair of cells ranges from about 2.5 µm to about 20 µm. In some embodiments, the score is determined by obtaining a proximity between the boundaries of the pair of cells. In some embodiments, the score is determined by obtaining a proximity between the centers of mass of the pair of cells. In some embodiments, the score is determined using boundary logic based on a perimeter around a selected first cell of the pair of cells. In some embodiments, the score is determined by determining an intersection in the boundaries of the pair of cells. In some embodiments, the score is determined by determining an area of overlap of the pair of cells. In some embodiments, the image processing controller is further configured to separate the image data into unmixed image data; and provide the data through a plurality of data channels, in which the unmixed image data in a first data channel describes fluorescence signals attributable to the first biomarker and the unmixed image data in a second data channel describes fluorescence signals attributable to the second biomarker. In some embodiments, to determine the score, the image processing controller is configured to dilate fluorescence signals attributable to the first biomarker from the first data channel by a predetermined margin that is selected to encompass proximally located cells expressing the second biomarker to generate a dilated first biomarker mask; determine an interaction area, wherein the interaction area is a first total area for all cells which express the second biomarker and are encompassed within the dilated fluorescence signals attributable to the cells expressing the first biomarker; and divide the interaction area by a normalization factor, and multiplying the resulting quotient by a predetermined factor to arrive at a spatial proximity score. In some embodiments, the normalization factor is a total area for all cells that have a capacity to express the second biomarker. In some embodiments, the interaction area is determined by combining the dilated first biomarker mask with a mask representative of cells that express the second biomarker, determined from signals of the second data channel. In some embodiments, a third data channel describes fluorescence signals attributable to cell nuclei and a fourth data channel describes fluorescence signals attributable to tumor area in the sample. In some embodiments, the total area for all cells that have a capacity to express the second biomarker is determined by combining a cell mask representative of all cells in the sample, based on signals from the third data channel, and a tumor area mask representative of the tumor area on the sample, based on signals from the fourth data channel. In some embodiments, combining the cell mask and the tumor area mask comprises removing the tumor area mask from the cell mask. In some embodiments, each mask is generated by assigning a binary value to each pixel of image data from a selected channel. In some embodiments, the binary value is assigned to each value by a threshold function, wherein the threshold function assigns a value of 1 to each pixel that has an intensity equal to or greater than a predetermined intensity threshold, and assigns a value of 0 to each pixel that has an intensity below the predetermined intensity threshold. In some embodiments, the binary value is assigned to each value by a histogram threshold function, wherein the histogram threshold function uses a sliding scale of pixel intensity to determine a threshold, and assigns a value of 1 to each pixel that has an intensity equal to or greater than an intensity threshold, and assigns a value of 0 to each pixel that has an intensity below the intensity threshold. In some embodiments, the threshold is determined by summing an intensity of every pixel into a total intensity; multiplying a threshold percentage by the total intensity to obtain a cut-off sum; grouping all pixels by intensity in a histogram; and summing the pixel intensities from lowest to highest until the cut-off sum is achieved; wherein the last highest pixel intensity visited in the process is the intensity threshold. In some embodiments, combining the masks is performed using an "and" operation: wherein the "and" operation is a multiplication of the pixel intensity of a pixel in a first mask by the pixel intensity of the pixel in a second mask. In some embodiments, combining the masks is performed using an "out" operation; wherein the "out" operation removes the a second mask from a first mask. In some embodiments, the image processing controller is further configured to obtain image data at a low magnification representative of the concentration of the first or the second biomarker in the image; identify areas that include the highest concentration of the first or the second biomarker; select a predetermined number of the areas including the highest concentration of the first or the second biomarker; send instructions to imaging device to obtain high magnification image data for the predetermined number of areas; and wherein the high magnification image data is provided to the controller to be analyzed and used to determine the score. In some embodiments, the low magnification is less than or equal to 10× magnification and wherein the high magnification is greater than 10×. In some embodiments, the low magnification is 10× magnification and wherein the high magnification is 40×. In some embodiments, the low magnification is 10× magnification and wherein the high magnification is 20×. In some embodiments, the low magnification is 4× magnification and wherein the high magnification is 40×. In some embodiments, the low magnification is 4× magnification and wherein the high magnification is 20×. In some embodiments, the image processing unit is further configured to associate the score with metadata associated with the images of the sample. In some embodiments, the image processing unit generates a report including the score. In some embodiments, the image processing unit is further configured to provide the score to an operator to determine immunotherapy strategy. In some embodiments, the image processing unit is further configured to record the score in a database. In some embodiments, the image processing unit is further configured to associate the score with a patient's medical record. In some embodiments, the image processing unit is further configured to display the score on a display device. In some embodiments, the first member of the at least one pair of cells comprises a tumor cell and the second member of the at least one pair of cells comprises a non-tumor cell. In some embodiments, the non-tumor cell comprises an immune cell. In some embodiments, the first and second members of the at least one pair of cells comprise immune cells. In some embodiments, the first member of the at least one pair of cells comprises a tumor cell, a myeloid cell, or a stromal cell and the second member of the at least one pair of cells comprises an immune cell. In some embodiments, the tumor cell, myeloid cell, or stromal cell expresses PD-L1 and the immune cell expresses PD-1. In some embodiments, the image processing unit is further configured to select a predetermined number of fields of view available from the sample comprising tumor tissue taken from the cancer patient and determine the score from data associated with each field of view. In some embodiments, the sample is stained with a plurality of fluorescence tags, and wherein each of the fluorescence tags is directed to a specific biomarker. In some embodiments, the plurality of fluorescence tags comprises a first fluorescence tag for the first biomarker and a second fluorescence tag for the second biomarker. In some embodiments, the margin ranges from about 1 to about 100 pixels. In some embodiments, the proximally located cells expressing the second biomarker are within about 0.5 to about 50 µm of a plasma membrane of the cells that express the first biomarker. In some embodiments, the predetermined factor is $10^4$. In some embodiments, the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof. In some embodiments, the threshold value ranges from about 500 to about 5000. In some embodiments, the threshold value is about 900 plus or minus 100. In some embodiments, the immunotherapy comprises immune checkpoint therapy. In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are systems for determining a score representative of a proximity between at least one pair of cells in a tumor tissue sample, the system comprising a memory, the memory comprising a spectral unmixer receiving image data from an imaging device, separating the image data into unmixed image data, and providing the data through a plurality of data channels, in which the unmixed image data in a first data channel describes fluorescence signals attributable to a cell nucleus, the unmixed data in a second data channel describes fluorescence signals attributable to tumor tissue, the unmixed data in a third data channel describes fluorescence signals attributable to a first biomarker, and the unmixed image data in a fourth data channel describes fluorescence signals attributable to a second biomarker: a cell masker using image data from the first data channel and generating an image representative of all nuclei in a field of view and dilating the image to generate a cell mask; a tumor area masker using image data from the second data channel and generating a mask of all tumor area in the field of view; a first biomarker masker using image data from the third data channel and generating a first biomarker mask of all cells in the field of view that express the first biomarker: a second biomarker masker using image data from the fourth data channel and generating a second biomarker mask of all cells in the field of view that express the second biomarker; a tumor masker combining the cell mask and the tumor area mask to generate at least one of a non-tumor cell mask and a tumor cell mask: a dilator dilating the first biomarker mask to generate a dilated first biomarker mask: an interaction masker for combining the dilated first biomarker mask and the second biomarker mask to generate an interaction mask; an interaction calculator calculating a spatial proximity score. In some embodiments, the interaction calculator divides the area of the interaction mask by the area of one of the non-tumor cell mask, the tumor cell mask, and the cell mask. In some embodiments, the spatial proximity score is calculated according to the equation:

$$SPS = \frac{A_I}{A_C} \times 10^4$$

wherein $A_I$ is a total interaction area (area of the interaction mask) and $A_C$ is the total area of the at least one of the non-tumor cell mask, the tumor cell mask, and the cell mask. In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are methods of processing an image of a tissue sample to determine a score representative of a proximity between at least one pair of cells in the tissue, the method comprising: receiving image data associated with a tissue sample comprising tumor tissue taken from a cancer patient; selecting at least one field of view from the sample comprising tumor tissue taken from the cancer patient, which is stained with a plurality of fluorescence tags, which selection is biased toward selecting at least one field of view that contains a greater number of cells that express the first biomarker relative to other fields of view; dilating, for each of the selected fields of view, fluorescence signals attributable to the first biomarker by a margin sufficient to encompass proximally located cells expressing the second biomarker; dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score; and recording the score, which score when compared to a threshold value is indicative of a likelihood that the cancer patient will respond positively to immunotherapy. In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are systems for determining a value of biomarker positivity in a tissue sample, the system comprising a processing circuit comprising a memory, the memory comprising a spectral unmixer receiving image data from an imaging device, separating the image data into unmixed image data, and providing the data through a plurality of data channels, in which the unmixed image data in a first data channel describes fluorescence signals attributable to a cell nucleus, the unmixed data in a second data channel describes fluorescence signals attributable to a subset tissue of interest, and the unmixed data in a third data channel describes fluorescence signals attributable to a first biomarker: a cell masker using image data from the first data channel and generating an image representative of all nuclei in a field of view and dilating the image to generate a cell mask; a subset area masker using image data from the second data channel and generating a mask of all subset area in the field of view; a first biomarker masker using image data from the third data channel and generating a first biomarker mask of all cells in the field of view that express the first biomarker; a subset masker combining the cell mask and the subset area mask to generate at least one of a non-subset cell mask and a subset cell mask; an combination masker for combining the biomarker mask and at least one of the non-subset cell mask and the subset cell mask: a positivity calculator for calculating a biomarker positivity value. In some embodiments, the calculator divides an area of the biomarker mask by an area of the at least one of the non-subset cell mask and the subset cell mask. In some embodiments, the subset tissue of interest is tumor tissue, the subset cell is a tumor cell, and the non-subset cell is a non-tumor cell.

In some embodiments, the first biomarker comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB. OX40, CTLA-4, CD40L, CD28, GITR, ICOS, CD28, CD3, CD4, CD8, FoxP3, CD25, CD16, CD56, CD68, CD163, CD80, and CD86.

In some embodiments, the second biomarker is different from the first biomarker and comprises a biomarker selected from PD-L. PD-L2. B7-H3, B7-H4, HLA-DR. Galectin 9. CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4. CD8, FoxP3, CD25, CD16, CD56, CD68, CD163, CD80, and CD86

In another aspect, disclosed herein are systems comprising an image processing unit configured to receive image data from an imaging device, the image data describing a sample of tissue taken from a patient; and determine a biomarker positivity value representative of an amount of cells of a type in the sample expressing a biomarker of interest relative to the total amount of cells of the type in the sample.

Disclosed herein, in one aspect, are imaging systems for scoring a sample comprising tumor tissue taken from a cancer patient, the imaging system comprising an imaging device comprising a stage for positioning the sample in an imaging field, an electromagnetic radiation source for directing electromagnetic radiation at the sample, and a detector configured to detect electromagnetic radiation from the sample, and a controller. The controller comprises a user interface for exchanging information between an operator and the controller; and a processing circuit configured to execute instructions stored on a computer-readable medium. The instructions are configured to cause the controller to: (i) receive information about the detected electromagnetic radiation from the imaging device; (ii) generate image data based on the detected electromagnetic radiation; (iii) analyze the image data to determine a score representative of a nearness between at least one pair of cells, a first member of the least one pair of cells expressing a first biomarker and a second member of the at least one pair of cells expressing a second biomarker that is different from the first biomarker; and (iv) record the score, which score when compared to a threshold value is indicative of a likelihood that the cancer patient will respond positively to immunotherapy.

In some embodiments, the score is representative of a nearness between at least one pair cells is representative of an extent that the pair of cells are within a predetermined proximity of one another. In some embodiments, the nearness is assessed on a pixel scale. In some embodiments, the predetermined proximity between the pair of cells ranges from about 1 pixel to about 100 pixels. In some embodiments, the predetermined proximity between the pair of cells ranges from about 5 pixel to about 40 pixels. In some embodiments, the predetermined proximity between the pair of cells ranges from about 0.5 μm to about 50 μm. In some embodiments, the predetermined proximity between the pair of cells ranges from about 2.5 μm to about 20 μm.

In some embodiments, the score is calculated by obtaining a proximity between the boundaries of the pair of cells. In some embodiments, the score is calculated by obtaining a proximity between the centers of mass of the pair of cells. In some embodiments, the score is calculated using boundary logic based on a perimeter around a selected first cell of the pair of cells. In some embodiments, the score is calculated by determining an intersection in the boundaries of the pair of cells. In some embodiments, the score is calculated by determining an area of overlap of the pair of cells.

In some embodiments, generating the image data comprises: (i) separating the information about the detected electromagnetic radiation into unmixed image data; and (ii) providing the data through a plurality of data channels, in which the unmixed image data in a first data channel describes fluorescence signals attributable to the first biomarker and the unmixed image data in a second data channel describes fluorescence signals attributable to the second biomarker.

In some embodiments, analyzing the data comprises: (i) dilating, using a dilator of the processing circuit, fluorescence signals attributable to the first biomarker from the first data channel by a predetermined margin that is selected to encompass proximally located cells expressing the second biomarker to generate a dilated first biomarker mask; (ii) determining an interaction area, wherein the interaction area is a first total area for all cells which express the second biomarker and are encompassed within the dilated fluorescence signals attributable to the cells expressing the first biomarker; and (iii) dividing, using an interaction calculator of the processing circuit, the interaction area by a normalization factor, and multiplying the resulting quotient by a predetermined factor to arrive at a spatial proximity score.

In some embodiments, the normalization factor is a total area for all cells that have a capacity to express the second biomarker. In some embodiments, the interaction area is determined by combining the dilated first biomarker mask with a mask representative of cells that express the second biomarker, determined from signals of the second data channel. In some embodiments, a third data channel describes fluorescence signals attributable to cell nuclei and a fourth data channel describes fluorescence signals attributable to tumor area in the sample. In some embodiments, the total area for all cells that have a capacity to express the second biomarker is determined by combining a cell mask representative of all cells in the sample, based on signals from the third data channel, and a tumor area mask representative of the tumor area on the sample, based on signals from the fourth data channel. In some embodiments, combining cell mask and the tumor area mask comprises removing the tumor area mask from the cell mask.

In some embodiments, the processing circuit is further configured to cause the controller to: (i) obtain image data at a low magnification representative of the concentration of the first or the second biomarker in the image; (ii) identify areas that include the highest concentration of the first or the second biomarker; (iii) select a predetermined number of the areas including the highest concentration of the first or the second biomarker; (iv) send instructions to imaging device to obtain high magnification image data for the predetermined number of areas; wherein the high magnification image data is provided to the controller to be analyzed and used to determine the score.

In some embodiments, the low magnification is less than or equal to 10× magnification and wherein the high magnification is greater than 10×. In some embodiments, the low magnification is 10× magnification and wherein the high magnification is 40×. In some embodiments, the low magnification is 10× magnification and wherein the high magnification is 20×. In some embodiments, the low magnification is 4× magnification and wherein the high magnification is 40×. In some embodiments, the low magnification is 4× magnification and wherein the high magnification is 20×.

In some embodiments, the controller associates the score with metadata associated with the images of the sample. In some embodiments, the controller generates a report including the score. In some embodiments, the controller provides the score to an operator to determine immunotherapy strategy. In some embodiments, the controller records the score in a database. In some embodiments, the controller associates the score with a patient's medical record.

In some embodiments, the electromagnetic radiation source is an incoherent electromagnetic radiation source selected from the group consisting of an incandescent lamp, a fluorescent lamp, or a diode. In some embodiments, the electromagnetic radiation source is a coherent electromagnetic radiation source. In some embodiments, the system further comprises electromagnetic radiation conditioning optics positioned to direct electromagnetic radiation from the electromagnetic radiation source to the sample. In some embodiments, the electromagnetic radiation conditioning optics include an adjustable spectral filter element configured to provide for illumination of the sample using different electromagnetic radiation wavelength bands.

In some embodiments, the system further comprises electromagnetic radiation collecting optics configured to receive emitted electromagnetic radiation from the sample and direct the emitted electromagnetic radiation as output electromagnetic radiation to the detector. In some embodiments, the electromagnetic radiation collecting optics include an adjustable spectral filter element configured to select particular electromagnetic radiation wavelength bands from the electromagnetic radiation from the sample.

In some embodiments, the detector comprises at least one CCD sensor. In some embodiments, the detector comprises a photomultiplier tube. In some embodiments, the detector is configured to generate an electrical signal corresponding to the electromagnetic radiation from the sample and communicate the electrical signal to the controller.

In some embodiments, the controller is further configured to send electrical signals to one or more of the stage, the electromagnetic radiation source, and the detector to adjust at least one property of the stage, the electromagnetic radiation source and/or the detector. In some embodiments, the system further comprises a display device for displaying information to the operator. In some embodiments, the displayed information is one of parameters of the system, properties of the system, and captured images of the sample. In some embodiments, the controller displays the score on the display device.

In some embodiments, the information about the detected electromagnetic radiation from the imaging device is a plurality of spectral images. In some embodiments, the plurality of spectral images each correspond to a different wavelength of electromagnetic radiation emitted by the sample and detected by the detector. In some embodiments, each wavelength of electromagnetic radiation emitted by the sample corresponds to a different fluorophore added to the sample to identify specific features in the sample.

In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are methods of scoring a tissue sample comprising: (i) using an imaging system to obtain image data for the tissue sample taken from a cancer patient. The imaging system comprises a housing comprising a stage for positioning the sample in an imaging field, an electromagnetic radiation source for directing electromagnetic radiation at the sample, and a detector for collecting electromagnetic radiation output; and a controller comprising memory and an processing circuit having image processing modules. (ii) Analyzing, using the image processing modules, the image data to determine a score representative of a nearness between a pair of cells, a first member of the pair of cells expressing a first biomarker and a second member of the pair of cells expressing a second biomarker that is different from the first biomarker; and (iii) recording the score in the memory, which score when compared to a threshold value is indicative of a likelihood that the cancer patient will respond positively to immunotherapy.

In some embodiments, the score is representative of the nearness between the pair of cells is representative of an extent that the pair of cells are within a predetermined proximity of one another. In some embodiments, analyzing the image date comprises assessing the nearness on a pixel scale. In some embodiments, the predetermined proximity between the pair of cells ranges from about 1 pixel to about 100 pixels. In some embodiments, the predetermined proximity between the pair of cells ranges from about 5 pixel to about 40 pixels. In some embodiments, the predetermined proximity between the pair of cells ranges from about 0.5 µm to about 50 µm. In some embodiments, the predetermined proximity between the pair of cells ranges from about 2.5 µm to about 20 µm. In some embodiments, the score is calculated by obtaining a proximity between the boundaries of the pair of cells. In some embodiments, the score is calculated by obtaining a proximity between the centers of mass of the pair of cells. In some embodiments, the score is calculated using boundary logic based on a perimeter around a selected first cell of the pair of cells. In some embodiments, the score is calculated by determining an intersection in the boundaries of the pair of cells. In some embodiments, the score is calculated by determining an area of overlap of the pair of cells.

In some embodiments, generating the image data comprises: (i) separating the information about the detected electromagnetic radiation into unmixed image data; and (ii) providing the data through a plurality of data channels, in which the unmixed image data in a first data channel describes fluorescence signals attributable to the first biomarker and the unmixed image data in a second data channel describes fluorescence signals attributable to the second biomarker.

In some embodiments, analyzing the image data comprises: (i) dilating, using a dilator of the processing circuit, fluorescence signals attributable to the first biomarker from the first data channel by a predetermined margin that is selected to encompass proximally located cells expressing the second biomarker to generate a dilated first biomarker mask; (ii) determining an interaction area, wherein the interaction area is a first total area for all cells which express the second biomarker and are encompassed within the dilated fluorescence signals attributable to the cells expressing the first biomarker; and (iii) dividing, using an interaction calculator of the processing circuit, the interaction area by a normalization factor, and multiplying the resulting quotient by a predetermined factor to arrive at a spatial proximity score.

In some embodiments, the normalization factor is a total area for all cells that have a capacity to express the second biomarker. In some embodiments, determining the interaction area comprises combining the dilated first biomarker mask with a mask representative of cells that express the second biomarker, determined from signals of the second data channel. In some embodiments, a third data channel describes fluorescence signals attributable to cell nuclei and a fourth data channel describes fluorescence signals attributable to tumor area in the sample.

In some embodiments, the method further comprises determining the total area for all cells that have a capacity to express the second biomarker by combining a cell mask representative of all cells in the sample, based on signals from the third data channel, and a tumor area mask representative of the tumor area on the sample, based on signals from the fourth data channel. In some embodiments, combining the cell mask and the tumor area mask comprises removing the tumor area mask from the cell mask.

In some embodiments, the methods further comprise (i) using the imaging system to image data at a low magnification representative of the concentration of the first or the second biomarker in the image; (ii) identifying areas that include the highest concentration of the first or the second biomarker; (iii) selecting a predetermined number of the areas including the highest concentration of the first or the second biomarker; (iv) sending instructions to imaging device to obtain high magnification image data for the predetermined number of areas; and (iv) wherein the high magnification image data is provided to the controller to be analyzed and used to determine the score.

In some embodiments, the low magnification is less than or equal to 10× magnification and wherein the high magnification is greater than 10×. In some embodiments, the low magnification is 4× magnification and wherein the high magnification is 20×.

In some embodiments, the methods further comprise associating the score with metadata associated with the images of the sample. In some embodiments, the methods further comprise generating a report including the score. In some embodiments, the methods further comprise providing the score to a professional to determine immunotherapy strategy. In some embodiments, the methods further comprise recording the score in a database. In some embodiments, the methods further comprise associating the score with a patient's medical record. In some embodiments, the methods further comprise displaying the score on a display device.

In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

In another aspect, disclosed herein are tissue sample scoring systems comprising: (i) an imaging device that obtains image data of a tissue sample taken from a cancer patient; and (ii) a controller that receives image data from the imaging device and analyzes the data to determine a score representative of a nearness between a pair of cells, a first member of the at least one pair of cells expressing a first biomarker and a second member of the at least one pair of cells expressing a second biomarker that is different from the first biomarker; (iii) wherein the score, when compared to a threshold value is indicative of a likelihood that the cancer patient will respond positively to immunotherapy.

In some embodiments, the imaging device comprises a stage for positioning the sample in an imaging field, an electromagnetic radiation source for directing electromagnetic radiation at the sample, and a detector configured to detect electromagnetic radiation from the sample.

In some embodiments, the electromagnetic radiation is selected from the group consisting of visible and non-visible light. In some embodiments, the visible light comprises bands of visible light having wavelengths falling in the range of about 380 nm to about 720 nm. In some embodiments, the visible light comprises bands of visible light having wavelengths falling in the range of about 400 nm to about 700 nm. In some embodiments, the visible light comprises bands of visible light having wavelengths falling in the range of about 380 nm to about 720 nm.

In some embodiments, the emitted or output electromagnetic radiation comprises one or more bands of visible light from the group consisting of bands including wavelengths falling in the range of about 440 nm to about 480 nm, about 490 nm to about 550 nm, about 505 nm to about 535 nm, about 550 nm to about 595 nm, about 585 nm to about 630 nm, about 600 nm to about 640 nm, and about 650 nm to about 710 nm. In some embodiments, the electromagnetic radiation is selected from the group consisting of visible and non-visible light. In some embodiments, the visible light comprises bands of visible light having wavelengths falling in the range of about 380 nm to about 720 nm. In some embodiments, the visible light comprises bands of visible light having wavelengths falling in the range of about 400 nm to about 700 nm. In some embodiments, the visible light comprises bands of visible light having wavelengths falling in the range of about 380 nm to about 720 nm.

In some embodiments, the method provides a superior predictive power compared to quantitation of expression of the first biomarker or quantitation of expression of the second biomarker. In some embodiments, the predictive power is quantified as a positive predictive value, a negative predictive value, or a combination thereof. In some embodiments, the positive predictive value is 65% or greater. In some embodiments, the positive predictive value is 70% or greater. In some embodiments, the positive predictive value is 75% or greater. In some embodiments, the negative predictive value is 65% or greater. In some embodiments, the negative predictive value is 80% or greater.

BRIEF DESCRIPTION OF THE DRAWINGS

FIG. 7b shows a non-limiting example of a dilated binary mask of all cells within FIG. 7a.

FIG. 8b shows a non-limiting example of a binary mask of all tumor area within FIG. 8a.

FIG. 8c shows a non-limiting example of a mask of all tumor cells within FIG. 8a.

FIG. 8d shows a non-limiting example of a mask of all non-tumor cells within FIG. 8a.

FIG. 9b shows a non-limiting example of a binary mask of all PD-L1-positive cells within FIG. 9a.

FIG. 9c shows a non-limiting example of a mask of all PD-L1-positive tumor cells within FIG. 9a.

FIG. 9d shows a non-limiting example of a mask of all PD-L1-positive non-tumor cells within FIG. 9a.

FIG. 10b shows a non-limiting example of a binary mask of all PD-1-positive non-tumor cells within FIG. 10a.

FIG. 12b shows a non-limiting example of the maximum interaction scores from the 26 patients of FIG. 12a.

FIG. 20b shows a comparison of interaction scores with progression free survival of the patients of FIG. 20a.

FIG. 20c shows the interaction scores from the patients of FIGS. 12a and 12b and the patients of FIG. 20a.

FIG. 29b shows a non-limiting example of a dilated binary mask of all cells within FIG. 29a.

FIG. 30b shows a non-limiting example of a binary mask of all PD-1-positive cells within FIG. 30a.

FIG. 31b shows a non-limiting example of a binary mask of all CD3-positive cells within FIG. 31a.

DETAILED DESCRIPTION

Figure 1:
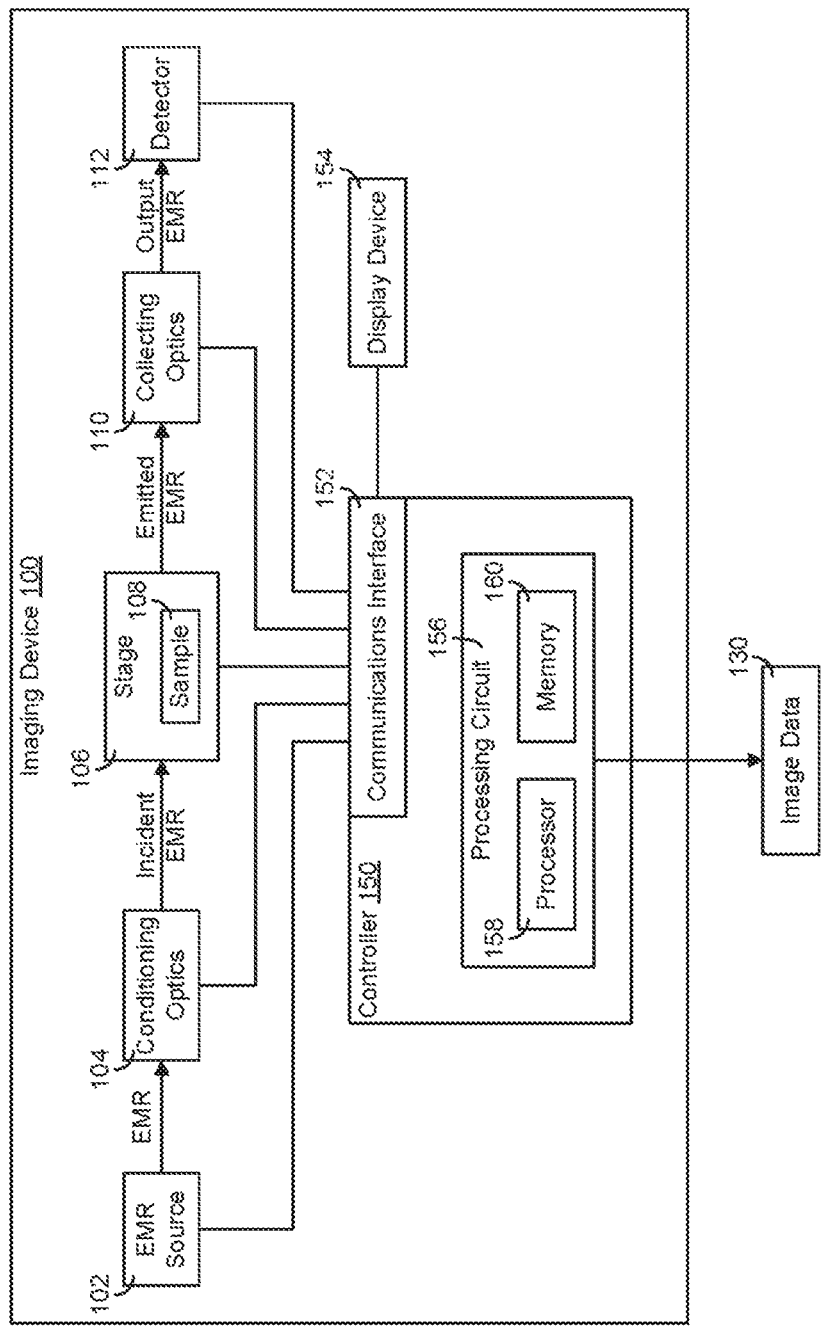
FIG. 1 is a block diagram of an imaging device for obtaining image data of a sample.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will van to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

In one aspect, provided herein are systems and methods for performing methods of scoring a sample comprising tumor tissue taken from a cancer patient. In another aspect, provided herein are systems and methods for deriving a percent biomarker positivity of a sample of tissue.

In methods disclosed herein, the cancer patient is a mammal. In some embodiments, the mammal is human. In some embodiments, the mammal is not human. In further embodiments, the mammal is mouse, rat, guinea pig, dog, cat, or horse.

In methods disclosed herein, tumor tissue is taken from a cancer patient. The type of cancer includes, but is not limited to, cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma: gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma): liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors: nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs: hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx: skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites, or a combination of one or more thereof.

Examples of immunotherapy include, but are not limited to, monoclonal antibodies (e.g., alemtuzumab or trastuzumab), conjugated monoclonal antibodies (e.g., ibritumomab tiuxetan, brentuximab vendotin, or ado-trastuzumab emtansine), bispecific monoclonal antibodies (blinatumomab), immune checkpoint inhibitors (e.g., ipilimumab, pembrolizumab, nivolumab, atezolizumab, or durvalumab), thalidomide, lenalidomide, pomalidomide, and imiquimod, and combinations thereof. In some embodiments, the immunotherapy comprises immune checkpoint therapy.

Figure 45:
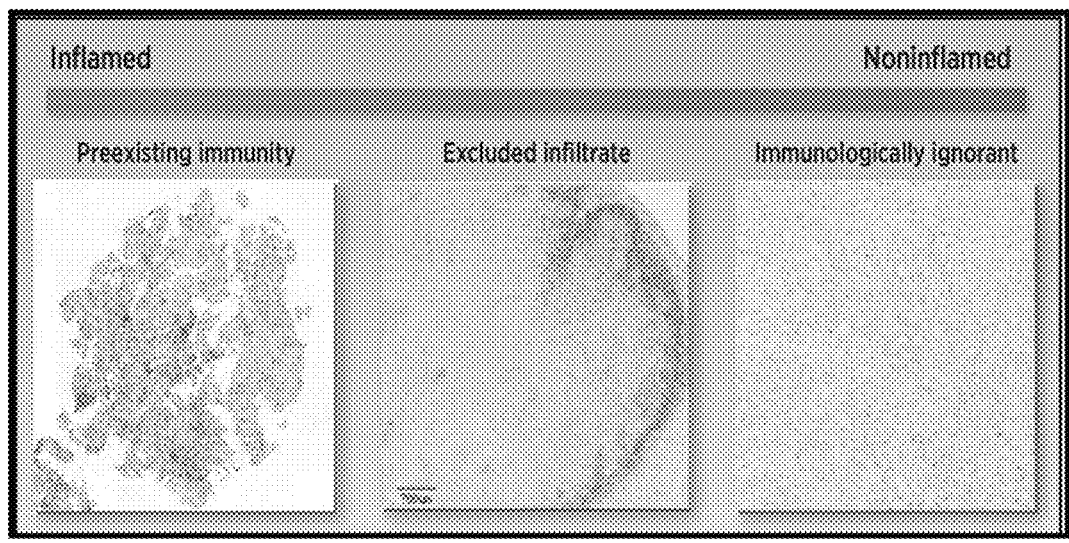
FIG. 45 shows representative tumor classification based on their immune contexture.

Tumors may be classified based on their immune contexture as "hot" (inflamed) or "cold" (non-inflamed) (see FIG. 45). While patients bearing hot tumors may be expected to respond to certain immunotherapies and potentially live longer than patients bearing cold tumors, it has been previously unclear to those skilled in the art as to which biomarkers correlate with response and survival.

To address this issue, some embodiments of the methods described herein aid in the identification of cancer patients who respond to one or more immunotherapies via expression of immune exhaustion biomarkers (e.g., PD-1 and PD-L1) and cancer patients who do not respond (i.e., non-responders) via the presence of cell types known to cause immune suppression (e.g., CD11b, HLA-DR, IDO-1, ARG1) or highly proliferating tumor cells devoid of MHC class I expression (e.g., Ki67+, B2M−). In some embodiments, the methods described herein comprise use of multiplex immunohistochemistry assays (e.g., multiplex FIHC assays) based on specific immune suppression or activation signatures. Non-limiting examples of multiplex FIHC assays based on specific immune suppression or activation signatures are shown in the following table.

| Objective | Multiplex FIHC Assay |
|---|---|
| T Cell Suppression | CD3 + PD-1 + PD-L1 |
| | Tumor marker (CK or S100) + PD-1 + PD-L1 |
| | CD3 + LAG3 + TIM3 |
| | CD3 + CD25 + FOXP3 |
| | CTLA-4 + CD80 |
| Myeloid Suppression | CD11b + HLA-DR(−) IDO-1 (TAM) |
| | CD11b + HLA-DR (+) ARG1 (fMDSC) |
| T Cell Activation | CD3 + CD8 + Ki67 |
| | CD3 + CD8 + Granzyme B |
| Immune cell Enumeration | CD3 + CD4 + CD8 |
| | Tumor marker (CK or S100) + CD 16 + CD56 |
| | Tumor marker (CK or S100) + CD68 + CD163 |
| Identification of cold tumors | Tumor marker (CK or S100) + CD3 (−) B2M (−) Ki67 (−) |

FIG. 1 is a schematic diagram showing an imaging device 100 for acquiring multiple spectrally resolved images of a sample. An electromagnetic radiation (EMR) source 102 provides electromagnetic radiation to conditioning optics 104. In some embodiments, the electromagnetic radiation is visible light. EMR source 102 can be an incoherent light source such as an incandescent lamp, a fluorescent lamp, or a diode. EMR source 102 can also be a coherent source such as a laser source, and the coherent source can provide continuous wave (CW) or pulsed light. EMR source 102 may contain multiple light source elements for producing light having a range of wavelengths (e.g., multiple diodes). The light can be either continuous-wave (CW) or time-gated (i.e., pulsed) light. Further, light can be provided in a selected portion of the electromagnetic spectrum. For example, light can have a central wavelength and/or a distribution of wavelengths that falls within the ultraviolet, visible, infrared, or other regions of the spectrum. In some embodiments, the light has wavelengths falling in the range of about 380 nm to about 720 nm. EMR source 102 can also include various optical elements such as lenses, mirrors, waveplates, and nonlinear crystals, all of which can be used to produce light having selected characteristics. In general, EMR source 102 includes optical elements and devices configured to provide light having desired spectral, spatial, and, in some embodiments, temporal properties.

Conditioning optics 104 can be configured to transform the electromagnetic radiation, such as visible light, in a number of ways. For example, conditioning optics 104 can spectrally filter light to provide output light in a selected wavelength region of the spectrum. Alternatively, or in addition, conditioning optics can adjust the spatial distribution of light and the temporal properties of the light. Incident electromagnetic radiation, or incident light, is generated by the action of the elements of conditioning optics 104 on the EMR.

Incident light is directed to be incident on sample 108 mounted on illumination stage 106. Stage 106 can provide means to secure sample 108, such as mounting clips or other fastening devices. Alternatively, stage 106 can include a movable track or belt on which a plurality of samples 108 are affixed. A driver mechanism can be configured to move the track in order to successively translate the plurality of samples, one at a time, through an illumination region on stage 106, whereon incident light impinges on the sample. Stage 106 can further include translation axes and mechanisms for translating sample 108 relative to a fixed position of illumination stage 106. The translation mechanisms can be manually operated (e.g., threaded rods) or can be automatically movable via electrical actuation (e.g., motorized drivers, piezoelectric actuators).

In response to incident electromagnetic radiation, such as visible light, emitted electromagnetic radiation emerges from sample 108. Emitted light can be generated in a number of ways. For example, in some embodiments, emitted light corresponds to a portion of incident light transmitted through sample 108. In other embodiments, emitted light corresponds to a portion of incident light reflected from sample. In yet further embodiments, incident light can be absorbed by sample 108, and the emitted light corresponds to fluorescence emission from sample 108 in response to incident light. In still further embodiments, sample 108 can be luminescent, and may produce emitted light even in the absence of incident light. In some embodiments, emitted light can include light produced via two or more of the foregoing mechanisms.

Collecting optics 110 are positioned to received emitted electromagnetic radiation, such as emitted light, from sample 108. Collecting optics 110 can be configured to collimate emitted light when light is divergent, for example. Collecting optics 110 can also be configured to spectrally filter emitted light. Filtering operations can be useful, for example, in order to isolate a portion of emitted light arising via one of the mechanisms discussed above from light arising via other processes. Further, collecting optics 110 can be configured to modify the spatial and/or temporal properties of emitted light for particular purposes in embodiments. Light collecting optics 110 transform emitted light into output light which is incident on detector 112.

Conditioning optics 104 and collecting optics 110 can include a variety of optical elements for manipulating the properties of light incident on, and emitted from, a sample of interest. For example, conditioning optics 104 and collecting optics 110 can each include spectral filter elements for selecting particular wavelength bands from incident and emitted light. The spectral filter elements can include, for example, interference filters mounted on a filter. In some embodiments, adjustable filter elements based on liquid crystal masks can be used to change the spectral properties of the incident or emitted light. Liquid crystal based devices can be controlled by controller 150 via communications interface 152.

Conditioning optics 104 and collecting optics 110 can also include elements such as spatial light masks, spatial light modulators, and optical pulse shapers in order to manipulate the spatial distribution of light incident on, or emitted from, a sample. Spatial light modulators and other adaptive devices can also be controlled via communications interface 152 by controller 150.

Finally, conditioning optics 104 and collecting optics 110 can include other common optical elements such as mirrors, lenses, beamsplitters, waveplates, and the like, configured in order to impart selected characteristics to the incident or emitted light.

In general, detector 112 includes one or more measurement devices configured to detect and capture light emitted by a sample as multiple images of the sample. In embodiments, detector 112 can be configured to measure the spatial and/or temporal and/or spectral properties of light. Detector 112 can include devices such as CCD arrays and photomultiplier tubes, along with their respective control systems, for acquiring the images. Detector 112 generates an electrical signal that corresponds to output light, and is communicated to controller 150. The adaptive optical devices in detector 112 can, in general, be controlled by controller 150 via communications interface 152.

Controller 150 includes a communications interface 152 and a processing circuit 156. In addition to receiving signals corresponding to output light detected by detector 112, controller 150 sends electrical signals to detector 112 to adjust various properties of detector 112, through communications interface 152. For example, if detector 112 includes a CCD sensor, controller 150 can send electrical signals to detector 112 to control the exposure time, active area, gain settings, and other properties of the CCD sensor.

Controller 150 also communicates with EMR source 102, conditioning optics 104, stage 106, and collecting optics 110 via communications interface 152. Control system 114 provides electrical signals to each of these elements of system 100 to adjust various properties of the elements. For example, electrical signals provided to light source 102 can be used to adjust the intensity, wavelength, repetition rate, or other properties of light 122. When the light produced by EMR source 102 is pulsed (i.e., time-gated), various properties of the light pulses can be manipulated according to control signals provided to EMR source 102 from controller 150 via communications interface 152. Signals provided to light conditioning optics 104 and light collecting optics 110 can include signals for configuring properties of devices that adjust the spatial properties of light (e.g., spatial light modulators) and for configuring spectral filtering devices, for example. Signals provided to illumination stage 106 can provide for positioning of sample 108 relative to stage 106 and/or for moving samples into position for illumination on stage 106, for example.

Communications interface 152 may include wired or wireless interfaces (e.g., jacks, antennas, transmitters, receivers, transceivers, wire terminals, etc.) for conducting data communications with various systems, devices, or networks. For example, communications interface 152 may include an Ethernet card and port for sending and receiving data via an Ethernet-based communications network and/or a WiFi transceiver for communicating via a wireless communications network. Communications interface 152 may be configured to communicate via local area networks or wide area networks (e.g., the Internet, a building WAN, etc.) and may use a variety of communications protocols (e.g., BACnet, IP, LON, etc.).

Controller 150 may also communicate, via communications interface 152, with a user interface 154. The user interface 154 may be a display device for displaying system properties and parameters, and for displaying captured images of sample 108. User interface 154 is provided in order to facilitate operator interaction with, and control over, imaging device 100. Processing circuit 156 includes a storage device, such as memory 160, for storing image data captured using detector 112, and also includes computer software that embodies instructions to processor 158 that cause processor 158 to carry out control functions, such as those discussed above and further below, for example. Further, the software instructions cause processor 158 to mathematically manipulate the images captured by detector 112. The processing and calculation of the images are described in greater detail herein, performed either by the processor 116 of the imaging device 100 or an external computing system associated with the imaging device 100, such as controller 200 depicted in FIG. 2 and described below.

In many embodiments, system 100 is configured to acquire multiple spectral images of sample 108. The multiple spectral images may correspond to illumination of sample 108 at a variety of selected wavelengths of light, and detecting an intensity of light either transmitted through or reflected by sample 108. Alternatively, the multiple spectral images may correspond to illumination of sample 108 with light having similar spectral properties, and collecting multiple images of sample 108, each image corresponding to a different wavelength of emitted light. Spectral filtering elements in conditioning optics 104 and collecting optics 110 are generally used to obtain the spectrally resolved data.

In some embodiments, images of sample 108 can be collected in sequence, with adjustments to the configuration of optical components (e.g., optical filters) between successive captured images. In other embodiments, multiple images can be captured simultaneously using detection systems configured to detect multiple sample views. For example, detection systems can be configured to project different views of the sample corresponding to different illumination or emission wavelengths onto a detector such as a CCD camera, and the multiple views can be captured simultaneously.

In some embodiments, conditioning optics 104 include an adjustable spectral filter element such as a filter wheel or a liquid crystal spectral filter. The filter element can be configured to provide for illumination of sample 108 using different light wavelength bands. EMR source 102 can provide light having a broad distribution of spectral wavelength components. A selected region of this broad wavelength distribution is allowed to pass as incident light by the filter element in conditioning optics 104, and directed to be incident on sample 108. An image of light transmitted through sample 108 is recorded by detector 112. Subsequently, the wavelength of the filter pass-band in conditioning optics 104 is changed to provide incident light having a different wavelength, and an image of light transmitted through sample 108 (and corresponding to the new wavelength of incident light) is recorded. A similar set of spectrally-resolved images can also be recorded by employing an EMR source 102 having multiple source elements generating light of different wavelengths, and alternately turning the different source elements on and off to provide incident light having different wavelengths.

As discussed previously, the emitted light from sample 108 can also correspond to incident light that is reflected from sample 108. Further, emitted light can correspond to fluorescence emission from sample 108 if the sample includes fluorescent chemical structures. For some samples, emitted light can include contributions from multiple sources (i.e., transmission and fluorescence) and the spectral filtering elements in light conditioning optics 110 can be used to separate these signal contributions.

In general, both conditioning optics 104 and collecting optics 110 include configurable spectral filter elements. Therefore, spectral resolution can be provided either on the excitation side of sample 108 (e.g., via conditioning optics 104) or on the emission side of sample 108 (e.g., via collecting optics 110), or both. In any case, the result of collecting multiple, spectrally resolved images of sample 108 is an "image stack" where each image in the stack is a two-dimensional image of the sample corresponding to a particular wavelength. Conceptually, the set of images can be visualized as forming a three-dimensional matrix, where two of the matrix dimensions are the spatial length and width of each of the images, and the third matrix dimension is the spectral wavelength (emission or excitation) to which the image corresponds. For this reason, the set of spectrally resolved images can be referred to as a "spectral cube" of images. As used herein, a "pixel" in such a set of images (or image stack or spectral cube), refers to a common spatial location for each of the images. Accordingly, a pixel in a set of images includes a value associated with each image at the spatial location corresponding to the pixel.

Other arrangements to obtain spectral images which are known in the art may be employed, according to the requirements of the sample at hand.

While each spectral image described above typically refers to a particular wavelength or range of wavelengths (e.g., a spectral band), more generally, each spectral image can correspond to a spectral index that may include one or more wavelength bands, or some more complex spectral distribution. For example, such an image can be generated by using a spectral comb filter. Generally, the image cube will include several spectral images, for example, 10 or more. However, in some embodiments, the image cube may include fewer images, for example, only two or three spectral images. One such example is an red-green-blue (RGB) color image, in which each pixel includes a value associated with the strength of each of the red, green, and blue colors. Such information may be displayed as a single color image, rather than as a set of separate images: however, the information content is the same as that in the set of images, and therefore we use the expression "spectral images" to refer to both cases.

Imaging device 100X) can include a wide variety of optical elements and devices for capturing images and generating image data 130 of a sample that is used in subsequent sample analysis algorithms, such as methods and algorithms for scoring a sample comprising tumor tissue taken from a cancer patient, described herein. Such imaging devices are described in U.S. Pat. No. 7,555,150 entitled "Classifying Image Features," which is hereby incorporated by reference in its entirety.

Prior to imaging a sample, the tissue sample may be stained using a plurality of fluorescence tags with affinity for specific biomarkers. A digital image of the stained sample may be obtained, and the image further analyzed based on the location of the fluorescence tags. Rather than whole-image analysis, processing circuit 156 of imaging device 100 may include software for causing the controller 150 to perform a field of view selection. Therein, fields of view may be prioritized based on the number of cells that express a first biomarker of interest. A predetermined number of fields of view may then be further analyzed for fluorescence signals. In some embodiments, the use of four different types of fluorescence tags generates an image of fluorescence signals corresponding to a first biomarker of interest and an image of fluorescence signals corresponding a second biomarker of interest, as well as to an image of fluorescence signals corresponding to a biomarker expressed by all cells and an image of fluorescence signals corresponding a biomarker expressed by tumor cells.

Examples of fluorophores include, but are not limited to, fluorescein, 6-FAM, rhodamine, Texas Red. California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®R, Cy3.5®, Cy5®, Cy5.5®, Cy7®, Cy-Chrome, DyLight® 350, DyLight® 405, DyLight® 488, DyLight®® 549, DyLight®, 594, DyLight® 633, DyLight® 649, DyLight® 680, DyLight® 750, DyLight® 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 630/650, BODIPY® 650/665, BODIPY® R6G, BODIPY® TMR, BODIPY® TR, OPAL™ 520, OPAL™ 540, OPAL™ 570, OPAL™ 620, OPAL™ 650, OPAL™ 690, and combinations thereof. In some embodiments, the fluorophore is selected from the group consisting of DAPI, Cy® 2, Cy® 3, Cy® 3.5, Cy® 5, Cy® 7, FITC, TRITC, a 488 dye, a 555 dye, a 594 dye, Texas Red. and Coumarin. Examples of a 488 dye include, but are not limited to, Alexa Fluor® 488, OPAL™ 520, DyLight® 488, and CF™ 488A. Examples of a 555 dye include, but are not limited to, Alexa Fluor® 555. Examples of a 594 dye include, but are not limited to, Alexa Fluor® 594.

As used herein, a "field of view" refers to a section of a whole-slide digital image of a tissue sample. In some embodiments, the whole-slide image has 2-200 predetermined fields of view. In some embodiments, the whole-slide image has 10-200 predetermined fields of view. In some embodiments, the whole-slide image has 30-200 predetermined fields of view. In some embodiments, the whole-slide image has 10-150 predetermined fields of view. In some embodiments, the whole-slide image has 10-100 predetermined fields of view. In some embodiments, the whole-slide image has 10-50 predetermined fields of view. In some embodiments, the whole-slide image has 10-40 predetermined fields of view. In some embodiments, the whole-slide image has 10, 15, 20, 25, 30, 35, 40, 45, 50, 55, 60, 65, 70, 75, 80, 85, 90, 95, or 100, including increments therein, predetermined fields of view.

Figure 2:
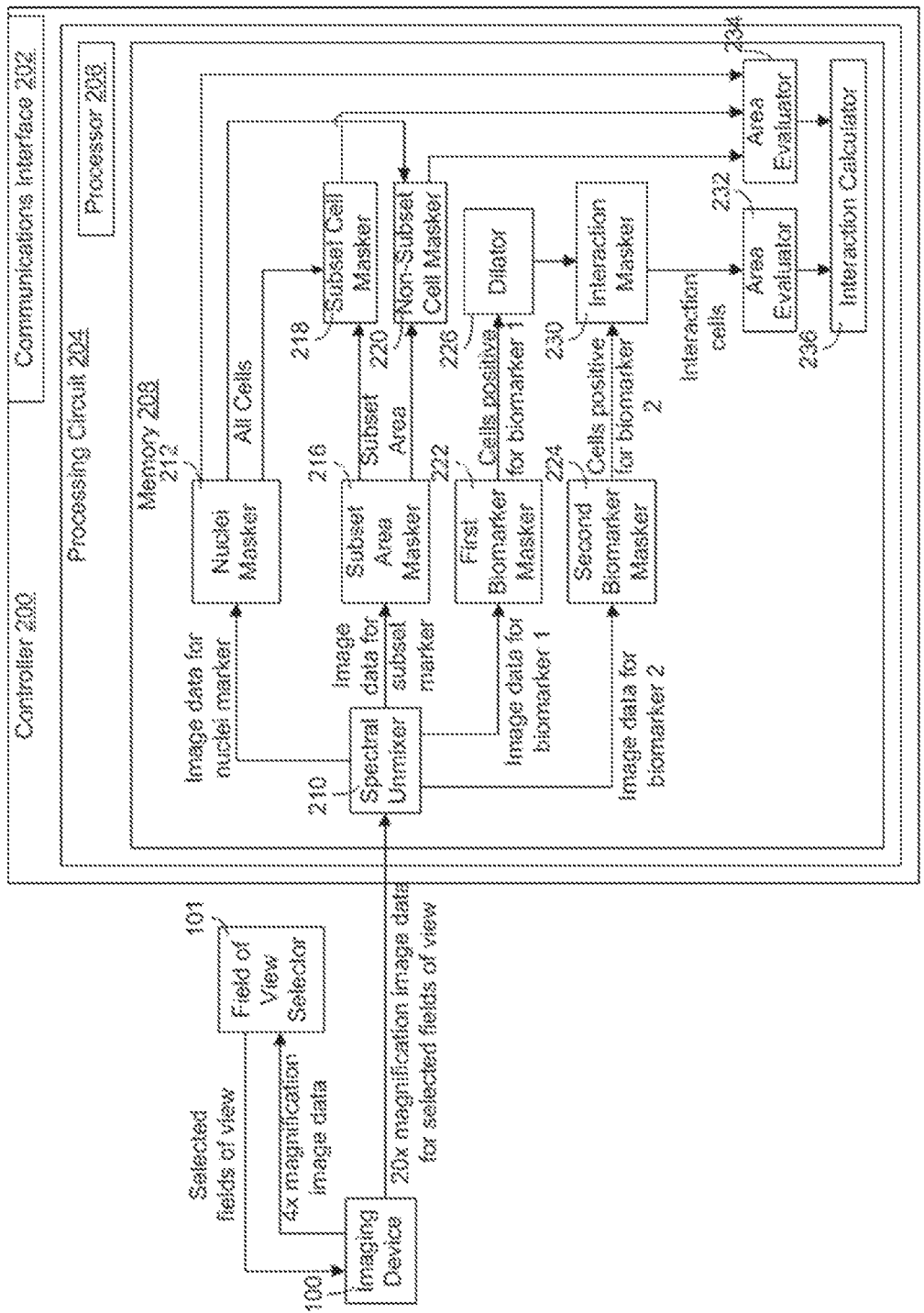
FIG. 2 is a block diagram of a controller configured to score a sample comprising tumor tissue taken from a cancer patient, according to an exemplary embodiment.

Manipulation of the image data from imaging device 100, for scoring the tissue sample, as described herein, may be carried out by controller 200, shown schematically in FIG. 2. Controller 200 is shown to include a communications interface 202 and a processing circuit 204. The processing circuit 204 is configured to implement steps for scoring the tissue sample. It is contemplated that the elements and functions of controller 200 may be included in controller 150 of imaging device 100, or may be present in a computing system separate from imaging device 100.

In some embodiments, the images of fluorescence signals are manipulated to generate one or more masks of fluorescence signals corresponding to cells within the image. In some embodiments, the one or more masks of fluorescence signals comprise one or more selected from the group consisting of a mask of all cells within the image, a mask of all cells that express the subset biomarker (e.g., all tumor cells), within the image, a mask of all cells that do not express the subset biomarker (e.g., all non-tumor cells) within the image, a mask of all cells expressing a first biomarker of interest within the image, a mask of all cells expressing a second biomarker of interest within the image, and an interaction mask representing all cells expressing a first biomarker of interest within the image as well as proximally located cells expressing a second biomarker of interest. In still further embodiments, the interaction mask is used to generate an interaction compartment of the cells from all selected fields of view expressing the second biomarker of interest that were proximally located to the cells expressing the first biomarker of interest. The total area of the interaction compartment may be used to generate a score representative of a spatial proximity between at least one pair of cells, a first member of the at least one pair of cells expressing the first biomarker and a second member of the at least one pair of cells expressing the second biomarker that is different from the first biomarker. In some embodiments, the score indicates the likelihood that the cancer patient will respond positively to immunotherapy. In some embodiments, the system provides a superior predictive power compared to a quantitation of expression of the first biomarker of interest or a quantitation of expression of the second biomarker of interest.

Figure 3:
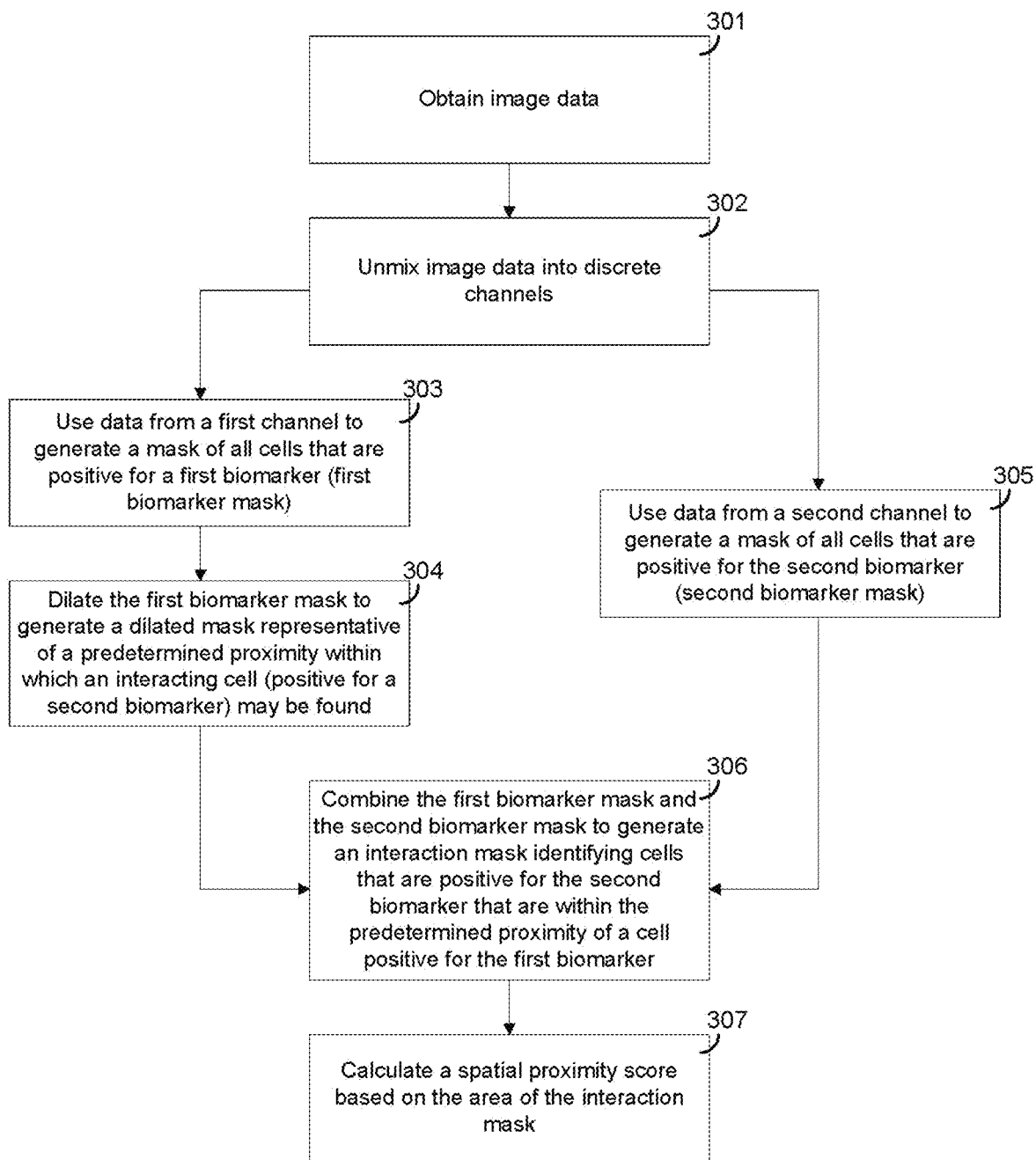
FIG. 3 is a flowchart of a process for scoring a sample comprising tumor tissue, according to an exemplary embodiment.

FIG. 3 is a flowchart depicting the steps of one embodiment of a method for scoring a sample comprising tumor tissue taken from a cancer patient. In step 301, image data, such as image data 130, is obtained. Image data may be obtained by an imaging device, such as imaging device 100. In step 302, the image data is unmixed such that data specific to various types of fluorescence signals are separated into different channels. In step 303, data from a first channel is used to generate a mask of all cells that are positive for a first biomarker (first biomarker mask). The mask of all cells is then dilated (step 304) to generate a dilated mask representative of a predetermined proximity within which an interacting cell (positive for a second biomarker) may be found. In some embodiments, the first biomarker mask is dilated between 1 and 100 pixels. In step 305, data from a second channel is used to generate a mask of all cells that are positive for the second biomarker (second biomarker mask). In step 306, the first biomarker mask and the second biomarker mask are combined to generate an interaction mask identifying cells that are positive for the second biomarker that are within the predetermined proximity of a cell positive for the first biomarker. In step 307, a spatial proximity score is calculated based on the area of the interaction mask.

Figure 4:
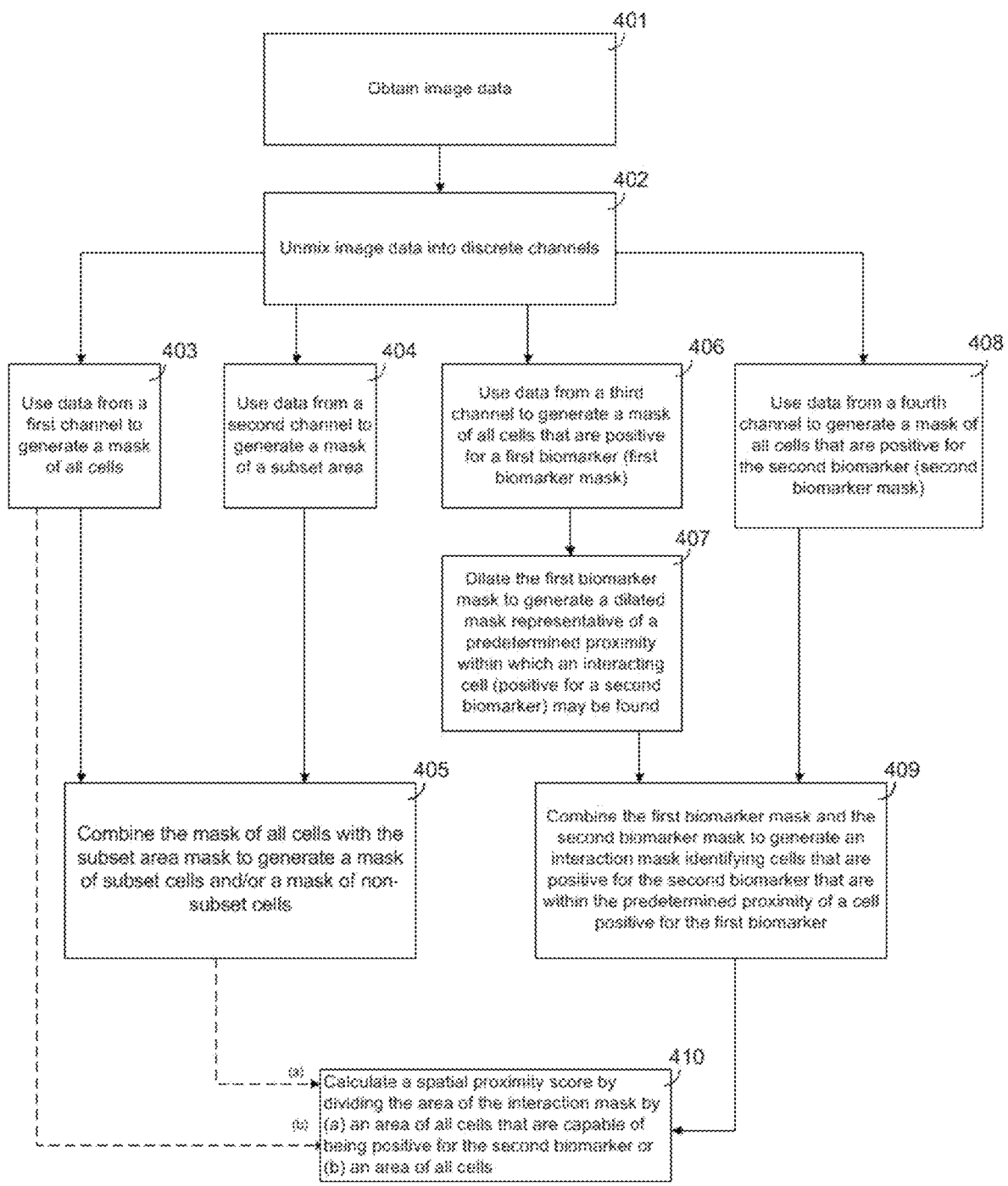
FIG. 4 is a flowchart of a process for scoring a sample comprising tumor tissue, according to a second exemplary embodiment.
Figure 15:
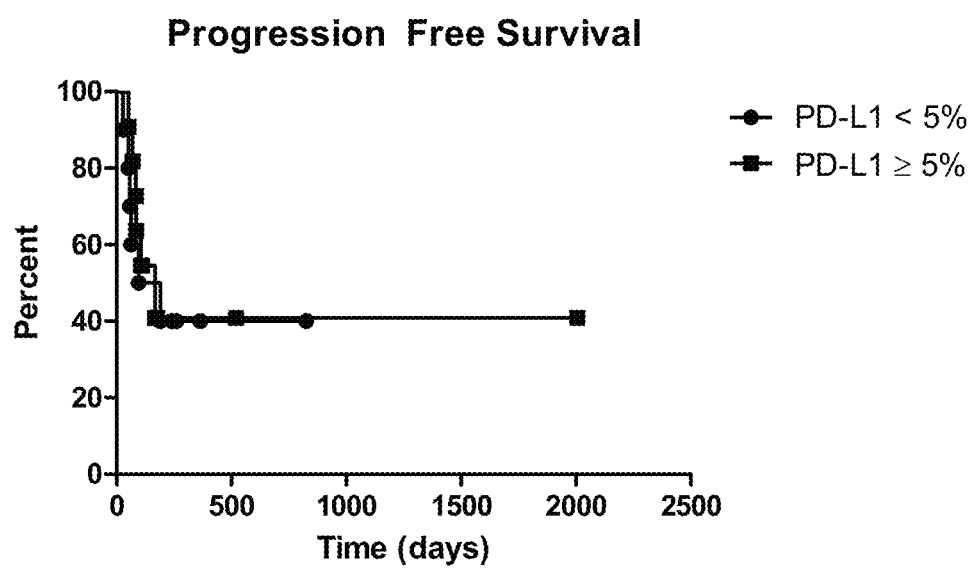
FIG. 15 shows a comparison of PD-L1 expression with progression free survival of the patients.

FIG. 4 is a second flowchart depicting the steps of a second embodiment of a method for scoring sample comprising tumor tissue taken from a cancer patient. In step 401, image data is obtained and in step 402, the image data is unmixed such that data specific to various types of fluorescence signals are separated into different channels. In step 403, data from a first channel is used to generate a mask of all cells in the field of view and in step 404 data from a second channel is used to generate a mask of a subset area, such as tumor area in the field of view. In step 405 the mask of all cells is combined with the subset area mask to generate a mask of subset cells and a mask of non-subset cells. In step 406, data from a third channel is used to generate a mask of all positive cells that are positive for a first biomarker (first biomarker mask). The mask of all cells is then dilated (step 407) to generate a dilated mask representative of a predetermined proximity within which an interacting cell (i.e., a cell that is positive for a second biomarker) may be found. In some embodiments, the first biomarker mask is dilated between 1 and 100 pixels. In step 408, data from a fourth channel is used to generate a mask of all cells that are positive for the second biomarker (second biomarker mask). In step 409, the dilated first biomarker mask and the second biomarker mask are combined to generate an interaction mask identifying cells that are positive for the second biomarker and are within the predetermined proximity of a cell positive for the first biomarker. In step 410, a spatial proximity score is calculated by dividing the area of the interaction mask by an area of all subset cells, or of all cells (as indicated by the dotted lines in the flowchart of FIG. 15 representing use of either input). In some embodiments, the subset cells are cells that are capable of being positive for the second biomarker. In some embodiments, the cells that are capable of being positive for the second biomarker are tumor cells or non-tumor cells.

In some embodiments, a subset of cells identified by a subset biomarker and a non-subset of cells corresponds to tumor cells and non-tumor cells, respectively or vice versa. In some embodiments, a subset of cells identified by a subset biomarker and a non-subset of cells corresponds to viable cells and non-viable cells, respectively or vice versa. In some embodiments, a subset of cells identified by a subset biomarker is a subset of viable cells and a non-subset of cells consists of the viable cells not included in the subset of viable cells. In some embodiments, a subset of cells identified by a subset biomarker and a non-subset of cells corresponds to T cells and non-T cells, respectively or vice versa. In some embodiments, a subset of cells identified by a subset biomarker and a non-subset of cells corresponds to myeloid cells and non-myeloid cells, respectively or vice versa.

In some embodiment, the spatial proximity score is representative of a nearness of a pair of cells. In some embodiments, the nearness of a pair of cells may be determined by a proximity between the boundaries of the pair of cells, a proximity between the centers of mass of the pair of cells, using boundary logic based on a perimeter around a selected first cell of the pair of cells, determining an intersection in the boundaries of the pair of cells, and/or by determining an area of overlap of the pair of cells.

In some embodiment, the spatial proximity score is associated with metadata associated with the images of the sample, included in a generated report, provided to an operator to determine immunotherapy strategy, recorded in a database, associated with a patient's medical record, and/or displayed on a display device.

In some embodiments, the system provides a superior predictive power compared to a quantitation of expression of the first biomarker of interest or a quantitation of expression of the second biomarker of interest.

In the methods disclosed herein, the manipulation of the digital images may be carried out by a computing system comprising a controller, such as the controller illustrated in the block diagram of FIG. 2, according to an exemplary embodiment. Controller 200 is shown to include a communications interface 202 and a processing circuit 204. Communications interface 202 may include wired or wireless interfaces (e.g., jacks, antennas, transmitters, receivers, transceivers, wire terminals, etc.) for conducting data communications with various systems, devices, or networks. For example, communications interface 202 may include an Ethernet card and port for sending and receiving data via an Ethernet-based communications network and/or a WiFi transceiver for communicating via a wireless communications network. Communications interface 202 may be configured to communicate via local area networks or wide area networks (e.g., the Internet, a building WAN, etc.) and may use a variety of communications protocols (e.g., BACnet, IP, LON, etc.).

Communications interface 202 may be a network interface configured to facilitate electronic data communications between controller 200 and various external systems or devices (e.g., imaging device 102). For example, controller 200 may receive imaging data for the selected fields of view from the imaging device 102, to analyze the data and calculate the spatial proximity score (SPS).

Still referring to FIG. 2, processing circuit 204 is shown to include a processor 206 and memory 208. Processor 206 may be a general purpose or specific purpose processor, an application specific integrated circuit (ASIC), one or more field programmable gate arrays (FPGAs), a group of processing components, or other suitable processing components. Processor 506 may be configured to execute computer code or instructions stored in memory 508 or received from other computer readable media (e.g., CDROM, network storage, a remote server, etc.).

Memory 208 may include one or more devices (e.g., memory units, memory devices, storage devices, etc.) for storing data and/or computer code for completing and/or facilitating the various processes described in the present disclosure. Memory 208 may include random access memory (RAM), read-only memory (ROM), hard drive storage, temporary storage, non-volatile memory, flash memory, optical memory, or any other suitable memory for storing software objects and/or computer instructions. Memory 208 may include database components, object code components, script components, or any other type of information structure for supporting the various activities and information structures described in the present disclosure. Memory 508 may be communicably connected to processor 206 via processing circuit 204 and may include computer code for executing (e.g., by processor 206) one or more processes described herein.

Still referring to FIG. 2, controller 200 is shown to receive input from an imaging device 102. The imaging device acquires all of the imaging data and records it, along with all of the meta-data which describes it. The imaging device will then serialize the data into a stream which can be read by controller 200. The data stream may accommodate any binary data stream type such as the file system, a RDBM or direct TCP/IP communications. For use of the data stream, controller 200 is shown to include a spectral unmixer 210. The spectral unmixer 210 may receive image data from an imaging device 102 on which it performs spectral unmixing to unmix an image presenting various wavelengths into individual, discrete channels for each band of wavelengths. For example, the image data may be "unmixed" into separate channels for each of the various fluorophores used to identify cells or proteins of interest in the tissue sample. The fluorophore, by way of example only, may be one or more of the group consisting of DAPI, Cy® 2, Cy® 3, Cy® 3.5, Cy® 5, FITC, TRITC, a 488 dye, a 555 dye, a 594 dye, and Texas Red. In one example, one of the channels may include image data that falls within a predetermined band surrounding a wavelength of 461 nm (the maximum emission wavelength for DAPI), to identify nuclei in the image. Other channels may include image data for different wavelengths to identify different portions of the tissue sample using different fluorophores.

Controller 200 is also shown to include various maskers, such as cell masker 212, subset area masker 216, first biomarker masker 22, and second biomarker masker 224. These, or other maskers that may be included in the controller 200 in other embodiments, are used to receive an unmixed signal from the spectral unmixer 210 and create a mask for the particular cell or area of interest, dependent on the fluorophore used to identify certain features of interest in the tissue sample. To create a mask, the maskers (such as cell masker 212, subset area masker 216, first biomarker masker 22, and second biomarker masker 224) receive image data related to an intensity of each pixel in the field of view. Pixel intensity is directly proportional to the amount of fluorescence emitted by the sample, which in turn, is directly proportional to the amount of protein biomarker in the sample (when using a fluorophore to identify a particular biomarker). An absolute threshold may be set based on the values which exist in the image pixels. All the pixels which are greater than or equal to the threshold value will be mapped to 1.0, or "on", and all other pixels will be mapped to 0.0, or "off." In this way, a binary mask is created to identify the cell or tissue portion of interest in the field of view. In other embodiments, a mask is created using a lower bound wherein all pixels with an intensity at or above a lower bound are accepted and used as the pixel value for the mask. If the intensity is below the lower bound, the pixel value is set to 0.0, or "off".

Figure 5:
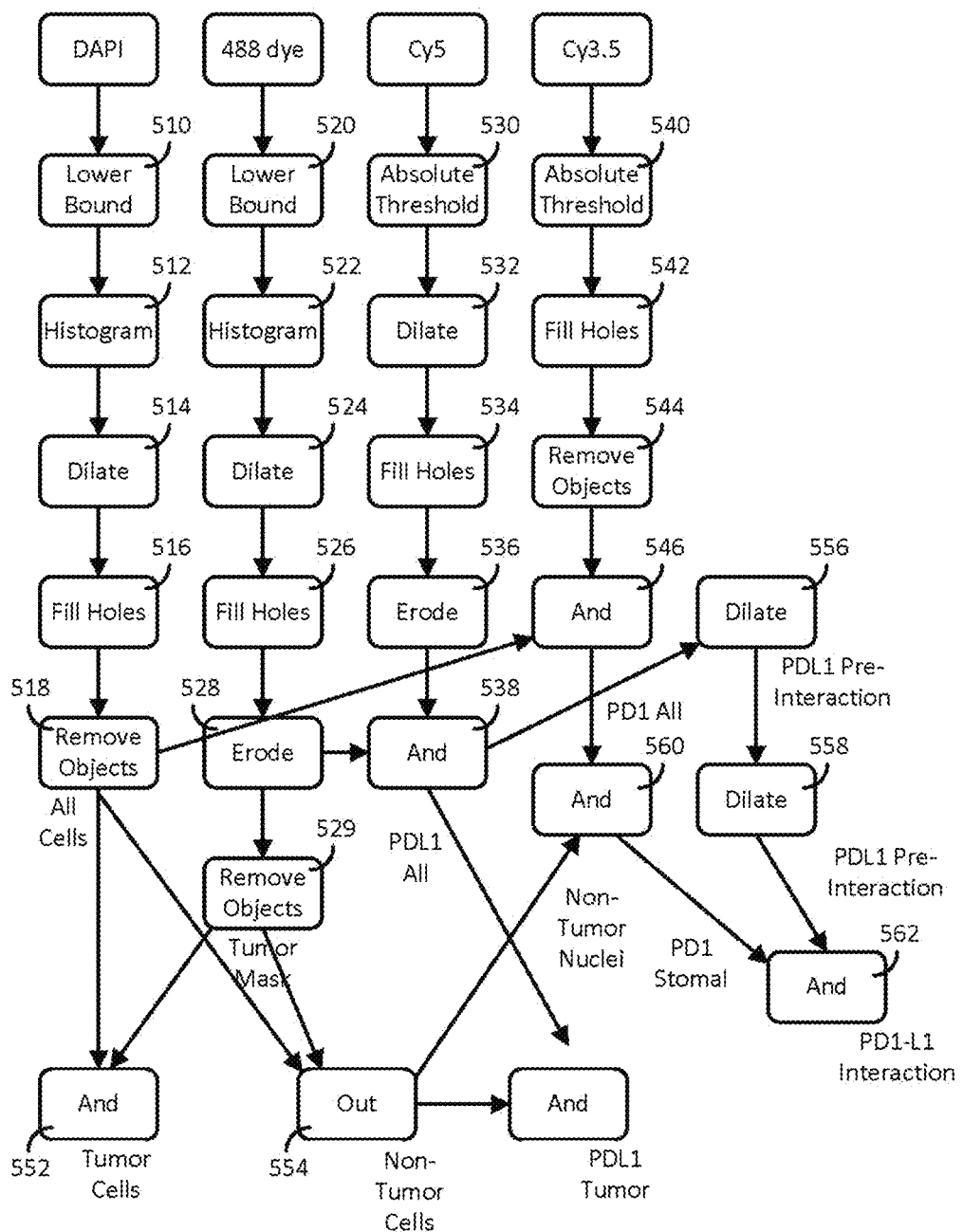
FIG. 5 is a flow diagram of the image processing steps used to score a sample comprising tumor tissue, according to an exemplary embodiment.

In the example flow diagram for masking shown in FIG. 5, it is shown that the channels for fluorescence signals identifying nuclei and tumor areas (such as DAPI and dye 488 channels, respectively) use the lower bound protocol (steps 510, 512, 520, 522), while channels for identifying biomarkers (such as Cy5 and Cy3.5 channels) use a threshold value protocol (steps 530, 540), for providing the mask outputs. In association with the lower bound protocol, there is also a histogram step to determine the lower bound. In particular, histogram threshold (step 512, 522) produces a threshold of an input image but uses a sliding scale to determine the point at which the thresholding occurs. The inputs are the current image and a user defined threshold percentage. The latter is used to determine at what percent of the total intensity the threshold level should be set. Firstly, the intensity of every pixel is summed into a total intensity. The threshold percentage is multiplied by this total intensity to obtain a cut-off sum. Finally, all pixels are grouped by intensity (in a histogram) and their intensities summed from lowest to highest (bin by bin) until the cut-off sum is achieved. The last highest pixel intensity visited in the process is the threshold for the current image. All pixels with intensities greater than that value have their intensities set to maximum while all others are set to the minimum.

The steps identified as steps 514, 516, 524, 526, 528, 532, 534, 536, 542, 544 in FIG. 5 represent intermediary steps that occur in the initial maskers, such as cell masker 212, subset area masker 216, first biomarker masker 222, and second biomarker masker 224. These steps are defined as follows:

Dilate increases the area of brightest regions in an image. Two inputs are need for dilate. The first is the implicit current image and the second is the number of iterations to dilate. It is assumed that only binary images are used for the first input. The procedure will operate on continuous images, but the output will not be a valid dilate. The dilate process begins by first finding the maximum pixel intensity in the image. Subsequently, each pixel in the image is examined once. If the pixel under investigation has intensity equal to the maximum intensity, that pixel will be drawn in the output image as a circle with iterations radius and centered on the original pixel. All pixels in that circle will have intensity equal to the maximum intensity. All other pixels are copied into the output image without modification.

The fill holes procedure will fill "empty" regions of an image with pixels at maximum intensity. These empty regions are those that have a minimum intensity and whose pixel area (size) is that specified by the user. The current image and size are the two inputs required. Like dilate this procedure should only be applied to binary images.

Erode processes images in the same fashion as dilate. All functionality is the same as dilate except that the first step determines the minimum intensity in the image, only pixels matching that lowest intensity are altered, and the circles used to bloom the found minimum intensity pixels are filled with the lowest intensity value. Like dilate this procedure should only be applied to binary images.

Remove Objects. Two inputs are expected: the current image and object size. Remove objects is the opposite of the fill holes procedure. Any regions containing only pixels with maximum intensity filling an area less than the input object size will be set to minimum intensity and thusly "removed." This procedure should only be applied to binary images; application to continuous images may produce unexpected results.

The output at final steps 518, 529, 538, and 546 are the resultant cell mask, subset area mask (or, in this particular example, the tumor area mask), biomarker 1 cell mask, and biomarker 2 cell mask, respectively. FIG. 5 further depicts the combinations of these resultant masks to calculate the spatial proximity score. These combinations are described below with reference to the combination maskers of the controller 200, depicted in FIG. 2.

Controller 200 is shown to include combination maskers, such as subset cell masker 218, non-subset cell masker 220, and interaction masker 230. Subset cell masker performs an And operation, as shown at step 552 in FIG. 5, to combine the output of the cell masker 212 (representative of all cells in the image) with the output of the subset area masker 216. Accordingly, subset cell masker generates a mask of all subset cells in the image. In some embodiments, the subset cells are tumor cells. In some such embodiments, the subset cell masker 218 is a tumor masker and the non-subset cell masker 220 is a non-tumor masker. This same combination, using an Out operation performed by non-subset cell masker 220 as shown at step 554 in FIG. 5, generates a mask of all non-subset cells in the sample image. In some embodiments, the non-subset cells are non-tumor cells.

Before being combined with another mask, the first biomarker mask (from first biomarker masker 222) is dilated by dilator 226. The dilated mask represents an area surrounding those cells expressing a first biomarker, so as to identify a space in which cells expressing the second biomarker would be within a proper proximity to interact with the cell expressing the first biomarker. This is represented by steps 556 and 558 of FIG. 5. The flow chart of FIG. 5 shows the dilation taking place in two steps, 556 and 558. This may be required when there is a limit to the maximum iterations in each step. For example, there may be a maximum of 10 iterations (corresponding to a 10 pixel increase), so when a 20 pixel increase is needed, the dilation must be split into two subsequent steps.

Within second biomarker masker 224, the biomarker mask may be combined with the non-subset cell mask described above, using an And operation, as shown in step 560 of FIG. 5, to generate a mask of all non-subset cells that are positive for the first biomarker. This mask is then combined (step 562) at interaction masker 230 with the dilated mask from dilator 226 to generate an interaction mask. The interaction mask identified the non-tumor cells that are positive for the second biomarker and that are also within the interaction area, or that overlap the dilated mask. These identified cells, then, represent the cells that could interact with the cells positive for the first biomarker, thus resulting in greater therapy response.

To calculate a spatial proximity score (SPS), the area of the interaction mask is determined in pixels at the area evaluator 232. In some embodiments, the area of all the cells that are capable of expressing the second biomarker, is determined in pixels at the area evaluator 234. The cells that are capable of expressing the second biomarker may be tumor cells or non-tumor cells. In some embodiments, the area of all cells in the field of view is determined in pixels at the area evaluator 234. An interaction, or spatial proximity, score is determined at the interaction calculator 236 by dividing the area from area evaluator 232 by the area from area evaluator 234 and multiplying by a predetermined factor. As described above, in one embodiment, the equation executed by the interaction calculator 236 is:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the normalization factor. Here, the normalization is the total area of cells that have a capacity to express the second specific biomarker. In some embodiments, the normalization factor is the total area of all tumor or non-tumor cells. In some embodiments, the normalization factor is the total area of all cells.

The And procedure is modeled after a binary AND operation, but differs in significant ways. And accepts the current image and a user selected resultant. The output is an image created by performing a multiplication of the normalized intensities of matching pixels from the two input images. In some applications, image intensity data is already normalized. Therefore, the And procedure is simply a pixel-wise multiplication of the two images. The two inputs required for Out are the current image and a user selected resultant. Out removes the second image form the first according to the formula $A*(1-B/B_{max})$ where A is the current image, B the user selected image to remove, and $B_{max}$ is the maximum intensity of B. Note that the division of B by $B_{max}$ normalizes B.

In some embodiments, provided herein is an imaging system for scoring a sample comprising tumor tissue taken from a cancer patient, the imaging system comprising an imaging apparatus comprising a stage for positioning the sample in an imaging field, an electromagnetic radiation source for directing electromagnetic radiation at the sample, and a detector configured to detect electromagnetic radiation from the sample, and a controller. The controller comprises a user interface for exchanging information between an operator and the electronic control system and a processing circuit configured to execute instructions stored on a computer-readable medium. The instructions cause the electronic control system of the imaging system to: (i) receive information about the detected electromagnetic radiation from the imaging apparatus;

(ii) generate image data based on the detected electromagnetic radiation; (iii) analyze the image data to determine a score representative of a nearness between at least one pair of cells, a first member of the least one pair of cells expressing a first biomarker and a second member of the at least one pair of cells expressing a second biomarker that is different from the first biomarker; and (iv) record the score, which score when compared to a threshold value is indicative of a likelihood that the cancer patient will respond positively to immunotherapy.

In some embodiments, the score representative of a nearness between at least one pair cells is representative of an extent that the pair of cells are within a predetermined proximity of one another.

In some embodiments, the first member of the at least one pair of cells comprises a tumor cell and the second member of the at least one pair of cells comprises a non-tumor cell. In some embodiments, the non-tumor cell is an immune cell. In some embodiments, the non-tumor cell is a stromal cell.

In some embodiments, the first and second members of the at least one pair of cells comprise immune cells.

In some embodiments, the first member of the at least one pair of cells comprises a tumor cell, a myeloid cell, or a stromal cell and the second member of the at least one pair of cells comprises an immune cell. In some embodiments, the tumor cell, myeloid cell, or stromal cell expresses PD-L1 and the immune cell expresses PD-1.

In some embodiments, the first member of the at least one pair of cells comprises a tumor cell and the second member of the at least one pair of cells comprises an immune cell. In some embodiments, the first member of the at least one pair of cells comprises a myeloid cell and the second member of the at least one pair of cells comprises an immune cell. In some embodiments, the first member of the at least one pair of cells comprises a stromal cell and the second member of the at least one pair of cells comprises an immune cell. In some embodiments, the first member of the at least one pair of cells expresses PD-L1 and the immune cell expresses PD-1.

In some embodiments, the first member of the at least one pair of cells expresses a first biomarker selected from the group consisting of PD-L1, PD-L2. B7-H3, B7-H4, HLA-DR, Galectin 9, CD80, CD86, 4.1BBL, ICOSL, CD40, OX40L, IDO-1, GITRL, and combinations thereof. In some embodiments, the second member of the at least one pair of cells expresses a second biomarker selected from the group consisting of PD-1, TIM3, LAG3, 41BB, OX40, CTLA-4, CD40L, CD28, GITR. ICOS, CD28, and combinations thereof. In some embodiments, the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof.

In some embodiments, the first member of the at least one pair of cells expresses PD-L1 and the second member of the at least one pair of cells expresses PD-1. In some embodiments, the first member of the at least one pair of cells expresses PD-L1 and the second member of the at least one pair of cells expresses CD80. In some embodiments, the first member of the at least one pair of cells expresses CTLA-4 and the second member of the at least one pair of cells expresses CD80. In some embodiments, the first member of the at least one pair of cells expresses PD-L2 and the second member of the at least one pair of cells expresses PD-1. In some embodiments, the first member of the at least one pair of cells expresses CTLA-4 and the second member of the at least one pair of cells expresses CD86. In some embodiments, the first member of the at least one pair of cells expresses LAG-3 and the second member of the at least one pair of cells expresses HLA-DR. In some embodiments, the first member of the at least one pair of cells expresses TIM-3 and the second member of the at least one pair of cells expresses Galectin 9. In some embodiments, the first member of the at least one pair of cells expresses 41BB and the second member of the at least one pair of cells expresses 4.1BBL. In some embodiments, the first member of the at least one pair of cells expresses OX40 and the second member of the at least one pair of cells expresses OX40L. In some embodiments, the first member of the at least one pair of cells expresses CD40 and the second member of the at least one pair of cells expresses CD40L. In some embodiments, the first member of the at least one pair of cells expresses ICOS and the second member of the at least one pair of cells expresses ICOSL. In some embodiments, the first member of the at least one pair of cells expresses GITR and the second member of the at least one pair of cells expresses GITRL. In some embodiments, the first member of the at least one pair of cells expresses HLA-DR and the second member of the at least one pair of cells expresses TCR.

In some embodiments, the first biomarker expressed by the first member of the at least one pair of cells and the second biomarker expressed by the second member of the at least one pair of cells interact with one another. In some embodiments, the first biomarker expressed by the first member of the at least one pair of cells and the second biomarker expressed by the second member of the at least one pair of cells do not interact with one another.

In some embodiments, the spatial proximity between the at least one pair of cells ranges from about 0.5 µm to about 50 µm. In some embodiments, the spatial proximity ranges from 2.5 µm to about 50 µm. In some embodiments, the spatial proximity ranges from 2.5 µm to about 45 µm. In some embodiments, the spatial proximity ranges from 2.5 µm to about 40 µm. In some embodiments, the spatial proximity ranges from 2.5 µm to about 35 µm. In some embodiments, the spatial proximity ranges from 2.5 µm to about 30 µm. In some embodiments, the spatial proximity ranges from 2.5 µm to about 25 µm. In some embodiments, the spatial proximity ranges from 2.5 µm to about 20 µm. In some embodiments, the spatial proximity ranges from 2.5 µm to about 15 µm. In some embodiments, the spatial proximity ranges from 5 µm to about 50 µm. In some embodiments, the spatial proximity ranges from 5 µm to about 45 µm. In some embodiments, the spatial proximity ranges from 5 µm to about 40 µm. In some embodiments, the spatial proximity ranges from 5 µm to about 35 µm. In some embodiments, the spatial proximity ranges from 5 µm to about 30 µm. In some embodiments, the spatial proximity ranges from 5 µm to about 25 µm. In some embodiments, the spatial proximity ranges from 5 µm to about 20 µm. In some embodiments, the spatial proximity ranges from 5 µm to about 15 μm. In some embodiments, the spatial proximity is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm.

In some embodiments, the spatial proximity between the at least one pair of cells ranges from about 1 pixel to about 100 pixels. In some embodiments, the spatial proximity ranges from about 5 to about 100 pixels. In some embodiments, the spatial proximity ranges from about 5 to about 90 pixels. In some embodiments, the spatial proximity ranges from about 5 to about 80 pixels. In some embodiments, the spatial proximity ranges from about 5 to about 70 pixels. In some embodiments, the spatial proximity ranges from about 5 to about 60 pixels. In some embodiments, the spatial proximity ranges from about 5 to about 50 pixels. In some embodiments, the spatial proximity ranges from about 5 to about 40 pixels. In some embodiments, the spatial proximity ranges from about 5 to about 30 pixels. In some embodiments, the spatial proximity ranges from about 10 to about 100 pixels. In some embodiments, the spatial proximity ranges from about 10 to about 90 pixels. In some embodiments, the spatial proximity ranges from about 10 to about 80 pixels. In some embodiments, the spatial proximity ranges from about 10 to about 70 pixels. In some embodiments, the spatial proximity ranges from about 10 to about 60 pixels. In some embodiments, the spatial proximity ranges from about 10 to about 50 pixels. In some embodiments, the spatial proximity ranges from about 10 to about 40 pixels. In some embodiments, the spatial proximity ranges from about 10 to about 30 pixels. In some embodiments, the spatial proximity is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 pixels. In some embodiments, a pixel is 0.5 μm wide.

In some embodiments, generating the image data comprises (i) separating the information about the detected electromagnetic radiation into unmixed image data; and (ii) providing the data through a plurality of data channels, in which the unmixed image data in a first data channel describes fluorescence signals attributable to the first biomarker and the unmixed image data in a second data channel describes fluorescence signals attributable to the second biomarker.

In some embodiments, analyzing the data comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin sufficient to encompass proximally located cells expressing the second biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, analyzing the data comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker to encompass proximally located cells expressing the second biomarker within about 0.5 μm to about 50 μm of a plasma membrane of the cells that express the first biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, analyzing the data comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin ranging from about 1 to about 100 pixels to encompass proximally located cells expressing the second biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, analyzing the data comprises: (i) selecting a predetermined number of fields of view available from the sample comprising tumor tissue taken from the cancer patient, which is stained with a plurality of fluorescence tags, which selection is biased toward selecting fields of view that contain a greater number of cells that express the first biomarker relative to other fields of view; (ii) for each of the selected fields of view, dilating fluorescence signals attributable to the first biomarker by a margin ranging from about 1 to about 100 pixels to encompass cells expressing the second biomarker within about 0.5 μm to about 50 μm of a plasma membrane of the cells that express the first biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score.

In some embodiments, the spatial proximity score is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker (the normalization factor).

In some embodiments, the spatial proximity score (SPS) is determined by the following equation:

$$SPS = \frac{A_I}{A_{NT}} \times 10^4$$

wherein $A_I$ is a total interaction area (total area of cells expressing the second specific biomarker and encompassed by dilated fluorescence signals attributable to cells expressing the first specific biomarker) and $A_{NT}$ is the total area of non-tumor cells.

In some embodiments, the spatial proximity score is determined by the following equation:

$$SPS = \frac{A_I}{A_T} \times 10^4$$

wherein $A_I$ is a total interaction area (total area of cells expressing the second specific biomarker and encompassed by dilated fluorescence signals attributable to cells expressing the first specific biomarker) and $A_T$ is the total area of all cells.

In some embodiments, four fluorescence tags, each specific to a different biomarker, are used in the determining step. In further embodiments, a first fluorescence tag is associated with the first biomarker, a second fluorescence tag is associated with the second biomarker, a third fluorescence tag is associated with a third biomarker, and a fourth fluorescence tag is associated with a fourth biomarker. In some embodiments, the first biomarker comprises a tumor and non-tumor marker. In some embodiments, the second biomarker comprises a non-tumor marker. In some embodiments, the first biomarker comprises a tumor and non-tumor marker, and the second biomarker comprises a non-tumor marker. In some embodiments, the third biomarker is expressed by all cells. In some embodiments, the fourth biomarker is expressed only in tumor cells. In some embodiments, the third biomarker is expressed by all cells and the fourth biomarker is expressed only in tumor cells. In some embodiments, one or more fluorescence tags comprise a fluorophore conjugated to an antibody having a binding affinity for a specific biomarker or another antibody. In some embodiments, one or more fluorescence tags are fluorophores with affinity for a specific biomarker.

In some embodiments, the fluorescence signals attributable to the first biomarker are dilated by a margin ranging from about 1 to about 100 pixels. In some embodiments, the margin is from about 5 to about 100 pixels. In some embodiments, the margin is from about 5 to about 90 pixels. In some embodiments, the margin is from about 5 to about 80 pixels. In some embodiments, the margin is from about 5 to about 70 pixels. In some embodiments, the margin is from about 5 to about 60 pixels. In some embodiments, the margin is from about 5 to about 50 pixels. In some embodiments, the margin is from about 5 to about 40 pixels. In some embodiments, the margin is from about 5 to about 30 pixels. In some embodiments, the margin is from about 10 to about 100 pixels. In some embodiments, the margin is from about 10 to about 90 pixels. In some embodiments, the margin is from about 10 to about 80 pixels. In some embodiments, the margin is from about 10 to about 70 pixels. In some embodiments, the margin is from about 10 to about 60 pixels. In some embodiments, the margin is from about 10 to about 50 pixels. In some embodiments, the margin is from about 10 to about 40 pixels. In some embodiments, the margin is from about 10 to about 30 pixels. In some embodiments, the margin is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 pixels. In some embodiments, a pixel is 0.5 µm wide.

In some embodiments, dilating fluorescence signals attributable to the first biomarker encompasses proximally located cells expressing the second biomarker within about 0.5 µm to about 50 µm of a plasma membrane of the cells that express the first biomarker. In some embodiments, dilating fluorescence signals attributable to the first biomarker encompasses proximally located cells expressing the second biomarker within about 2.5 µm to about 50 µm of a plasma membrane of the cells that express the first biomarker. In some embodiments, dilating fluorescence signals attributable to the first biomarker encompasses proximally located cells expressing the second biomarker within about 2.5 µm to about 45 µm of a plasma membrane of the cells that express the first biomarker. In some embodiments, dilating fluorescence signals attributable to the first biomarker encompasses proximally located cells expressing the second biomarker within about 2.5 µm to about 40 µm of a plasma membrane of the cells that express the first biomarker. In some embodiments, dilating fluorescence signals attributable to the first biomarker encompasses proximally located cells expressing the second biomarker within about 2.5 µm to about 35 µm of a plasma membrane of the cells that express the first biomarker. In some embodiments, dilating fluorescence signals attributable to the first biomarker encompasses proximally located cells expressing the second biomarker within about 2.5 µm to about 30 µm of a plasma membrane of the cells that express the first biomarker. In some embodiments, dilating fluorescence signals attributable to the first biomarker encompasses proximally located cells expressing the second biomarker within about 2.5 µm to about 25 µm of a plasma membrane of the cells that express the first biomarker. In some embodiments, dilating fluorescence signals attributable to the first biomarker encompasses proximally located cells expressing the second biomarker within about 2.5 µm to about 20 µm of a plasma membrane of the cells that express the first biomarker. In some embodiments, dilating fluorescence signals attributable to the first biomarker encompasses proximally located cells expressing the second biomarker within about 2.5 µm to about 15 µm of a plasma membrane of the cells that express the first biomarker. In some embodiments, dilating fluorescence signals attributable to the first biomarker encompasses proximally located cells expressing the second biomarker within about 5 µm to about 50 µm of a plasma membrane of the cells that express the first biomarker. In some embodiments, dilating fluorescence signals attributable to the first biomarker encompasses proximally located cells expressing the second biomarker within about 5 µm to about 45 µm of a plasma membrane of the cells that express the first biomarker. In some embodiments, dilating fluorescence signals attributable to the first biomarker encompasses proximally located cells expressing the second biomarker within about 5 µm to about 40 µm of a plasma membrane of the cells that express the first biomarker. In some embodiments, dilating fluorescence signals attributable to the first biomarker encompasses proximally located cells expressing the second biomarker within about 5 µm to about 35 μm of a plasma membrane of the cells that express the first biomarker. In some embodiments, dilating fluorescence signals attributable to the first biomarker encompasses proximally located cells expressing the second biomarker within about 5 μm to about 30 μm of a plasma membrane of the cells that express the first biomarker. In some embodiments, dilating fluorescence signals attributable to the first biomarker encompasses proximally located cells expressing the second biomarker within about 5 μm to about 25 μm of a plasma membrane of the cells that express the first biomarker. In some embodiments, dilating fluorescence signals attributable to the first biomarker encompasses proximally located cells expressing the second biomarker within about 5 μm to about 20 μm of the cells that express the first biomarker. In some embodiments, dilating fluorescence signals attributable to the first biomarker encompasses proximally located cells expressing the second biomarker within about 5 μm to about 15 μm of a plasma membrane of the cells that express the first biomarker. In some embodiments, dilating fluorescence signals attributable to the first biomarker encompasses proximally located cells expressing the second biomarker within about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μm of a plasma membrane of the cells that express the first biomarker. In some embodiments, the second biomarker on the proximally located cells is in direct contact with the first biomarker.

In some embodiments, the first total area for all cells from each of the selected fields of view, which express the second biomarker, is measured in pixels.

In some embodiments, the normalization factor is a second total area for all non-tumor cells from each of the selected fields of view. In some embodiments, the second total area is measured in pixels. In some embodiments, both the first total area and the second total area measured in pixels.

In some embodiments, the normalization factor is a second total area for all cells from each of the selected fields of view which have the capacity to express the second biomarker. In some embodiments, the second total area is measured in pixels. In some embodiments, both the first total area and the second total area measured in pixels.

In some embodiments, the normalization factor is a second total area for all cells from each of the selected fields of view. In some embodiments, the second total area is measured in pixels. In some embodiments, both the first total area and the second total area measured in pixels.

In some embodiments, the threshold score is about 500 to about 5000. In some embodiments, the threshold score is about 500 to about 4500. In some embodiments, the threshold score is about 500 to about 4000. In some embodiments, the threshold score is about 500 to about 3500. In some embodiments, the threshold score is about 500 to about 3000. In some embodiments, the threshold score is about 500 to about 2500. In some embodiments, the threshold score is about 500 to about 2000. In some embodiments, the threshold score is about 500 to about 1500. In some embodiments, the threshold score is about 500 to about 1000. In some embodiments, the threshold score is about 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, including increments therein. In some embodiments, the threshold score is about 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, including increments therein, plus or minus 100.

In some embodiments, the predetermined factor is from about 10 to about $10^5$. In some embodiments, the predetermined factor is from about $10^2$ to about $10^5$. In some embodiments, the predetermined factor is from about $10^3$ to about $10^5$. In some embodiments, the predetermined factor is from about $10^4$ to about $10^5$. In some embodiments, the predetermined factor is about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000, 70000, 80000, 90000, or $10^5$, including increments therein.

In some embodiments, the predictive power is quantified as a positive predictive value, a negative predictive value, or a combination thereof. A positive predictive value is calculated by dividing the number of patients who respond to treatment with scores above the threshold score by the total number of patients who respond to treatment. A negative predictive value is calculated by dividing the number of patients who do not respond to treatment with scores below the threshold score by the total number of patients who do not respond to treatment.

In some embodiments, the positive predictive value is greater than 60%. In some embodiments, the positive predictive value is 65% or greater. In some embodiments, the positive predictive value is 70% or greater. In some embodiments, the positive predictive value is 75% or greater. In some embodiments, the positive predictive value is 80% or greater. In some embodiments, the positive predictive value is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, including increments therein.

In some embodiments, the negative predictive value is 60% or greater. In some embodiments, the negative predictive value is 65% or greater. In some embodiments, the negative predictive value is 70% or greater. In some embodiments, the negative predictive value is 75% or greater. In some embodiments, the negative predictive value is 80% or greater. In some embodiments, the negative predictive value is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, including increments therein.

In another aspect, disclosed herein are methods utilizing a system comprising an imaging device and a controller for determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first specific biomarker relative to other fields of view; (ii) for each of the selected fields of view, dilating fluorescence signals attributable to the first specific biomarker to encompass proximally located cells expressing a second specific biomarker; and (iii) dividing a first total area for all cells from each of the selected fields of view, which express the second specific biomarker and are encompassed within the dilated fluorescence signals attributable to the cells expressing the first specific biomarker, with a normalization score, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein methods utilizing a system comprising an imaging device and a controller for determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker to encompass cells expressing a second biomarker within about 0.5 µm to about 50 µm of a plasma membrane of the cells that express the first biomarker; and (iii) dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein are methods utilizing a system comprising an imaging device and a controller for determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker by a margin ranging from about 1 to about 100 pixels to encompass proximally located cells expressing a second biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In another aspect, disclosed herein are methods utilizing a system comprising an imaging device and a controller for determining a score representative of a spatial proximity between at least one pair of cells selected from among a plurality of cells present in a predetermined number of fields of view available from a sample comprising tumor tissue, which sample is taken from a cancer patient, the method comprising: (i) selecting a predetermined number of fields of view available from the sample comprising tumor tissue taken from the cancer patient, which is stained with a plurality of fluorescence tags, which selection is biased toward selecting fields of view that contain a greater number of cells that express a first biomarker relative to other fields of view; (ii) for each of the selected fields of view, dilating fluorescence signals attributable to the first biomarker by a margin ranging from about 1 to about 100 pixels to encompass cells expressing a second biomarker within about 0.5 µm to about 50 µm of a plasma membrane of the cells that express the first biomarker; and (iii) dividing a first total area, as measured in pixels, for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score. In some embodiments, the method provides a superior predictive power compared to a quantitation of expression of the first specific biomarker or a quantitation of expression of the second specific biomarker.

In some embodiments, the spatial proximity score (SPS) is determined by the following equation:

$$SPS = \frac{A_I}{A_{NT}} \times 10^4$$

wherein $A_I$ is a total interaction area (total area of cells expressing the second specific biomarker and encompassed by dilated fluorescence signals attributable to cells expressing the first specific biomarker) and $A_{NT}$ is the total area of non-tumor cells.

In some embodiments, the spatial proximity score is determined by the following equation:

$$SPS = \frac{A_I}{A_C} \times 10^4$$

wherein $A_I$ is a total interaction area (total area of cells expressing the second specific biomarker and encompassed by dilated fluorescence signals attributable to cells expressing the first specific biomarker) and $A_C$ is the total area of cells that have a capacity to express the second specific biomarker.

In another aspect, disclosed are methods utilizing a system comprising an imaging device and a controller for scoring a sample comprising tumor tissue from a cancer patient that are used in methods of treating cancer in the patient. In some embodiments, the methods of scoring a sample comprising tumor tissue from a cancer patient are performed prior to administration of immunotherapy. In some embodiments, the method provides a superior predictive power compared to a quantitation of expression of the first specific biomarker or a quantitation of expression of the second specific biomarker.

In some embodiments, the spatial proximity score is determined by the following equation:

$$SPS = \frac{A_I}{A_T} \times 10^4$$

wherein $A_I$ is a total interaction area (total area of cells expressing the second specific biomarker and encompassed by dilated fluorescence signals attributable to cells expressing the first specific biomarker) and $A_T$ is the total area of all cells.

In some embodiments, disclosed herein are methods utilizing a system comprising an imaging device and a controller for treating cancer in a patient in need thereof, the method comprising: (a) scoring a sample comprising tumor tissue taken from the patient comprising (i) using the sample comprising tumor tissue taken from the patient, determining a score representative of a spatial proximity between at least one pair of cells, a first member of the at least one pair of cells expressing a first biomarker and a second member of the at least one pair of cells expressing a second biomarker that is different from the first biomarker; and (ii) recording the score: (b) comparing the score to a threshold value; and (b) administering immunotherapy to the patient if the score when compared to the threshold value is indicative of a likelihood that the patient will respond positively to the immunotherapy. In some embodiments, the determining step is as described herein. In some embodiments, the method provides a superior predictive power compared to a quantitation of expression of the first specific biomarker or a quantitation of expression of the second specific biomarker.

In some embodiments, disclosed herein are methods of scoring a tissue sample comprising: (i) using an imaging system to obtain image data for the tissue sample taken from a cancer patient, the imaging system comprising: a housing comprising a stage for positioning the sample in an imaging field, an electromagnetic radiation source for directing electromagnetic radiation at the sample, and a detector for collecting electromagnetic radiation output; and an electronic control system comprising memory and an processing circuit having image processing modules; (ii) analyzing, using the image processing modules, the image data to determine a score representative of a nearness between a pair of cells, a first member of the pair of cells expressing a first biomarker and a second member of the pair of cells expressing a second biomarker that is different from the first biomarker; and (iii) recording the score in the memory, which score when compared to a threshold value is indicative of a likelihood that the cancer patient will respond positively to immunotherapy. In some embodiments, the method provides a superior predictive power compared to a quantitation of expression of the first specific biomarker or a quantitation of expression of the second specific biomarker.

In some embodiments, disclosed herein are tissue sample scoring systems comprising: an imaging device that obtains image data of a tissue sample taken from a cancer patient; and a controller that receives image data from the imaging device and analyzes the data to determine a score representative of a nearness between a pair of cells, a first member of the at least one pair of cells expressing a first biomarker and a second member of the at least one pair of cells expressing a second biomarker that is different from the first biomarker, wherein the score, when compared to a threshold value is indicative of a likelihood that the cancer patient will respond positively to immunotherapy. In some embodiments, the method provides a superior predictive power compared to a quantitation of expression of the first specific biomarker or a quantitation of expression of the second specific biomarker.

EXAMPLES

Example 1. Sample Preparation, Imaging, and Analysis of Imaging for Melanoma Tissue Samples from Human Patients Sample Preparation.

Figure 6:
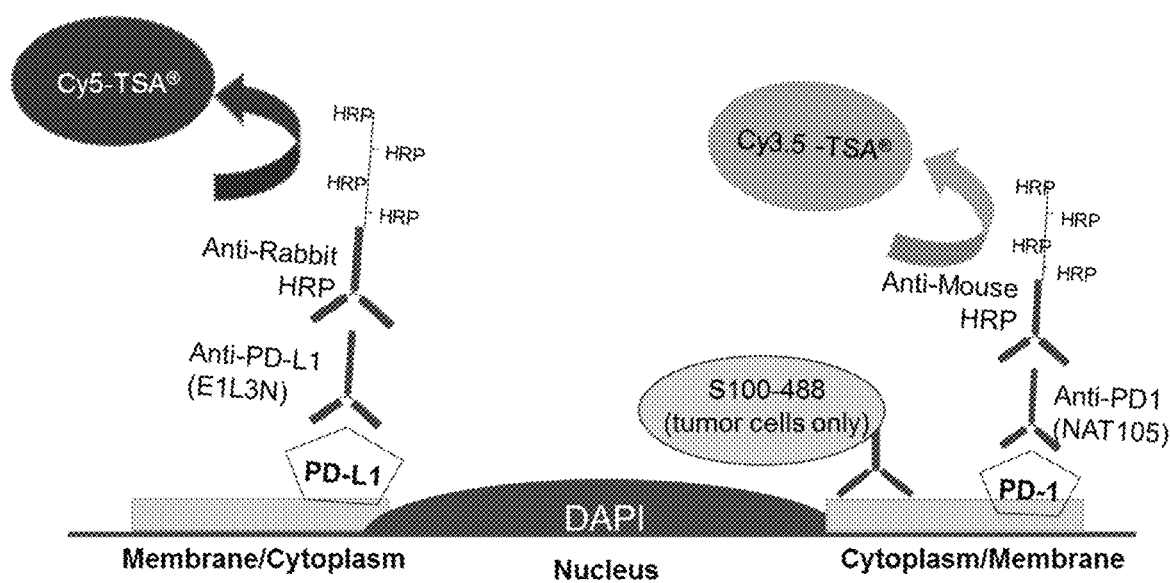
FIG. 6 shows a non-limiting example of an overview of antibodies and detection reagents used in the preparation of tissue samples for imaging and analysis.

Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with a mouse anti-PD1 primary antibody. Slides were then washed before incubation with an anti-mouse HRP secondary antibody. Slides were washed and then PD-1 staining was detected using TSA+Cy® 3.5 (Perkin Elmer). Any residual HRP was then quenched using two washes of fresh 100 mM benzhydrazide with 50 mM hydrogen peroxide. The slides were again washed before staining with a rabbit anti-PD-L1 primary antibody. Slides were washed and then incubated with a cocktail of anti-rabbit HRP secondary antibody plus mouse anti-S100 directly labeled with 488 dye and 4',6-diamidino-2-phenylindole (DAPI). Slides were washed and then PD-L1 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 6. Alternatively, slides were stained with anti-CD8 primary antibody in place of anti-PD1 primary antibody.

Sample Imaging and Analysis.

Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue), FITC (green), and Cy® 5 (red) to create RGB images. These 4× images were processed using an automated enrichment algorithm (developed using inForm) in field of view selector 101 to identify and rank possible 20× magnification fields of view according to the highest Cy® 5 expression.

The top 40 fields of view were imaged at 20× magnification across DAPI, FITC, Texas Red, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 210 into individual channels and saved as a separate file.

The processed files were further analyzed using AQUAnalysis™ or through a fully automated process using AQUAserve™. Details were as follows.

Figure 7A:
FIG. 7a shows a non-limiting example of all nuclei detected with DAPI within an image.
Figure 7B:
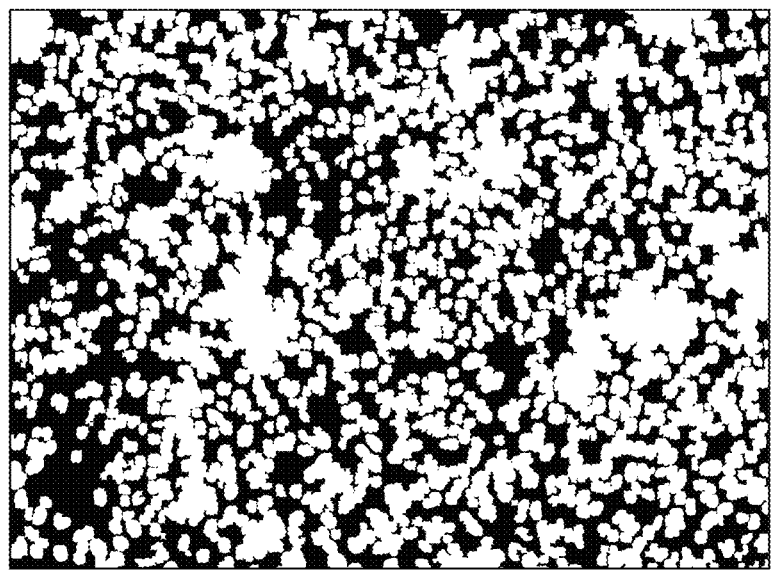

Each DAPI image was processed by cell masker 212 to identify all cell nuclei within that image (FIG. 7a), and then dilated by 3 pixels to represent the approximate size of an entire cell. This resulting mask represented all cells within that image (FIG. 7b).

Figure 8A:
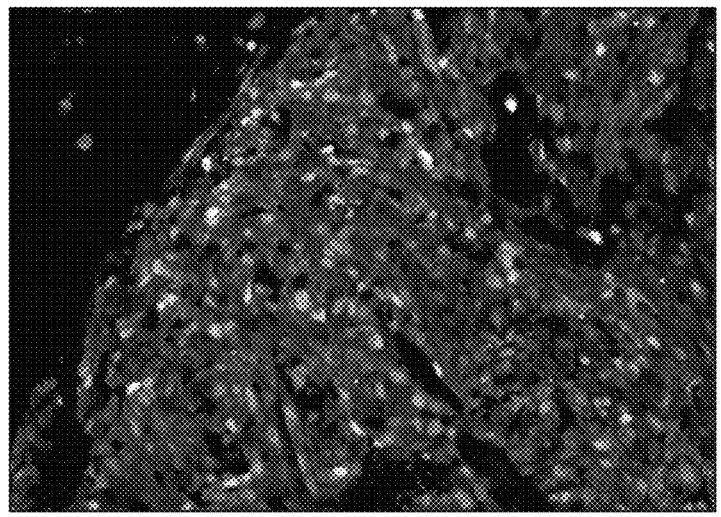
FIG. 8a shows a non-limiting example of an image of S100 detected with 488 dye.
Figure 8B:
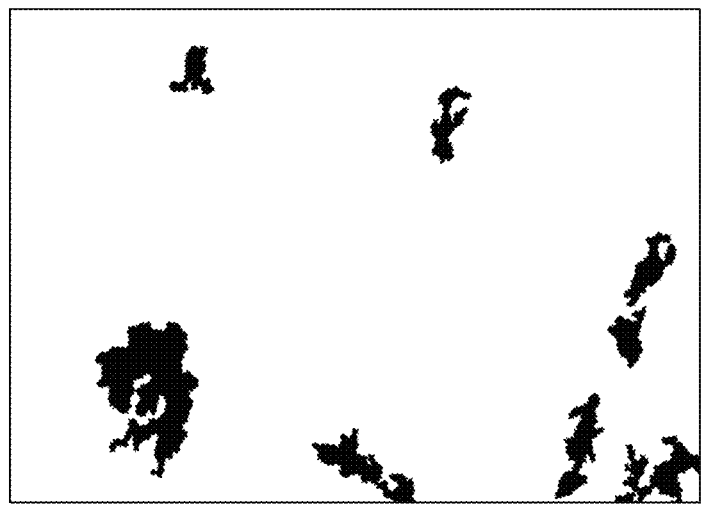

S100 (tumor cell marker for melanoma) detected with 488 dye (FIG. 8a) was processed by subset masker 216 to create a binary mask of all tumor area within that image (FIG. 8b). Overlap between this mask and the mask of all cells created a new mask for tumor cells (FIG. 8c), using tumor cell masker 218.

Similarly, absence of the tumor cell marker in combination with the mask of all nuclei created a new mask for all non-tumor cells (FIG. 8d), performed using non-tumor cell masker 220.

Figure 9A:
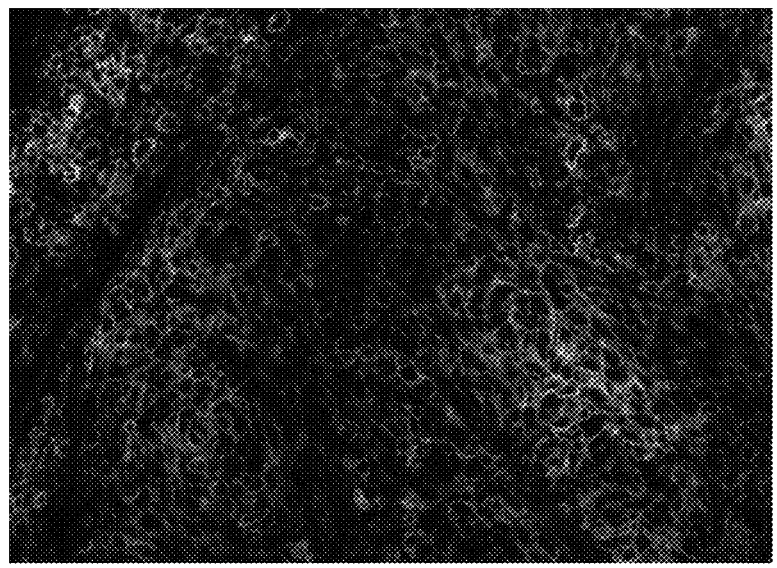
FIG. 9a shows a non-limiting example of an image of PD-L1 detected with Cy® 5.
Figure 9B:
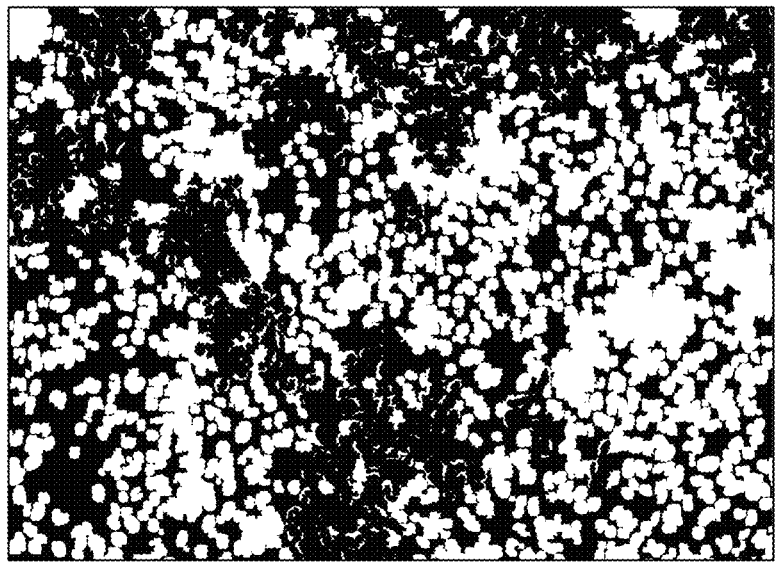

Each Cy® 5 image (FIG. 9a) was processed by first biomarker masker 222 and overlapped with the mask of all cells to create a binary mask of all cells that are PD-L1-positive (FIG. 9b). Overlapping the biomarker mask with the mask of all cells eliminated noise pixels that may be falsely identified in the mask as biomarker positive cells.

Figure 10A:
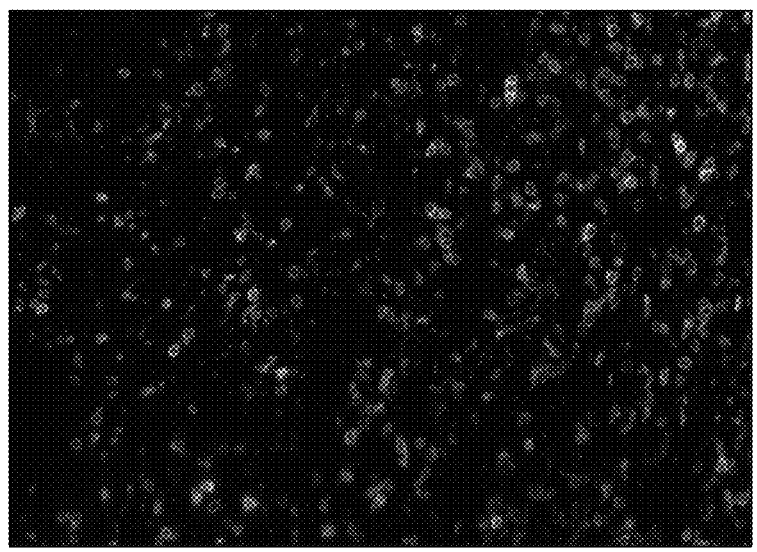
FIG. 10a shows a non-limiting example of an image of PD-1 detected with Cy® 3.5.
Figure 10B:
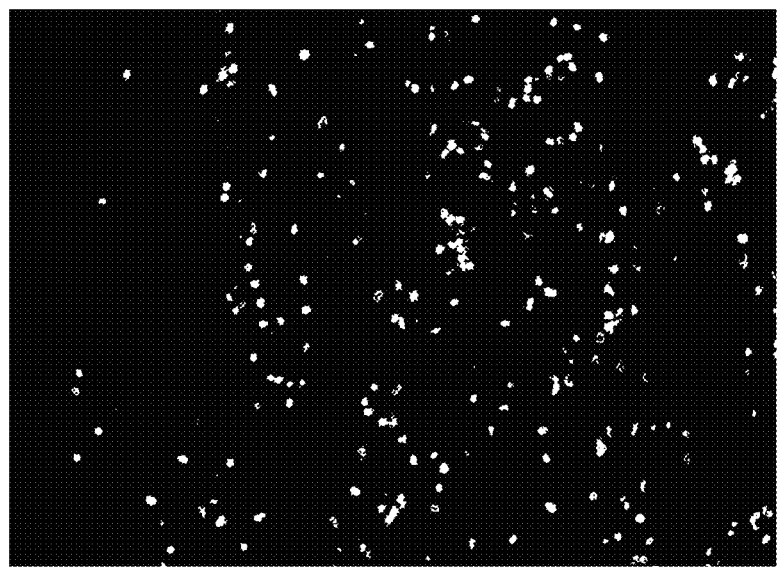

Each Cy® 3.5 image (FIG. 10a) was processed by second biomarker masker 224 to create a binary mask for PD-1-positive cells and overlapped with the mask of all non-tumor cells to create a binary mask of all non-tumor cells that are PD-1-positive (FIG. 10b). Overlapping the biomarker mask with the mask of all non-tumor cells eliminated noise pixels that may be falsely identified in the mask as biomarker positive cells.

Figure 11A:
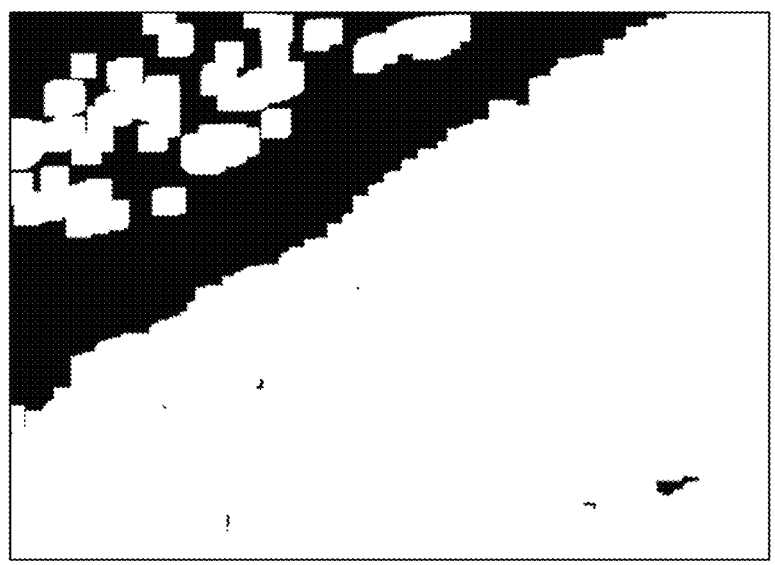
FIG. 11a shows a non-limiting example of an interaction mask of all PD-L1-positive cells and the nearest neighbor cells.
Figure 11B:
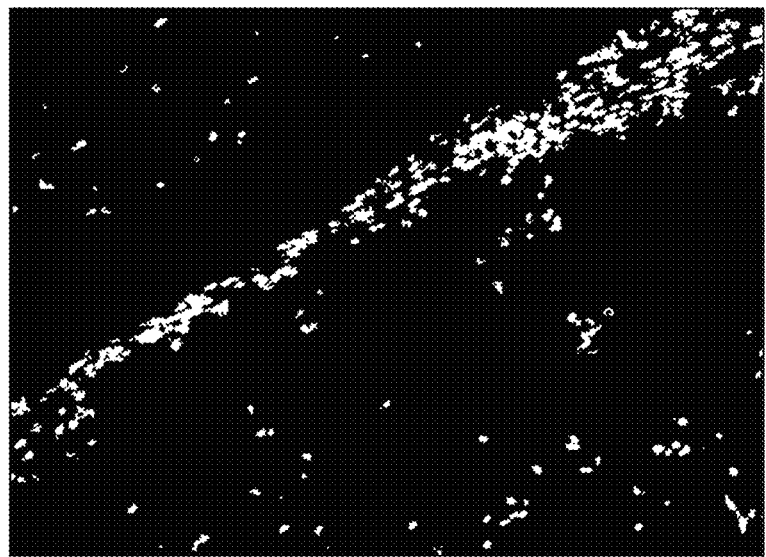
FIG. 11b shows a non-limiting example of an interaction compartment of the PD-1-positive cells in close proximity to the PD-L1-positive cells.

The binary mask of all PD-L1-positive cells was dilated using second dilator 226 to create an interaction mask encompassing the nearest neighbor cells (e.g., cells with PD-1) (FIG. 11a). This interaction mask was combined with a binary mask of all PD-1-positive non-tumor cells using interaction masker 230 to create an interaction compartment of the PD-1-positive cells in close enough proximity to the PD-L-positive cells such that PD-1 is likely interacting with PD-L1 (FIG. 11b).

The total area from all accepted fields (up to 40 fields of view) for the interaction compartment and the total area of the non-tumor cells was calculated in area evaluators 232, 234 respectively. The total area from all accepted fields of view for the interaction compartment was divided by the total area of the non-tumor cells and multiplied by a factor of 10,000, using the interaction calculator 236 to create a whole number representing an interaction score for each specimen. PD-L1 and PD-1 measurements were highly reproducible ($R^2$=0.98 and 0.97, respectively). A broad range of PD-L1 and PD-1 expression and interaction scores were observed in archival clinical specimens (n=53). In a cohort of 26 advanced melanoma patients treated with nivolumab (n=5) or pembrolizumab (n=21), the PD-1/PD-L1 interaction score was found to reliably distinguish responders from non-responders (p=0.01) while PD-L1 alone (p=0.07) or CD8 alone (p=0.23) did not. Additionally, patients exhibiting higher PD-1/PD-L1 interaction scores had superior response rates (82% vs. 20%, p=0.01). Patients with high PD-1/PD-L1 interaction scores experienced longer median progression-free survival (p=0.059), and fewer deaths (22% vs 58%) compared with patients having lower PD-1/PD-L1 interaction scores. These results suggest that this method of scoring the tissue sample to obtain PD-1/PD-L1 interaction scores provides a superior predictive power (82% Positive Predictive Value, 80% Negative Predictive Value) compared with PD-L1 expression alone.

Figure 12A:
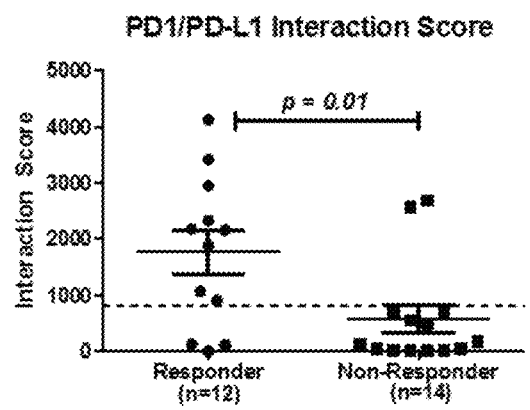
FIG. 12a shows a non-limiting example of interaction scores from 26 melanoma patients.

Representative scores from the 26 patients are shown in FIG. 12a. Based on the data, a threshold of 800-900 was selected to indicate likelihood of response to treatment.

Figure 12B:
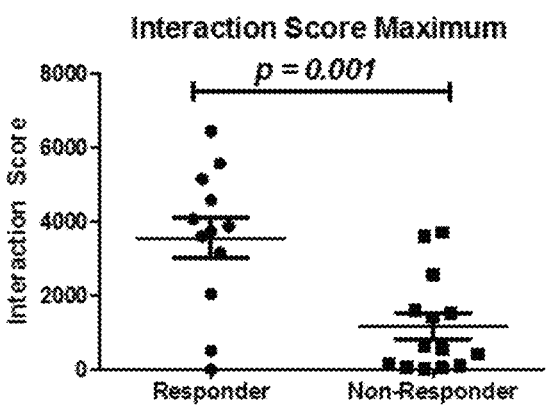

Alternatively, the interaction score was calculated for each individual field of view and the maximum score for each patient is shown in FIG. 12b. Based on the maximum score, a threshold of 1900 was selected to indicate likelihood of response to treatment.

Figure 13:
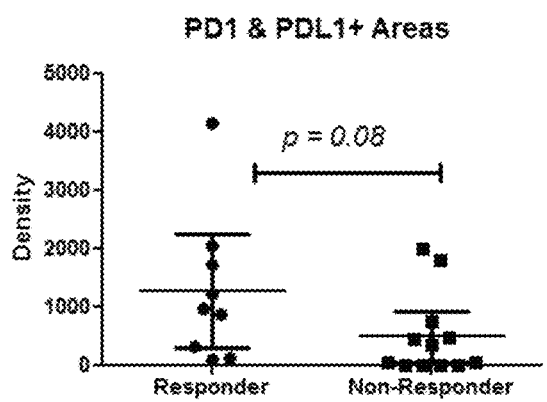
FIG. 13 shows analysis results based on whole-slide imaging in lieu of an enrichment algorithm.

To assess the effect of the enrichment algorithm on the interaction score, the above-mentioned procedures were performed using whole-slide imaging in lieu of the enrichment algorithm (see FIG. 13). When whole-slide image analysis was performed, there was no longer a statistically significant difference between the patients who responded to anti-PD therapy and those who did not. As such, a threshold could not be determined with this analysis.

Figure 14:
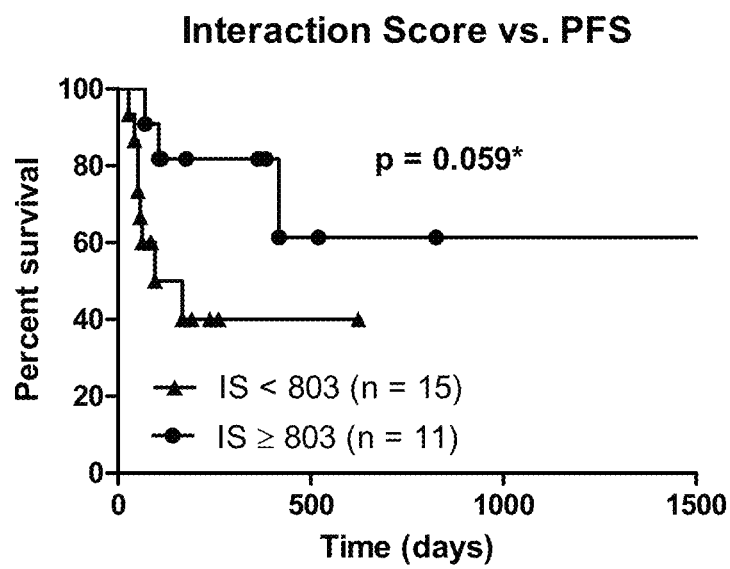
FIG. 14 shows a comparison of interaction scores with progression free survival of the 26 patients. Note: * indicates uncorrected log-rank test.

The interaction scores were compared with progression free survival (PFS) of the patients (FIG. 14). Interaction scores of at least 803 correlated well with survival. Notably, PD-L1 expression did not correlate with improved PFS (FIG. 15).

Figure 16:
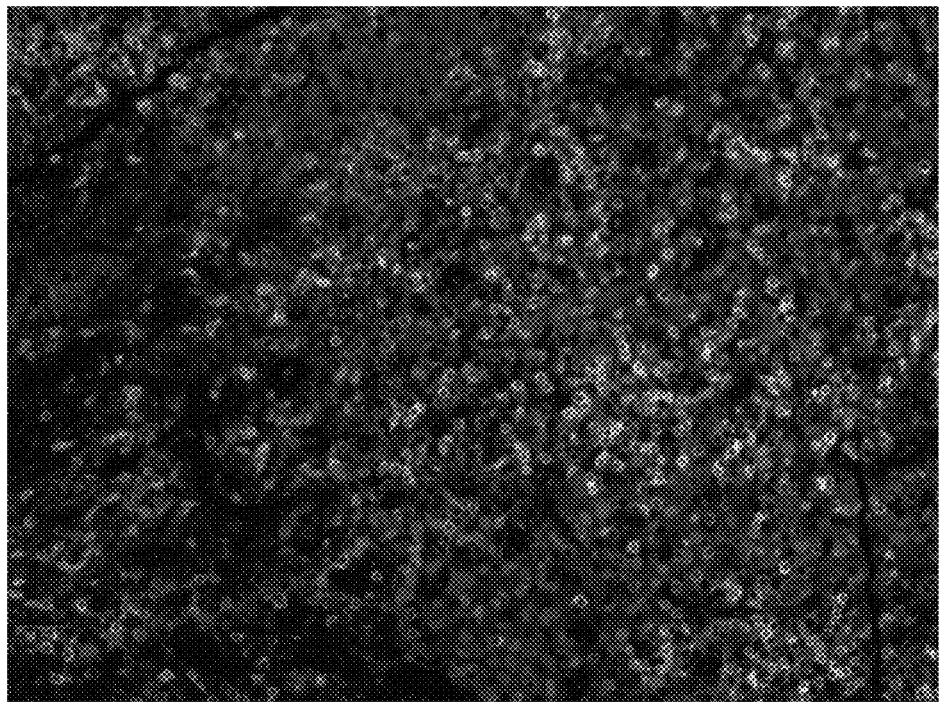
FIG. 16 shows a non-limiting example of a mask of fluorescence signals corresponding to PD-L1-positive cells (red), PD-1-positive cells (yellow), all tumor cells (green), and all cells (blue) for a positive responder to immunotherapy.
Figure 17:
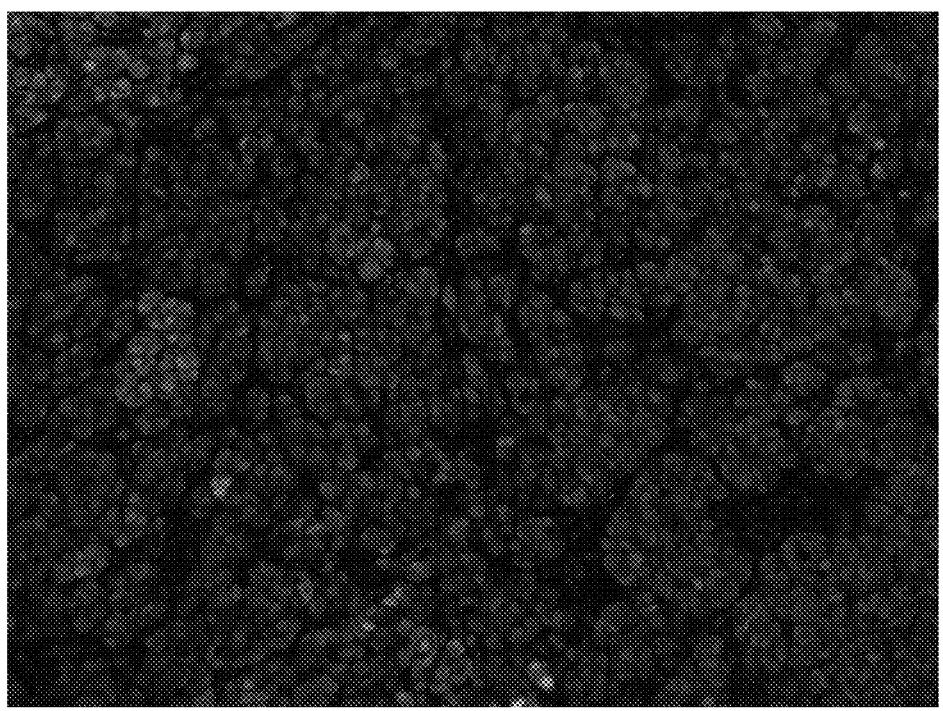
FIG. 17 shows a non-limiting example of a mask of fluorescence signals corresponding to PD-L1-positive cells (red), PD-1-positive cells (yellow), all tumor cells (green), and all cells (blue) for a negative responder to immunotherapy.

FIGS. 16 and 17 show a representative examples of overlaid masks indicating PD-L1-positive cells (red), PD-L-positive cells (yellow), tumor cells (S 100, green), and all cells (DAPI, blue). For a positive responder to immunotherapy, the mask in FIG. 16 readily indicates the presence of PD-L1-positive cells (red), PD-1-positive cells (yellow), and all tumor cells (green). In contrast, for a negative responder to immunotherapy, the mask in FIG. 17 indicates the presence of tumor cells (S100, green) and all cells (DAPI, blue), but shows little to no PD-L1-positive cells (red) or PD-1-positive cells (yellow). FIG. 16 represents an interaction score of 2176 (complete response to immunotherapy). FIG. 17 represents an interaction score of 8 (no response to immunotherapy).

Figure 19:
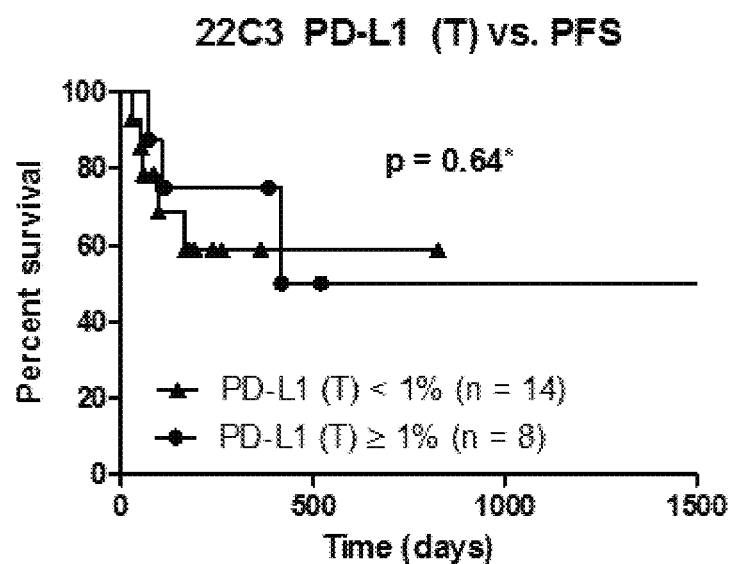
FIG. 19 shows a comparison of PD-L1 expression determined using the 22C3 FDA-approved IHC assay with progression free survival of the patients. Note: * indicates p-value was determined using uncorrected log-rank test.

The tissue samples were also assessed using an FDA-approved method to measure PD-L1 in non-small cell lung cancer with the anti-PD-L1 antibody clone 22C3, not currently used for melanoma tissue samples. PD-L1 expression was compared with patient PFS and is shown in FIG. 19. This method does not demonstrate statistically relevant diagnostic value compared to the methods described herein using interaction scores.

Figure 20A:
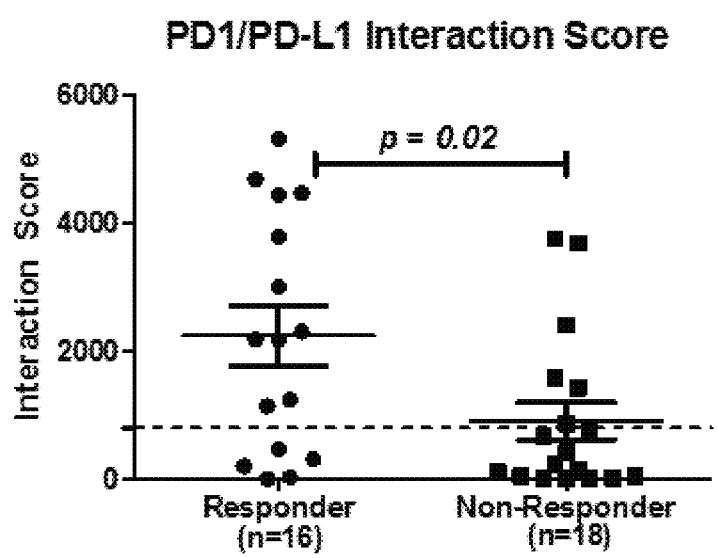
FIG. 20a shows a non-limiting example of interaction scores from 34 additional melanoma patients.
Figure 20B:
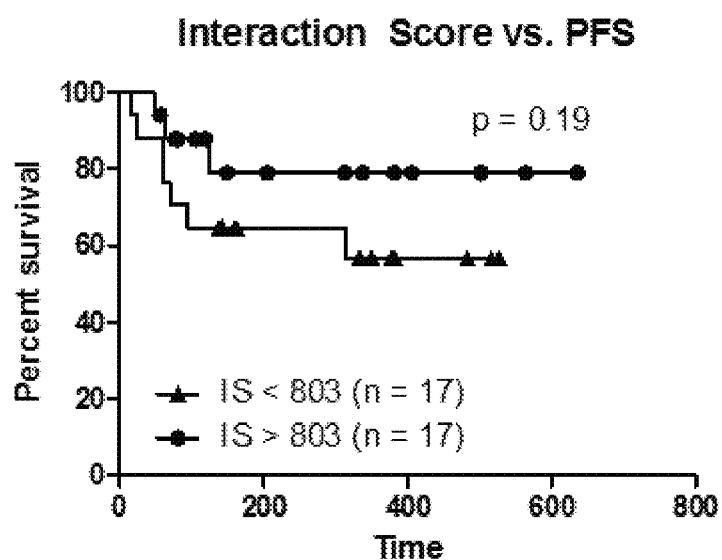

A verification cohort of 34 additional metastatic melanoma patients was examined and PD-1/PD-L1 interaction scores were obtained (see FIG. 20a). These interaction scores were also compared with progression free survival (PFS) of the patients (FIG. 20b). Although not statistically significant (p=0.19), the comparison indicates a trend of patients with higher PD-1/PD-L1 interaction scores having longer PFS. Statistical significance may be limited due to the relatively recent use of these therapies in the clinic therefore limiting the follow-up time. for these patients.

Figure 20C:
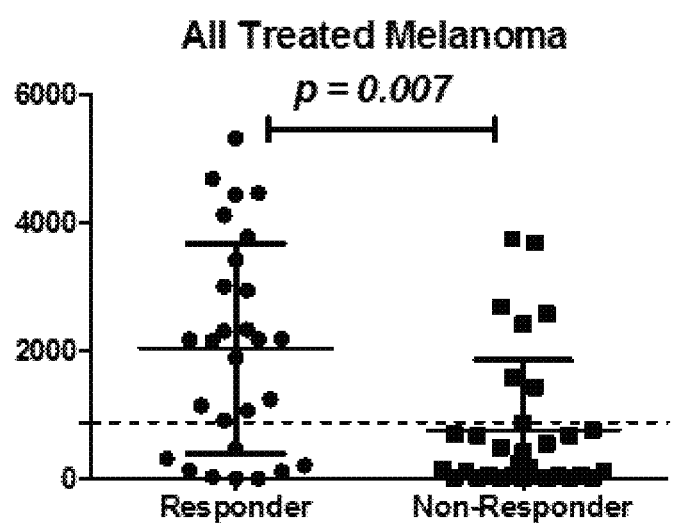
Figure 20D:
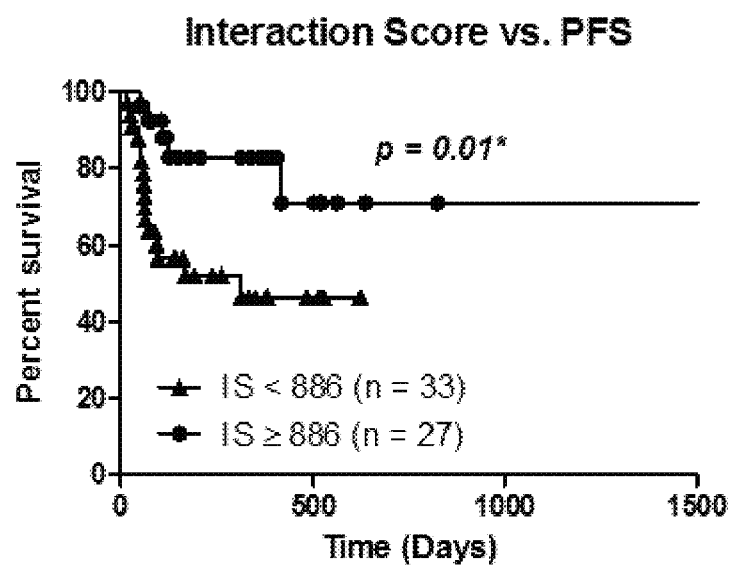
FIG. 20d shows a comparison of interaction scores with progression free survival of the patients of FIG. 20c. Note: * indicates the p-value was determined using uncorrected log-rank test.
Figure 20E:
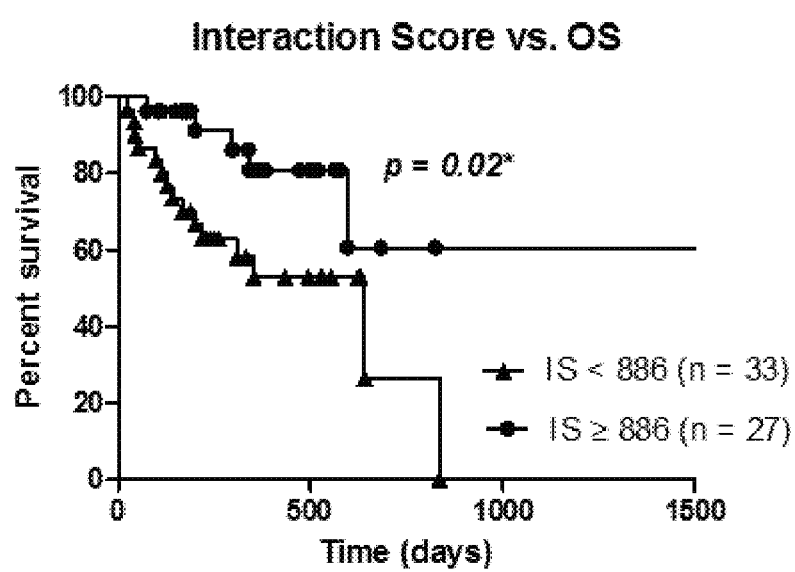
FIG. 20e shows a comparison of interaction scores with overall survival (OS) of the patients of FIG. 20c. Note: * indicates p-value was calculated using uncorrected log-rank test.

The PD-1/PD-L1 interaction scores as well as the comparison of these scores with patient PFS or patient overall survival (OS) for the combination of the earlier cohort of 26 patients with the verification cohort of 34 patients are shown in FIGS. 20c-20e. Combined analysis clearly indicate patients with high PD-1/PD-L1 demonstrate an improved response to anti-PD-1 therapies.

Figure 18:
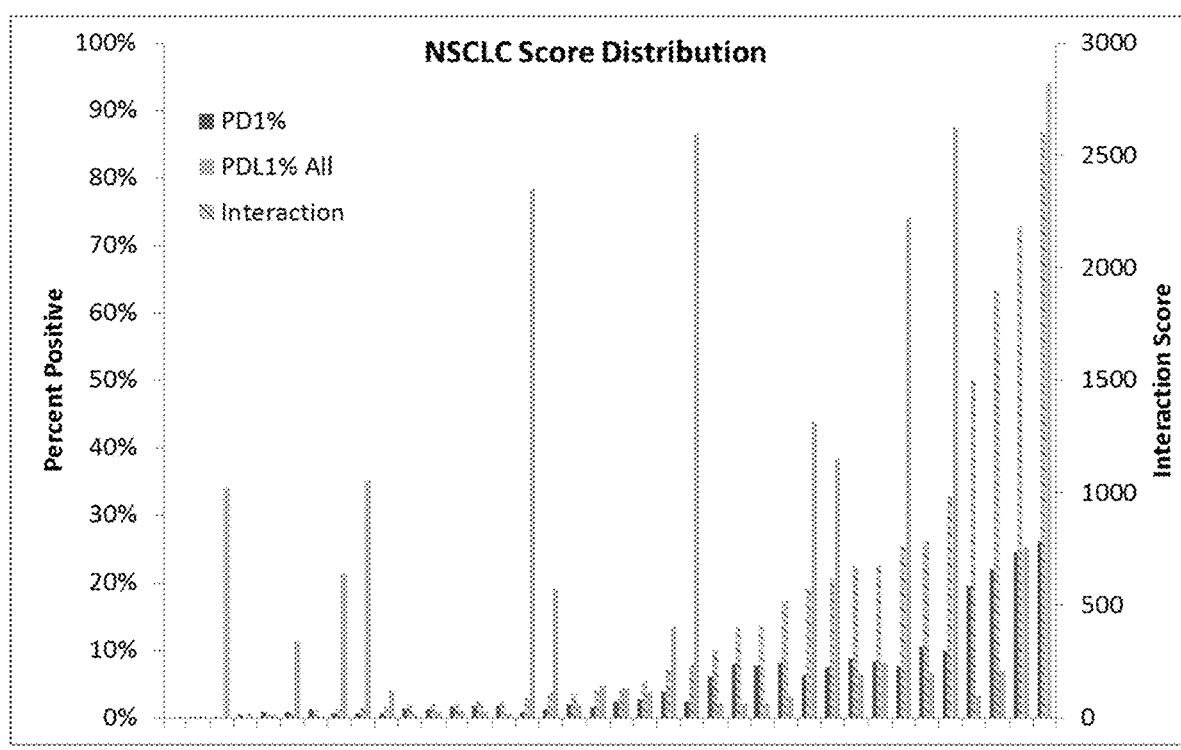
FIG. 18 shows representative PD-1/PD-L1 interaction scores and values of % biomarker positivity (PBP) for PD-L1 and PD-1 from 38 non-small cell lung cancer patients.

Example 2. Sample Preparation, Imaging, and Analysis of Imaging for Non-Small Cell Lung Carcinoma Tissue Samples from Human Patients Analogous procedures as Example 1 were performed, substituting the mouse anti-S1000) directly labeled with 488 dye with mouse anti-pan cytokeratin directly labeled with 488 dye for epithelial tumor samples. Interaction scores for 38 samples are shown in FIG. 18.

Example 3. Sample Preparation, Imaging, and Analysis of Imaging for Tissue Samples with Cells Expressing PD-L1 and Cells Expressing CD80

Sample Preparation

Formalin fixed paraffin embedded (FFPE) tissue samples were dewaxed, rehydrated and antigen retrieval was performed with elevated temperature conditions. Staining was then performed where the following steps were carried out. First, tissues were subjected to CTLA-4 expression detection using 20 pairs of hybridization probes spanning approximately 1 kb of the CTLA-4 mRNA using RNAScope® (Advanced Cell Diagnostics). In situ hybridization was visualized with TSA-Cy®3. The slides were washed and any residual HRP was then quenched using two washes of fresh 100 mM benzhydrazide with 50 mM hydrogen peroxide. The slides were again washed before staining with a mouse anti-CD80 primary antibody. Slides were washed and then incubated with an anti-mouse HRP secondary antibody. Slides were washed and then CD80 staining was detected using TSA-Cy® 5 (Perkin Elmer). Any residual HRP was then quenched using two washes of fresh 100 mM benzhydrazide with 50 mM hydrogen peroxide. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-AlexaFluor488® (Life Technologies). Slides were washed a final time before they were cover-slipped with mounting media and allowed to dry overnight at room temperature.

Figure 21:
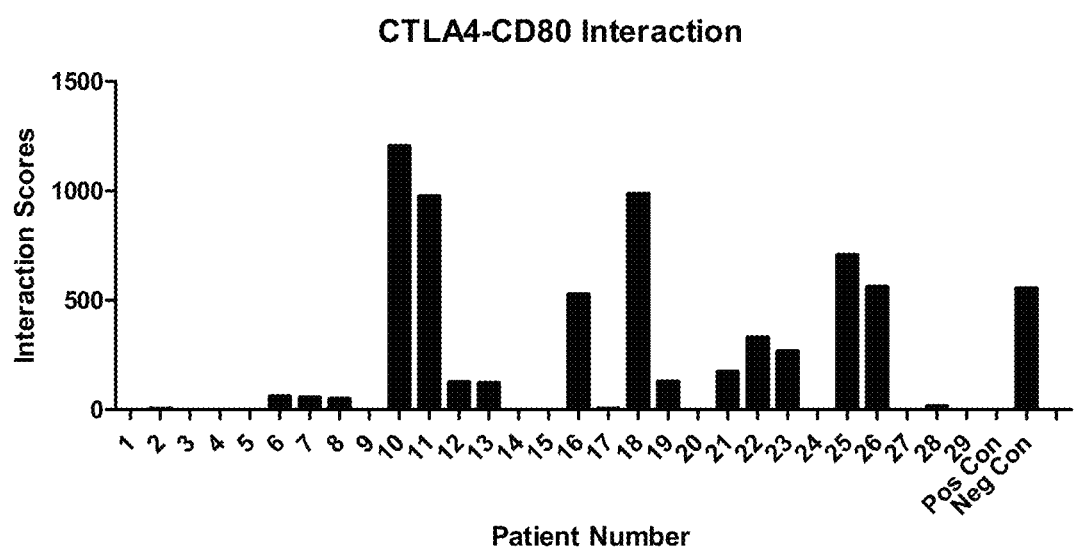
FIG. 21 shows a non-limiting example of CTLA-4/CD80 interaction scores from 29 metastatic melanoma patients.

Analogous imaging and analysis procedures as Example 1 were performed, imaging across DAPI, FITC, Cy® 3, and Cy® 5 wavelengths. Expression of CTLA-4 and CD80 was used to develop an enrichment algorithm for acquiring 20× images. Analysis was performed to determine CTLA-4/CD80 interaction scores by measuring the total area, in pixels, of CTLA-4 and CD3 positive cells within the proximity of CD80 positive cells divided by the total area, in pixels, of the CD3 positive cells, multiplied by a factor of 10,000. Results are shown in FIG. 21.

Example 4. Sample Preparation, Imaging, and Analysis of Imaging for Tissue Samples with Cells Expressing CTLA-4 and Cells Expressing CD80

Analogous procedures as Example 1 are performed, substituting the staining and analysis of PD-L1 and PD-1 with the staining and analysis of CTLA-4 and CD80.

Example 5. Sample Preparation, Imaging, and Analysis of Imaging for Tissue Samples with Cells Expressing PD-L2 and Cells Expressing PD-1

Analogous procedures as Example 1 are performed, substituting the staining and analysis of PD-L1 with the staining and analysis of PD-L2.

Example 6. Sample Preparation, Imaging, and Analysis of Imaging for Tissue Samples with Cells Expressing CTLA-4 and Cells Expressing CD86

Analogous procedures as Example 1 are performed, substituting the staining and analysis of PD-L1 and PD-1 with the staining and analysis of CTLA-4 and CD86.

Example 7. Sample Preparation, Imaging, and Analysis of Imaging for Tissue Samples with Cells Expressing LAG-3 and Cells Expressing HLA-DR Analogous procedures as Example 1 are performed, substituting the staining and analysis of PD-L1 and PD-1 with the staining and analysis of LAG-3 and HLA-DR.

Example 8. Sample Preparation, Imaging, and Analysis of Imaging for Tissue Samples with Cells Expressing TIM-3 and Cells Expressing Galectin 9

Analogous procedures as Example 1 are performed, substituting the staining and analysis of PD-L1 and PD-1 with the staining and analysis of TIM-3 and Galectin 9.

Example 9. Sample Preparation, Imaging, and Analysis of Imaging for Tissue Samples with Cells Expressing 41BB and Cells Expressing 4.1BBL Analogous procedures as Example 1 are performed, substituting the staining and analysis of PD-L1 and PD-1 with the staining and analysis of 41BB and 4.1BBL.

Example 10. Sample Preparation, Imaging, and Analysis of Imaging for Tissue Samples with Cells Expressing OX40 and Cells Expressing OX40L Analogous procedures as Example 1 are performed, substituting the staining and analysis of PD-L1 and PD-1 with the staining and analysis of OX40 and OX40L.

Example 11. Sample Preparation, Imaging, and Analysis of Imaging for Tissue Samples with Cells Expressing CD40 and Cells Expressing CD40L Analogous procedures as Example 1 are performed, substituting the staining and analysis of PD-L1 and PD-1 with the staining and analysis of CD40 and CD40L.

Example 12. Sample Preparation, Imaging, and Analysis of Imaging for Tissue Samples with Cells Expressing ICOS and Cells Expressing ICOSL Analogous procedures as Example 1 are performed, substituting the staining and analysis of PD-L1 and PD-1 with the staining and analysis of ICOS and ICOSL.

Example 13. Sample Preparation, Imaging, and Analysis of Imaging for Tissue Samples with Cells Expressing GITR and Cells Expressing GITRL Analogous procedures as Example 1 are performed, substituting the staining and analysis of PD-L1 and PD-1 with the staining and analysis of GITR and GITRL.

Example 14. Sample Preparation, Imaging, and Analysis of Imaging for Tissue Samples with Cells Expressing HLA-DR and Cells Expressing TCR Analogous procedures as Example 1 are performed, substituting the staining and analysis of PD-L1 and PD-1 with the staining and analysis of HLA-DR and TCR.

Example 15. Sample Preparation, Imaging, and Analysis of Imaging for Tissue Samples with Cells Expressing PD-1, PD-L1, and CD3

Figure 22:
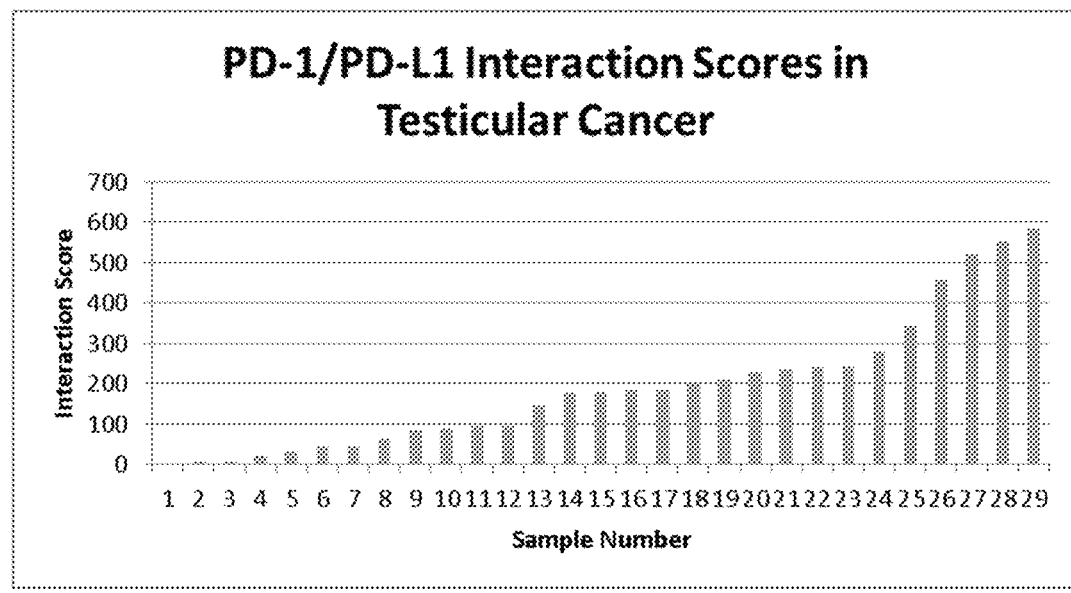
FIG. 22 shows a non-limiting example of PD-1/PD-L1 interaction scores from 29 patients with testicular carcinoma.

Analogous procedures as Example 1 were performed without the mouse anti-S100 antibody. Instead, after PD-L1 detection, primary and secondary antibodies were removed via microwave. Slides were then stained with rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected with TSA-AlexaFluor488 (Life Technologies). Imaging and analysis were analogous to Example 1 where the spatial proximity (e.g interaction score) was calculated by dividing the area of PD-1 positive cells in the PD-L1 positive area, measured in pixels, by the area of all nucleated cells, measured in pixels, multiplied by a factor of 10,000. Interaction scores for 29 samples are shown in FIG. 22.

Figure 23:
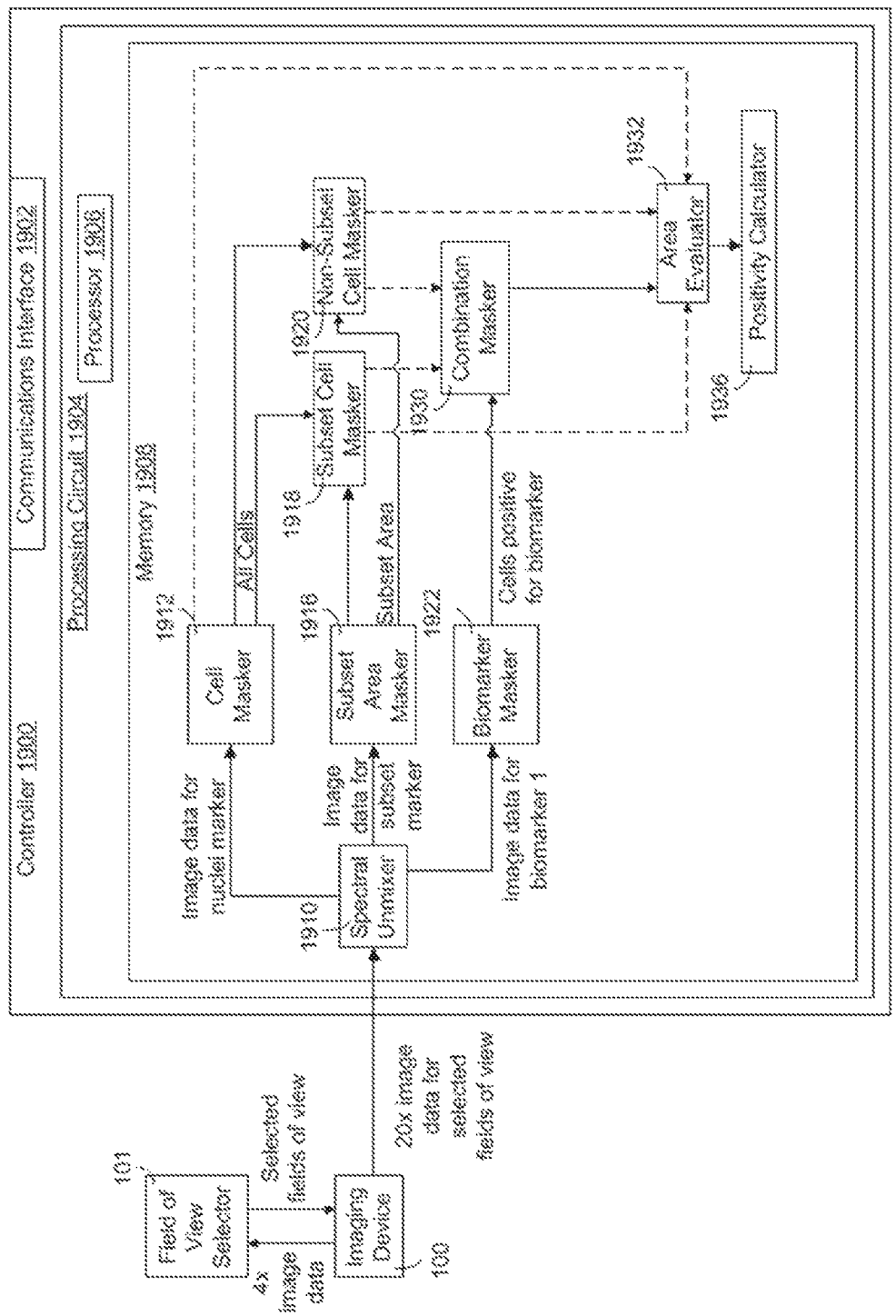
FIG. 23 shows is a block diagram of a controller configured to derive a value of biomarker positivity, according to an exemplary embodiment.

Manipulation of the image data from imaging device 100, for deriving a percent biomarker positivity value of the tissue sample, as described herein, may be carried out by controller 1900, shown schematically in FIG. 23. Controller 1900) is shown to include a communications interface 1902 and a processing circuit 1904. The processing circuit 1904 is configured to implement steps for determining percent biomarker positivity. It is contemplated that the elements and functions of controller 1900 may be included in controller 150 of imaging device 100, or may be present in a computing system separate from imaging device 100.

In some embodiments, the sample may be stained using a plurality of fluorescence tags with affinity for specific biomarkers. A digital image of the stained sample may be obtained, and the image further analyzed based on the location of the fluorescence tags. Rather than whole-image analysis, fields of view may be prioritized based on the number of cells that express a first biomarker of interest. A predetermined number of fields of view may then be further analyzed for fluorescence signals. In some embodiments, the images of fluorescence signals are manipulated to generate one or more masks of fluorescence signals corresponding to cells within the image. In some embodiments, the one or more masks of fluorescence signals comprise one or more selected from the group consisting of a mask of all cells within the image, a mask of all cells that express the subset biomarker (e.g., all tumor cells), within the image, a mask of all cells that do not express the subset biomarker (e.g., all non-tumor cells) within the image, a mask of all cells expressing a first biomarker of interest within the image, and a biomarker positive mask representing all cells of interest expressing a biomarker. The areas of these masks may be used to derive a value for PBP as desired. The total area of the biomarker mask may be used to calculate a percent biomarker positivity value by dividing the area of biomarker mask for the cell type of interest by the area of all cells in the compartment of interest.

Figure 24:
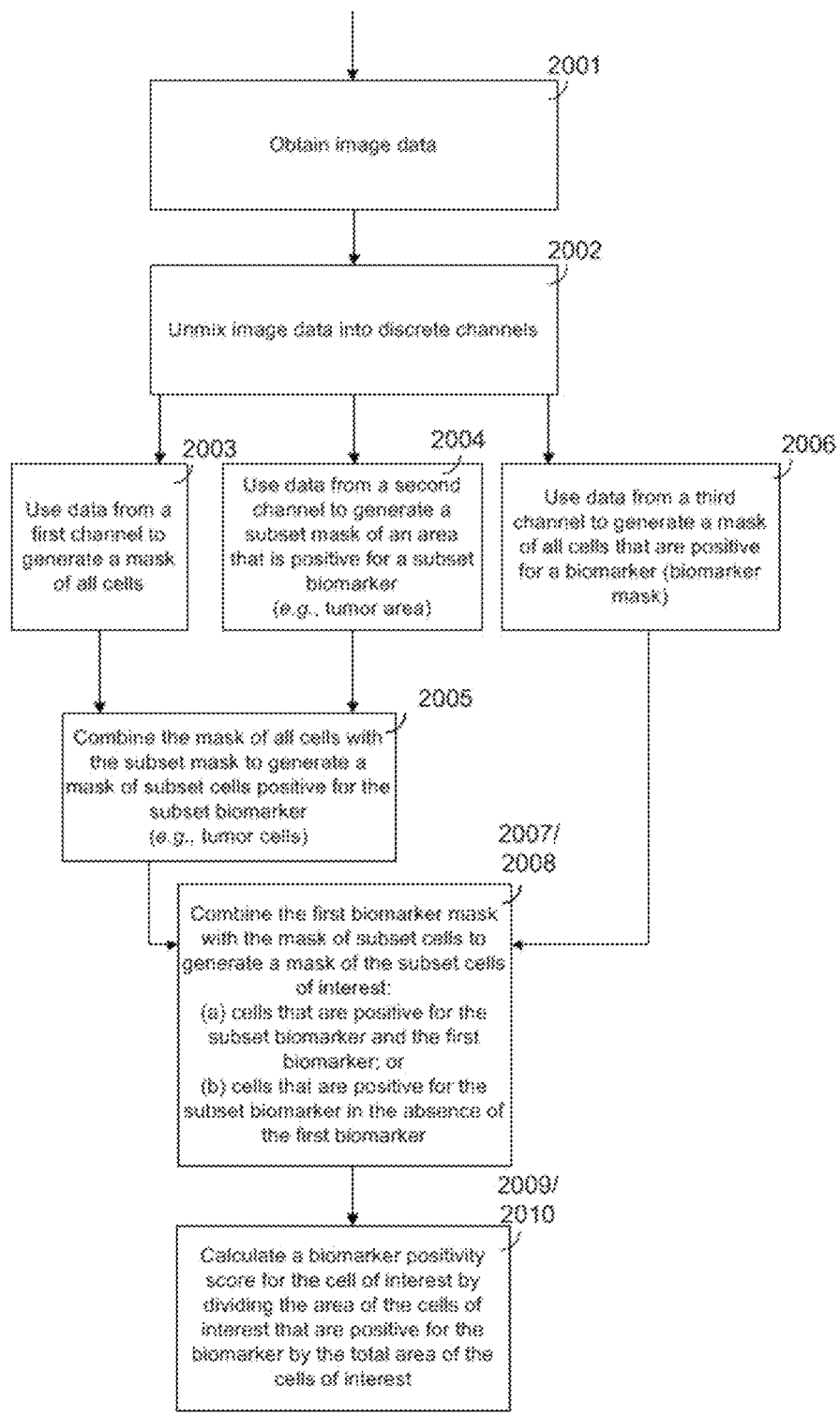
FIG. 24 shows is a flowchart of a process for deriving a value of biomarker positivity, according to an exemplary embodiment.

FIG. 24 is a flowchart depicting the steps of one embodiment of a method for deriving a value for % biomarker positivity (PBP). In step 2001, image data is obtained and in step 2002, the image data is unmixed such that data specific to various types of fluorescence signals are separated into different channels. In step 2003, data from a first channel is used to generate a mask of all cells. In step 2004, data from a second channel is used to generate a mask of the area in a field of view that expresses a subset biomarker, for example, this subset mask may be a mask of a tumor area present in a field of view. In step 2005, the all cell mask and the subset mask (e.g., a tumor area mask) are combined to generate a mask of all subset cells. In certain embodiments, combining the all cell mask and the subset mask may identify all tumor cells and/or all non-tumor cells.

In some embodiments, a subset of cells identified by a subset biomarker and a non-subset of cells corresponds to tumor cells and non-tumor cells, respectively or vice versa. In some embodiments, a subset of cells identified by a subset biomarker and a non-subset of cells corresponds to viable cells and non-viable cells, respectively or vice versa. In some embodiments, a subset of cells identified by a subset biomarker is a subset of viable cells and a non-subset of cells consists of the viable cells not included in the subset of viable cells. In some embodiments, a subset of cells identified by a subset biomarker and a non-subset of cells corresponds to T cells and non-T cells, respectively or vice versa. In some embodiments, a subset of cells identified by a subset biomarker and a non-subset of cells corresponds to myeloid cells and non-myeloid cells, respectively or vice versa.

The process may be carried out on only a selected type of cell of interest, for example, only tumor cells or only non-tumor cells. The process may also be directed to an analysis of both. In step 2006, data from a third channel is used to generate a mask of all cells that are positive for a biomarker (based on fluorescence signals representing the presence of a fluorescent tag with an affinity for binding to the particular biomarker of interest). In steps 2007 and 2008, the biomarker mask generated in step 2006 is combined with the subset cell mask generated in step 2005. Step 2007 combines the biomarker mask with the subset cell mask in a first manner, to generate a mask of all subset cells that are positive for the biomarker. Step 2008 combines the biomarker mask with the subset cell mask, in a second manner, to generate a mask of all subset cells that are not positive for the biomarker. One or both of steps 2007 and 2008 may be performed according the various embodiments of the method. In step 2009/2010, a PBP score is calculated by dividing the area of the subset cells of interest (e.g., the subset cells that are positive for the biomarker identified by the mask created in step 2007 or the subset cells that are not positive for the biomarker identified by the mask created in step 2008) by the total area of all cells of interest. Step 2009 calculates the PBP for subset cells that are positive for the biomarker. Step 2010 calculates the PBP for subset cells that are not positive for the biomarker. One or both of steps 2009 and 2010 may be performed according the various embodiments of the method.

Figure 25:
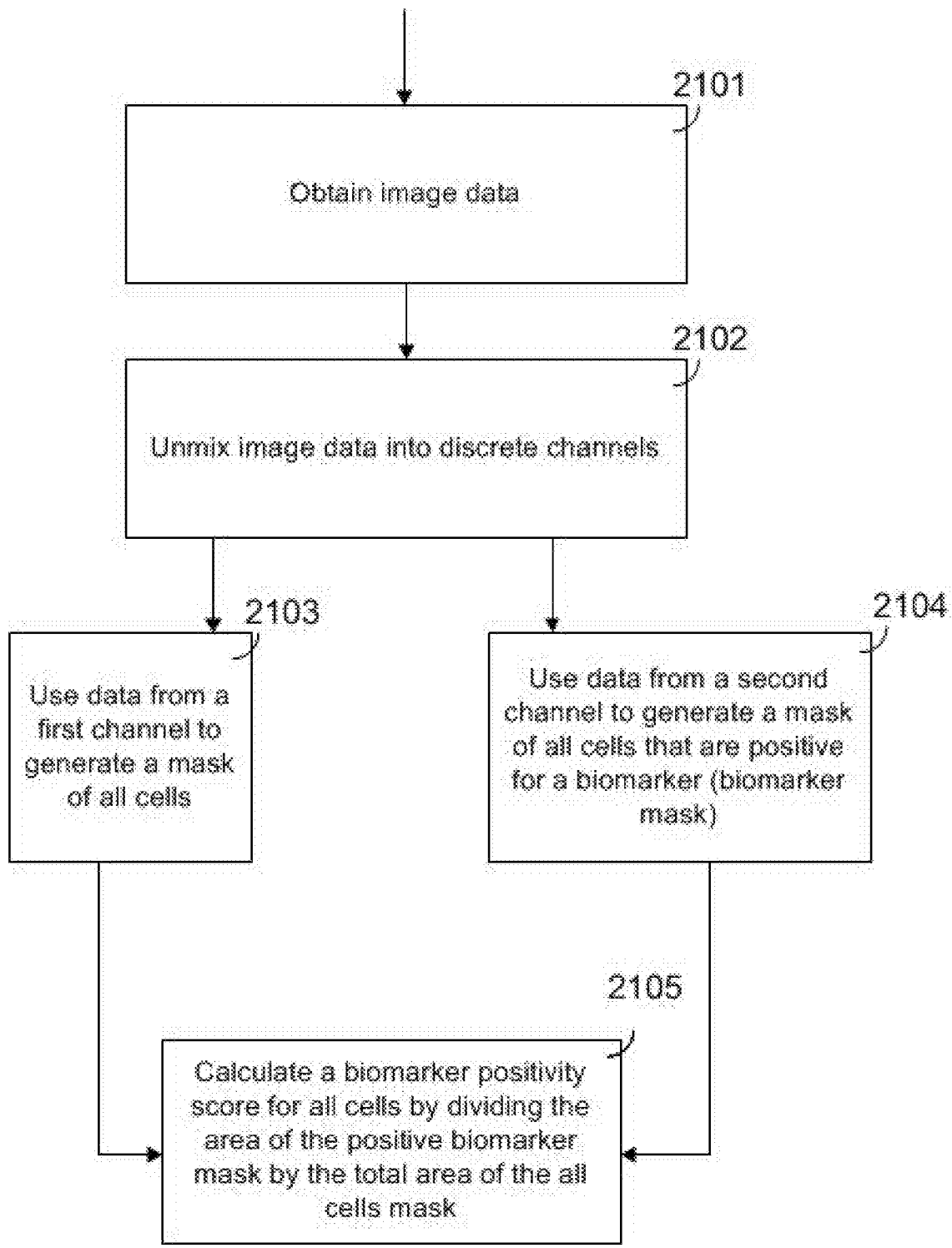
FIG. 25 shows is a flowchart of a process for deriving a value of biomarker positivity, according to a second exemplary embodiment.

FIG. 25 is a flowchart depicting the steps of a second embodiment of a method for deriving a value for % biomarker positivity (PBP). In step 2101, image data is obtained and in step 2102, the image data is unmixed such that data specific to various types of fluorescence signals are separated into different channels. In step 2103, data from a first channel is used to generate a mask of all cells. In step 2104, data from a second channel is used to generate a mask of all cells that are positive for a biomarker (based on fluorescence signals representing the presence of a fluorescent tag with an affinity for binding to the particular biomarker of interest). In step 2105, a PBP score is calculated by dividing the area of the cells that are positive for the biomarker (which is identified by the mask created in step 2104) by the total area of all cells of interest (from step 2103). The process of FIG. 25 may be carried out separately or concurrently with the method depicted in FIG. 24. In other words, a PBP score may be calculated for all cells, all tumor cells, and all non-tumor cells, or any combination thereof, may combining the methods of FIGS. 24 and 25.

In FIG. 23, controller 1900 is shown to include a communications interface 1902 and a processing circuit 1904. Communications interface 1902 may include wired or wireless interfaces (e.g., jacks, antennas, transmitters, receivers, transceivers, wire terminals, etc.) for conducting data communications with various systems, devices, or networks. For example, communications interface 1902 may include an Ethernet card and port for sending and receiving data via an Ethernet-based communications network and/or a WiFi transceiver for communicating via a wireless communications network. Communications interface 1902 may be configured to communicate via local area networks or wide area networks (e.g., the Internet, a building WAN, etc.) and may use a variety of communications protocols (e.g., BACnet, IP, LON, etc.). Communications interface 1902 may be a network interface configured to facilitate electronic data communications between controller 1900 and various external systems or devices (e.g., imaging device 100). For example, controller 1900 may receive imaging data for the selected fields of view from the imaging device 100, to analyze the data and calculate the percent biomarker positivity Processing circuit 1904 is shown to include a processor 1906 and memory 1908. Processor 1906 may be a general purpose or specific purpose processor, an application specific integrated circuit (ASIC), one or more field programmable gate arrays (FPGAs), a group of processing components, or other suitable processing components. Processor 506 may be configured to execute computer code or instructions stored in memory 508 or received from other computer readable media (e.g., CDROM, network storage, a remote server, etc.).

Memory 1908 may include one or more devices (e.g., memory units, memory devices, storage devices, etc.) for storing data and/or computer code for completing and/or facilitating the various processes described in the present disclosure. Memory 1908 may include random access memory (RAM), read-only memory (ROM), hard drive storage, temporary storage, non-volatile memory, flash memory, optical memory, or any other suitable memory for storing software objects and/or computer instructions. Memory 1908 may include database components, object code components, script components, or any other type of information structure for supporting the various activities and information structures described in the present disclosure. Memory 508 may be communicably connected to processor 1906 via processing circuit 1904 and may include computer code for executing (e.g., by processor 1906) one or more processes described herein.

Still referring to FIG. 23, controller 1900 is shown to receive input from an imaging device 100. The imaging device acquires all of the imaging data and records it, along with all of the meta-data which describes it. The imaging device will then serialize the data into a stream which can be read by controller 1900. The data stream may accommodate any binary data stream type such as the file system, a RDBM or direct TCP/IP communications. For use of the data stream, controller 1900 is shown to include a spectral unmixer 1910. The spectral unmixer 1910 may receive image data from an imaging device 100 on which it performs spectral unmixing to unmix an image presenting various wavelengths into individual, discrete channels for each band of wavelengths. For example, the image data may be "unmixed" into separate channels for each of the various fluorophores used to identify cells or proteins of interest in the tissue sample. The fluorophore, by way of example only, may be one or more of the group consisting of DAPI, Cy®2, Cy® 3, Cy®3.5, Cy® 5, FITC, TRITC, a 488 dye, a 555 dye, a 594 dye, and Texas Red. In one example, one of the channels may include image data that falls within a predetermined band surrounding a wavelength of 461 nm (the maximum emission wavelength for DAPI), to identify nuclei in the image. Other channels may include image data for different wavelengths to identify different portions of the tissue sample using different fluorophores.

Controller 1900 is also shown to include various maskers, such as cell masker 1912, subset area masker 1916, and biomarker masker 1922. These, or other maskers that may be included in the controller 1900 in other embodiments, are used to receive an unmixed signal from the spectral unmixer 1910 and create a mask for the particular cell or area of interest, dependent on the fluorophore used to identify certain features of interest in the tissue sample. To create a mask, the maskers (such as cell masker 1912, subset area masker 1916, and biomarker masker 1922) receive image data related to an intensity of each pixel in the field of view. Pixel intensity is directly proportional to the amount of fluorescence emitted by the sample, which in turn, is directly proportional to the amount of protein biomarker in the sample (when using a fluorophore to identify a particular biomarker). An absolute threshold may be set based on the values which exist in the image pixels. All the pixels which are greater than or equal to the threshold value will be mapped to 1.0, or "on", and all other pixels will be mapped to 0.0, or "off." In this way, a binary mask is created to identify the cell or tissue portion of interest in the field of view. In other embodiments, a mask is created using a lower bound wherein all pixels with an intensity at or above a lower bound are accepted and used as the pixel value for the mask. If the intensity is below the lower bound, the pixel value is set to 0.0, or "off".

Figure 26:
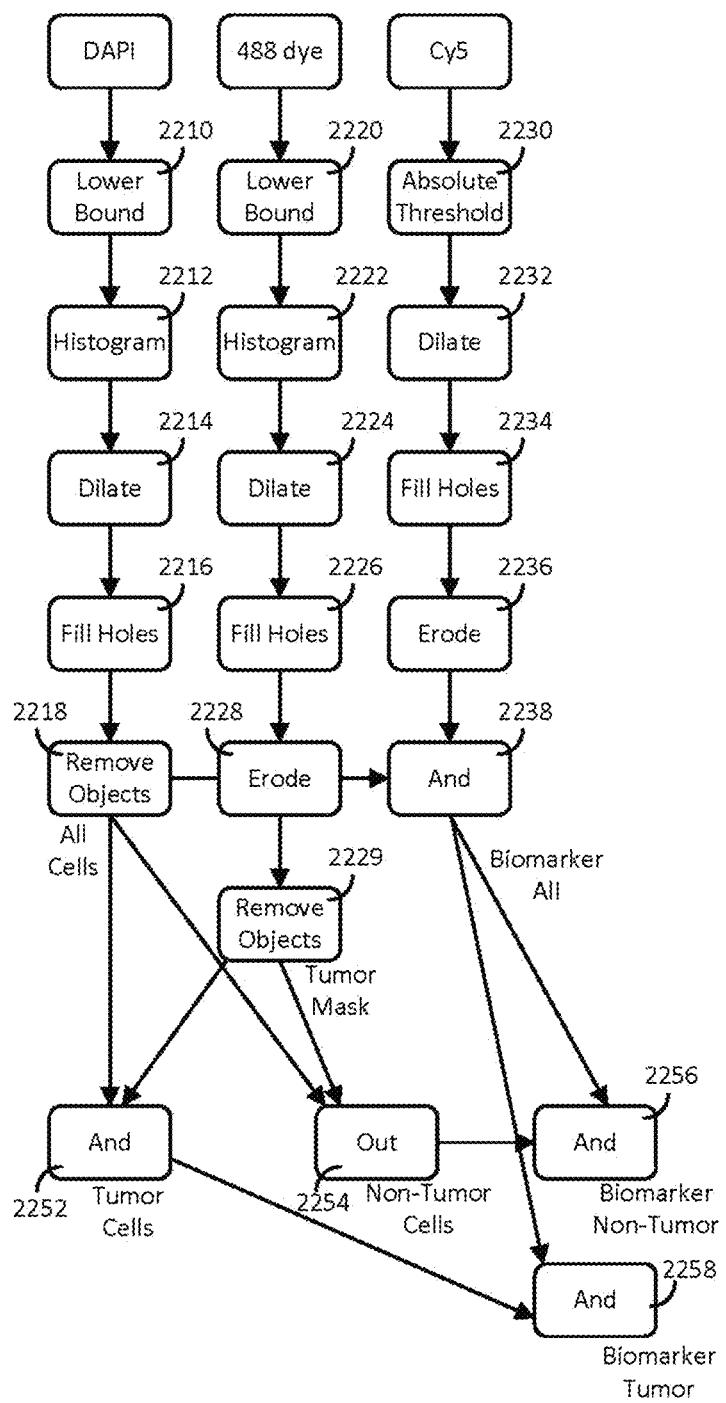
FIG. 26 shows is a flow diagram of the image processing steps used to derive a value of biomarker positivity, according to an exemplary embodiment.

In the example flow diagram for masking shown in FIG. 26, it is shown that the DAPI and 488 dye channels (or other fluorophore for identifying nuclei and tumor areas, respectively) use the lower bound protocol (steps 2210, 2212, 2220, 2222), while the Cy5 channel (or other fluorophore for identifying a biomarker of interest) uses a threshold value protocol (step 2230), for providing the mask output. In association with the lower bound protocol, there is also a histogram step to determine the lower bound. In particular, histogram threshold (step 2212, 2222) produces a threshold of an input image but uses a sliding scale to determine the point at which the thresholding occurs. The inputs are the current image and a user defined threshold percentage. The latter is used to determine at what percent of the total intensity the threshold level should be set. Firstly, the intensity of every pixel is summed into a total intensity. The threshold percentage is multiplied by this total intensity to obtain a cut-offsum. Finally, all pixels are grouped by intensity (in a histogram) and their intensities summed from lowest to highest (bin by bin) until the cut-off sum is achieved. The last highest pixel intensity visited in the process is the threshold for the current image. All pixels with intensities greater than that value have their intensities set to maximum while all others are set to the minimum.

The steps identified as steps 2214, 2216, 2224, 2226, 2228, 2232, 2234, 2236 in FIG. 26 represent intermediary steps that occur in the initial maskers, such as cell masker 1912 (steps 2214, 2216), subset area masker 1916 (steps 2224, 2226, 2228), and biomarker masker 1922 (steps 2232, 2234, 2236). These steps are defined as follows:

Dilate increases the area of brightest regions in an image. Two inputs are need for dilate. The first is the implicit current image and the second is the number of iterations to dilate. It is assumed that only binary images are used for the first input. The procedure will operate on continuous images, but the output will not be a valid dilate. The dilate process begins by first finding the maximum pixel intensity in the image. Subsequently, each pixel in the image is examined once. If the pixel under investigation has intensity equal to the maximum intensity, that pixel will be drawn in the output image as a circle with iterations radius and centered on the original pixel. All pixels in that circle will have intensity equal to the maximum intensity. All other pixels are copied into the output image without modification.

The fill holes procedure will fill "empty" regions of an image with pixels at maximum intensity. These empty regions are those that have a minimum intensity and whose pixel area (size) is that specified by the user. The current image and size are the two inputs required. Like dilate this procedure should only be applied to binary images.

Erode processes images in the same fashion as dilate. All functionality is the same as dilate except that the first step determines the minimum intensity in the image, only pixels matching that lowest intensity are altered, and the circles used to bloom the found minimum intensity pixels are filled with the lowest intensity value. Like dilate this procedure should only be applied to binary images.

Remove Objects.

Two inputs are expected: the current image and object size. Remove objects is the opposite of the fill holes procedure. Any regions containing only pixels with maximum intensity filling an area less than the input object size will be set to minimum intensity and thusly "removed." This procedure should only be applied to binary images; application to continuous images may produce unexpected results.

The output at steps 2218, 2229, and 2238 are the resultant cell mask, subset mask (or, in this particular example, tumor area mask), and biomarker cell mask, respectively. FIG. 26 further depicts the combinations of these resultant masks to obtain the relevant area information for the PBP score. These combinations are described below with reference to the combination maskers of the controller 1900, depicted in FIG. 23.

Controller 1900 is shown to include combination maskers, such as subset cell masker 1918, non-subset cell masker 1920, and combination masker 1930. In some embodiments, the subset cells identified by masker 1918 and the non-subset cells identified by masker 1920 are tumor cells and non-tumor cells, respectively. In some such embodiments, the subset cell masker 1918 is a tumor masker and the non-subset cell masker 1920 is a non-tumor masker. Subset cell masker performs an And operation, as shown at step 2252 in FIG. 26, to combine the output of the cell masker 1912 (representative of all cells in the image) with the output of the subset area masker 1916. Accordingly, subset cell masker generates a mask of all subset cells in the image. This same combination, using an Out operation performed by non-subset cell masker 1920 as shown at step 2254 in FIG. 26, generates a mask of all non-subset cells in the sample image.

Combination masker 1930 is configured to combine two input masks. As depicted in FIG. 26, combination masker 1930 combines the biomarker mask with one of the subset cell mask (from subset cell masker 1918) or non-subset cell mask (from non-subset cell masker 1920), or both biomarker mask+subset mask and biomarker mask+non-subset mask. The dotted lines represent that either one or both of the cell masks may be combined with the biomarker mask at combination masker 1930. The result of the combination masker 1930 is a mask representative of all subset cells that are positive for the biomarker and/or all non-subset cells that are positive for the biomarker. The combination masker 1930 may combine the masks in an alternate manner such that the result of the combination masker 1930 is a mask representative of subset cells that are not positive for the biomarker (i.e., biomarker negative). If the cells of interest are not specifically related to the subset, for example tumor or non-tumor, but rather, all cells, then the biomarker positive mask is not combined with any additional mask and passes through the combination masker 1930 without modification.

To calculate the % biomarker positivity score (PBP), the area of the selected subset cell (e.g., all, tumor, or non-tumor) biomarker positive mask or biomarker negative mask (in which case the score represents biomarker negativity) is determined in pixels at the area evaluator 1932. The total area of all the selected cells (positive and not positive for the biomarker), is determined in pixels at the area evaluator 1932. The dotted lines terminating at area evaluator 1932 indicate that the total area inputs may be one or more of the all cell mask, the subset cell mask, and the non-subset mask, to be calculated separately. A percent biomarker positivity score is determined at the positivity calculator 1936. In one embodiment, the BPB score is calculated by dividing the area of the selected cell biomarker positive mask from area evaluator 1932 by the area of the all selected cell mask from area evaluator 1932, and multiplying 100. In one embodiment, the equation executed by the interaction calculator 1936 is:

$$BPB = \frac{A_P}{A_A} \times 100$$

wherein $A_P$ is a biomarker positive area for the selected type of subset cell (e.g., all, tumor, or non-tumor) and $A_A$ is the total area of all cells of the selected cell type (all, tumor, non-tumor). In some embodiments, $A_N$ replaces $A_P$ in the above equation, wherein $A_N$ is a biomarker negative area for the selected type of cell (e.g., all, tumor, or non-tumor), to determine a score representative of percent biomarker negativity for the type of subset cell.

The And procedure is modeled after a binary AND operation, but differs in significant ways. And accepts the current image and a user selected resultant. The output is an image created by performing a multiplication of the normalized intensities of matching pixels from the two input images. In some cases, image intensity data is already normalized. Therefore, the And procedure is simply a pixel-wise multiplication of the two images. The two inputs required for Out are the current image and a user selected resultant. Out removes the second image form the first according to the formula $A*(1-B/B_{max})$ where A is the current image, B the user selected image to remove, and $B_{max}$ is the maximum intensity of B. Note that the division of B by $B_{max}$ normalizes B.

In some embodiments, provided herein is an imaging system for deriving a value for % biomarker positivity (PBP) for all cells or, optionally, one or more subsets thereof, present in a field of view of a tissue sample taken from a cancer patient, the imaging system comprising an imaging apparatus comprising a stage for positioning the sample in an imaging field, an electromagnetic radiation source for directing electromagnetic radiation at the sample, and a detector configured to detect electromagnetic radiation from the sample, and a controller. The controller comprises a user interface for exchanging information between an operator and the electronic control system and a processing circuit configured to execute instructions stored on a computer-readable medium. The instructions cause the electronic control system of the imaging system to: (i) receive information about the detected electromagnetic radiation from the imaging apparatus; (ii) generate image data based on the detected electromagnetic radiation; and (iii) analyze the image data to derive a value for PBP for all cells or, optionally, one or more subsets thereof present in a field of view.

In some embodiments, analyzing the data comprises:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a subset biomarker;
(iii) optionally, constructing a third mask of third fluorescence signals representative of all areas present in the field of view, which express a first biomarker of interest;
(iv) combining said first and second masks in a manner that provides a fourth mask comprising fluorescence signals representative of all cells in the field of view, which also express the subset biomarker;
(v) optionally, combining said first and third masks in a manner that provides a fifth mask comprising fluorescence signals representative of a first subset of all cells in the field of view, which also express the first biomarker of interest;
(vi) deriving a value for PBP for all cells expressing the subset biomarker by dividing the total area of the fourth mask by the total area of the first mask;
(vii) optionally, combining said fourth and fifth masks in a manner that provides a sixth mask comprising fluorescence signals representative of the first subset of all cells in the field of view, which express the subset biomarker and the first biomarker of interest; and
(viii) optionally, deriving a value for PBP for the first subset of all cells expressing the subset biomarker and the first biomarker of interest by dividing the total area of the sixth mask by the total area of the fourth mask.

In some embodiments, analyzing the data comprises:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a subset biomarker;
(iii) optionally, constructing a third mask of third fluorescence signals representative of all areas present in the field of view, which express a first biomarker of interest;
(iv) combining said first and second masks in a manner that provides a fourth mask comprising fluorescence signals representative of all cells in the field of view, which also express the subset biomarker;
(v) optionally, combining said first and third masks in a manner that provides a fifth mask comprising fluorescence signals representative of all cells in the field of view, which also express the first biomarker of interest;
(vi) deriving a value for PBP for all cells expressing the subset biomarker by dividing the total area of the fourth mask by the total area of the first mask;
(vii) optionally, combining said fourth and fifth masks in a manner that provides a sixth mask comprising fluorescence signals representative of all cells in the field of view, which
  (a) express the subset biomarker and the first biomarker of interest: or
  (b) express the subset biomarker in the absence of the first biomarker of interest;
and
(viii) optionally, deriving a value for PBP for the first subset of all cells which either (a) express the subset biomarker and the first biomarker of interest or (b) express the subset biomarker in the absence of the first biomarker of interest, by dividing the total area of the sixth mask by the total area of the fourth mask.

In some embodiments, the optional steps are not performed. In some embodiments, all the recited optional steps are performed. In some embodiments, the total area is measured in pixels. In some embodiments, the total area of the fourth mask and the total area of the first mask are each measured in pixels. In some embodiments, the total area of the sixth mask and the total area of the fourth mask are each measured in pixels. In some embodiments, the total area of the first mask, the total area of the fourth mask, and the total area of the sixth mask are each measured in pixels. In some embodiments, a pixel is 0.5 μm wide.

In some embodiments, analyzing the data further comprises:
(ix) constructing a seventh mask of fourth fluorescence signals representative of all areas present in the field of view, which express a second biomarker of interest;
(x) combining said first and seventh masks in a manner that provides an eighth mask comprising fluorescence signals representative of a second subset of all cells in the field of view, which also express the second biomarker of interest;
(xi) combining said fourth and eighth masks in a manner that provides a ninth mask comprising fluorescence signals representative of the second subset of all cells in the field of view, which express the subset biomarker and the second biomarker of interest; and
(xii) deriving a value for PBP for the second subset of all cells expressing the subset biomarker and the second biomarker of interest by dividing the total area of the ninth mask by the total area of the fourth mask.

In some embodiments, the total area is measured in pixels. In some embodiments, the total area of the ninth mask and the total area of the fourth mask are each measured in pixels. In some embodiments, a pixel is 0.5 μm wide.

In some embodiments, analyzing the data further comprises:
(ix) constructing a seventh mask of fourth fluorescence signals representative of all areas present in the field of view, which express a second biomarker of interest;

(x) subtracting said second mask from said first mask in a manner that provides an eighth mask comprising fluorescence signals representative of all cells that do not express the subset biomarker in the field of view;
(xi) combining said seventh and eighth masks in a manner that provides a ninth mask comprising fluorescence signals representative of all cells that express the second biomarker of interest but do not express the subset biomarker in the field of view; and
(xii) deriving a value for PBP for all cells that express the second biomarker of interest but do not express the subset biomarker by dividing the total area of the ninth mask by the total area of the eighth mask.

In some embodiments, the method further comprises:
(ix) constructing a seventh mask of fourth fluorescence signals representative of all areas present in the field of view, which express a second biomarker of interest;
(x) combining said sixth and seventh masks in a manner that provides an eighth mask comprising fluorescence signals representative of all cells that
  (a) express the subset biomarker, the first biomarker of interest, and the second biomarker of interest in the field of view;
  (b) express the subset biomarker and the first biomarker of interest in the absence of the second biomarker of interest in the field of view; or
  (c) express the subset biomarker and the second biomarker of interest in the absence of the first biomarker of interest in the field of view:
and
(xii) deriving a value for PBP for all cells that express the first biomarker of interest or the second biomarker of interest, or a combination thereof, as well as the subset biomarker, by dividing the total area of the eighth mask by the total area of the fourth mask.

In some embodiments, the method further comprises additional cycles of steps analogous to steps (ix), (x), and (xii) with respect to one or more additional biomarkers of interest (e.g., a third biomarker of interest).

In some embodiments, the total area is measured in pixels. In some embodiments, the total area of the ninth mask and the total area of the eighth mask are each measured in pixels. In some embodiments, a pixel is 0.5 µm wide.

In another aspect, provided herein are methods of deriving a value for % biomarker positivity (PBP) for all tumor cells present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a tumor biomarker;
(iii) combining said first and second masks in a manner that provides a third mask comprising fluorescence signals representative of all tumor cells in the field of view;
(iv) constructing a fourth mask of third fluorescence signals representative of all areas present in the field of view, which express a biomarker of interest;
(v) combining said third and fourth masks in a manner that provides a fifth mask comprising fluorescence signals representative of all tumor cells in the field of view, which also express the biomarker of interest; and
(vi) deriving a value for PBP for all tumor cells expressing the biomarker of interest by dividing the total area of the fifth mask by the total area of the third mask.

In some embodiments, the total area is measured in pixels. In some embodiments, the total area of the fifth mask and the total area of the third mask are each measured in pixels. In some embodiments, a pixel is 0.5 µm wide. In some embodiments, the biomarker of interest comprises a biomarker selected from the group consisting of PD-L1, Galectin 9, and MHC. In some embodiments, the biomarker of interest comprises PD-L1. In some embodiments, the biomarker of interest comprises Galectin 9. In some embodiments, the biomarker of interest comprises MHC. In some embodiments, the field of view further comprises non-tumor cells. In some embodiments, the non-tumor cells comprise immune cells and stromal cells.

In another aspect, provided herein are methods of deriving a value for % biomarker positivity (PBP) for all non-tumor cells present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a tumor biomarker;
(iii) subtracting said second mask from said first mask in a manner that provides a third mask comprising fluorescence signals representative of all non-tumor cells in the field of view;
(iv) constructing a fourth mask of fluorescence signals representative of all areas present in the field of view, which express a biomarker of interest;
(v) combining said third and fourth masks in a manner that provides a fifth mask comprising fluorescence signals representative of all non-tumor cells in the field of view, which also express the biomarker of interest; and
(vi) deriving a value for PBP for all non-tumor cells expressing the biomarker of interest by dividing the total area of the fifth mask by the total area of the third mask.

In some embodiments, the first subset of all the cells in the field of view comprises tumor cells. In some embodiments, the first subset of all the cells in the field of view comprises non-tumor cells. In some embodiments, the first subset of all the cells in the field of view comprises non-tumor and tumor cells.

In some embodiments, a subset of cells and a non-subset of cells corresponds to tumor cells and non-tumor cells, respectively or vice versa. In some embodiments, a subset of cells and a non-subset of cells corresponds to viable cells and non-viable cells, respectively or vice versa. In some embodiments, a subset of cells is a subset of viable cells and a non-subset of cells consists of the viable cells not included in the subset of viable cells. In some embodiments, a subset of cells and a non-subset of cells corresponds to T cells and non-T cells, respectively or vice versa. In some embodiments, a subset of cells and a non-subset of cells corresponds to myeloid cells and non-myeloid cells, respectively or vice versa.

In some embodiments, the first subset of all the cells in the field of view comprises T-cells. In some embodiments, the T-cells express CD3. In some embodiments, the T-cells express CD8. In some embodiments, the T-cells express CD4.

In some embodiments the first subset of all the cells in the field of view comprises myeloid cells. In further embodiments the myeloid cells are myeloid derived suppressor cells. In further embodiments the myeloid cells are tumor associated macrophages. In some embodiments, the subset biomarker is expressed only in tumor cells. In some embodiments, the subset biomarker is expressed only in non-tumor cells. In some embodiments, the subset biomarker is expressed in T-cells. In some embodiments, the subset biomarker comprises CD3. In some embodiments, the subset biomarker comprises CD19. In some embodiments, the subset biomarker is expressed in myeloid cells. In some embodiments, the subset biomarker is expressed in myeloid derived suppressor cells. In some embodiments, the subset biomarker is expressed in tumor associated macrophages. In some embodiments, the first biomarker of interest comprises Ki67 and said first subset of all the cells in the field of view comprises CD8 positive cells.

In some embodiments, the first biomarker of interest comprises a biomarker selected from the group consisting of CD11b, CD33, HLA-DR, IDO-1, ARG1, granzyme B, PD-L1, PD-L2, B7-H3, B7-H4, HLA-DR. Galectin 9, CD80, CD86, 4.1BBL, ICOSL. CD40, OX40L, IDO-1, GITRL, PD-1, TIM3, LAG3, 41BB, OX40, CTLA-4, CD40L, CD28, GITR, ICOS, CD28, CD3, CD4. CD8, FoxP3, CD25, CD16, CD56, CD68, CD163, CD80, and CD86. In some embodiments, the first biomarker of interest comprises a biomarker selected from the group consisting of PD-L1, PD-L2, B7-H3. B7-H4, HLA-DR, Galectin 9, CD80, CD86, 4.1BBL, ICOSL, CD40, OX40L, IDO-1, GITRL, ICOS, CD28, CD4, CD8, FoxP3, CD25, CD16. CD56, CD68. CD163, CD80, and CD86. In some embodiments, the first biomarker of interest comprises a biomarker selected from the group consisting of PD-L1, PD-L2, B7-H3, B7-H4, HLA-DR, Galectin 9, CD80, CD86, 4.1 BBL, ICOSL, CD40, OX40L, IDO-1, and GITRL. In some embodiments, the first biomarker of interest comprises a biomarker selected from the group consisting of PD-L1, Galectin 9, and MHC In some embodiments, the first biomarker of interest comprises PD-L1.

In some embodiments, the second biomarker of interest comprises a biomarker selected from PD-1, TIM-3, and TCR. In some embodiments, the second biomarker of interest comprises PD-1.

In some embodiments, the first biomarker of interest and the second biomarker of interest are different from each other and comprise a biomarker selected from the group consisting of PD-L1, PD-L2, B7-H3, B7-H4, HLA-DR, Galectin 9, CD80. CD86, 4.1BBL, ICOSL, CD40, OX40L, IDO-1, GITRL, ICOS, CD28, CD3, CD4, CD8. FoxP3, CD25, CD16, CD56, CD68, CD163, CD80, and CD86. In some embodiments, the first biomarker of interest and the second biomarker of interest are different from each other and comprise a biomarker selected from the group consisting of CD11b, CD33, HLA-DR. IDO-1, ARG1, granzyme B, PD-L, PD-L2, B7-H3, B7-H4, HLA-DR. Galectin 9. CD80, CD86, 4.1BBL, ICOSL, CD40, OX40L, IDO-1, GITRL, ICOS, CD28, CD3, CD4. CD8, FoxP3, CD25, CD16, CD56, CD68, CD163, CD80, and CD86.

In some embodiments, the first biomarker of interest comprises a biomarker selected from the group consisting of PD-L1, PD-L2. B7-H3, B7-H4, HLA-DR, Galectin 9, CD80, CD86, 4.1BBL. ICOSL, CD40. OX40L, IDO-1, GITRL, ICOS, CD28, CD4, CD8, FoxP3, CD25, CD16, CD56, CD68, CD163, CD80, and CD86; and the second biomarker of interest comprises a biomarker selected from PD-1, TIM-3, and TCR. In some embodiments, the first biomarker of interest comprises PD-L1 and the second biomarker of interest comprises PD-1. In some embodiments, the first biomarker of interest comprises PD-L1 and the second biomarker of interest comprises CD80. In some embodiments, the first biomarker of interest comprises CTLA-4 and the second biomarker of interest comprises CD80. In some embodiments, the first biomarker of interest comprises PD-L2 and the second biomarker of interest comprises PD-1. In some embodiments, the first biomarker of interest comprises CTLA-4 and the second biomarker of interest comprises CD86. In some embodiments, the first biomarker of interest comprises LAG-3 and the second biomarker of interest comprises HLA-DR. In some embodiments, the first biomarker of interest comprises TIM-3 and the second biomarker of interest comprises Galectin 9. In some embodiments, the first biomarker of interest comprises 41BB and the second biomarker of interest comprises 4.1BBL. In some embodiments, the first biomarker of interest comprises OX40 and the second biomarker of interest comprises OX40L. In some embodiments, the first biomarker of interest comprises CD40 and the second biomarker of interest comprises CD40L. In some embodiments, the first biomarker of interest comprises ICOS and the second biomarker of interest comprises ICOSL. In some embodiments, the first biomarker of interest comprises GITR and the second biomarker of interest comprises GITRL. In some embodiments, the first biomarker of interest comprises HLA-DR and the second biomarker of interest comprises TCR. In some embodiments, the first biomarker of interest comprises CD25 and the second biomarker of interest comprises FoxP3. In some embodiments, the first biomarker of interest comprises CD4 and the second biomarker of interest comprises CD8. In some embodiments, the first biomarker of interest comprises CD3 and the second biomarker of interest comprises PD-1. In some embodiments, the first biomarker of interest comprises CD56 and the second biomarker of interest comprises CD16. In some embodiments, the first biomarker of interest comprises HLA-DR and the second biomarker of interest comprises IDO-1. In some embodiments, the first biomarker of interest comprises CD33 and the second biomarker of interest comprises ARG1.

In some embodiments, the subset biomarker is only expressed in tumor cells. In some embodiments, the subset biomarker is expressed only in non-tumor cells. In some embodiments, the subset biomarker is expressed in T-cells. In some embodiments, the subset biomarker comprises CD3. In some embodiments, the subset biomarker comprises CD19. In some embodiments, the subset biomarker comprises CD45. In some embodiments, the subset biomarker is expressed in myeloid cells. In some embodiments, the subset biomarker comprises CD11b.

In some embodiments, the first biomarker of interest comprises Ki67 and the first subset of all the cells in the field of view comprises CD8 positive cells.

In some embodiments, the non-tumor cells comprise immune cells and stromal cells. In some embodiments, the non-tumor cells comprise myeloid cells.

In some embodiments, the fluorescence signals are from four fluorescence tags, each specific to a different biomarker. In further embodiments, a first fluorescence tag is associated with the first biomarker of interest, a second fluorescence tag is associated with the second biomarker of interest, a third fluorescence tag is associated with a third biomarker of interest, and a fourth fluorescence tag is associated with a fourth biomarker of interest. In some embodiments, the first biomarker of interest comprises a tumor and non-tumor marker. In some embodiments, the second biomarker of interest comprises a non-tumor marker. In some embodiments, the first biomarker of interest comprises a tumor and non-tumor marker, and the second biomarker of interest comprises a non-tumor marker. In some embodiments, the third biomarker of interest is expressed by all cells. In some embodiments, the fourth biomarker of interest is expressed only in tumor cells. In some embodiments, the third biomarker of interest is expressed by all cells and the fourth biomarker of interest is expressed only in tumor cells. In some embodiments, the fourth biomarker of interest is the subset biomarker. In some embodiments, the third biomarker of interest is expressed by all cells and the fourth biomarker of interest is the subset biomarker. In some embodiments, one or more fluorescence tags comprise a fluorophore conjugated to an antibody having a binding affinity for a specific biomarker or another antibody. In some embodiments, one or more fluorescence tags are fluorophores with affinity for a specific biomarker.

In another aspect, disclosed are methods utilizing a system comprising an imaging device and a controller for deriving a value for % biomarker positivity (PBP) for all cells or, optionally, one or more subsets thereof present in a field of view of a tissue sample from a cancer patient that are used in methods of treating cancer in the patient.

In some embodiments, disclosed herein are methods utilizing a system comprising an imaging device and a controller for treating cancer in a patient in need thereof, the method comprising deriving a value for % biomarker positivity (PBP) for all cells or, optionally, one or more subsets thereof present in a field of view of a tissue sample from the patient. In some embodiments, the deriving step is as described herein.

In some embodiments, disclosed herein are methods of deriving a value for % biomarker positivity (PBP) for all cells or, optionally, one or more subsets thereof present in a field of view of a tissue sample comprising: (i) using an imaging system to obtain image data for the tissue sample taken from a cancer patient, the imaging system comprising: a housing comprising a stage for positioning the sample in an imaging field, an electromagnetic radiation source for directing electromagnetic radiation at the sample, and a detector for collecting electromagnetic radiation output; and an electronic control system comprising memory and an processing circuit having image processing modules; and (ii) analyzing, using the image processing modules, the image data to derive the PBP for all cells or, optionally, one or more subsets thereof present in a field of view. In some embodiments, the methods of deriving a value for PBP for all cells or, optionally, one or more subsets thereof present in a field of view of a tissue sample are used as part of methods to monitor a progress of a patient diagnosed with cancer and undergoing immunotherapy. In some embodiments, the methods of deriving a value for PBP for all cells or, optionally, one or more subsets thereof present in a field of view of a tissue sample are used as part of methods to monitor immune cell modulation of a patient diagnosed with cancer and undergoing immunotherapy.

EXAMPLES

Example 16. Sample Preparation, Imaging, and Analysis of Imaging for Melanoma Tissue Samples from Human Patients Sample Preparation.

Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with a mouse anti-PD1 primary antibody. Slides were then washed before incubation with an anti-mouse HRP secondary antibody. Slides were washed and then PD-1 staining was detected using TSA+Cy® 3.5 (Perkin Elmer). Any residual HRP was then quenched using two washes of fresh 100 mM benzhydrazide with 50 mM hydrogen peroxide. The slides were again washed before staining with a rabbit anti-PD-L1 primary antibody. Slides were washed and then incubated with a cocktail of anti-rabbit HRP secondary antibody plus mouse anti-S100 directly labeled with 488 dye and 4',6-diamidino-2-phenylindole (DAPI). Slides were washed and then PD-L1 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 23.

Sample Imaging and Analysis.

Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue), FITC (green), and Cy® 5 (red) to create RGB images. These 4× magnification images were processed using an automated enrichment algorithm (developed using inForm) in field of view selector 104 to identify and rank possible 20× magnification fields of view according to the highest Cy® 5 expression.

The top 40 fields of view were imaged at 20× magnification across DAPI, FITC, Texas Red, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 1910 into individual channels and saved as a separate file.

The processed files were further analyzed using AQUAnalysis™ or through a fully automated process using AQUAserve™. Details were as follows.

Each DAPI image was processed by cell masker 1912 to identify all cell nuclei within that image (FIG. 7a), and then dilated by 3 pixels to represent the approximate size of an entire cell. This resulting mask represented all cells within that image (FIG. 7b).

Figure 8C:
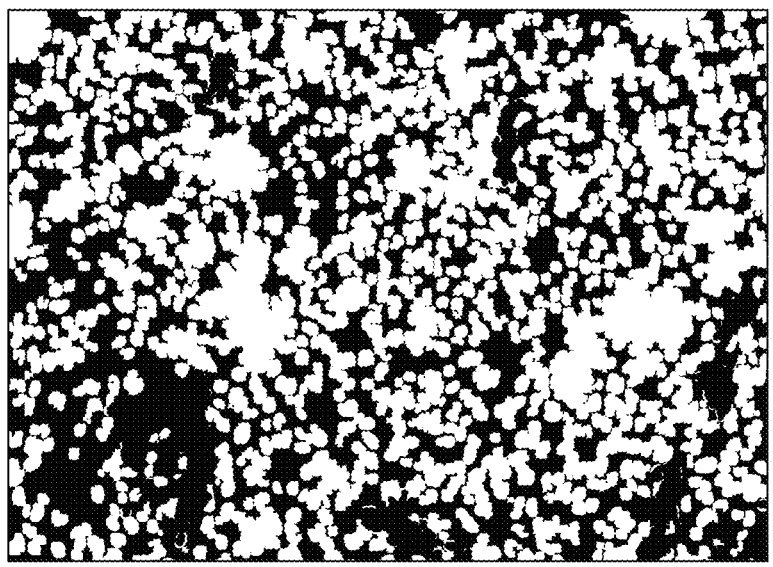

S100 (tumor cell marker for melanoma) detected with 488 dye (FIG. 8a) was processed by subset masker 1916 to create a binary mask of all tumor area within that image (FIG. 8b). Overlap between this mask and the mask of all cells created a new mask for tumor cells (FIG. 8c).

Similarly, absence of the tumor cell marker in combination with the mask of all nuclei created a new mask for all non-tumor cells (FIG. 8d), performed by non-tumor cell masker 1920.

Figure 9C:
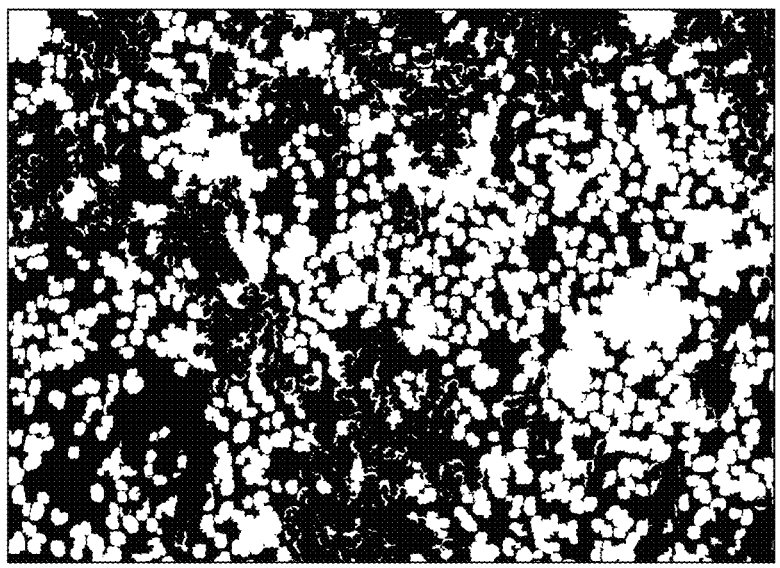
Figure 9D:
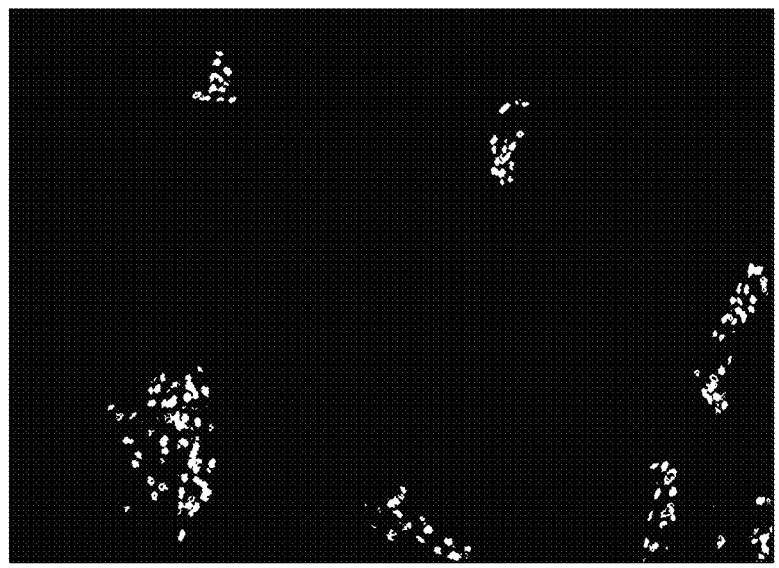

Each Cy® 5 image (FIG. 9a) was processed by biomarker masker 1922 to create a binary mask of all cells that are PD-L1-positive (FIG. 9b). Overlap between the mask of all tumor cells and the mask of all PD-L1-positive cells, using combination masker 1930, created a new mask of all PD-L1-positive tumor cells (FIG. 9c). Similarly, overlap between the mask of all non-tumor cells and the mask of all PD-L1-positive cells, using combination masker 1930, created a new mask of all PD-L1-positive non-tumor cells (FIG. 9d).

Each Cy® 3.5 image (FIG. 10a) was overlapped with the mask of all non-tumor cells to create a binary mask of all cells that are PD-1-positive (FIG. 10b).

Figure 27A:
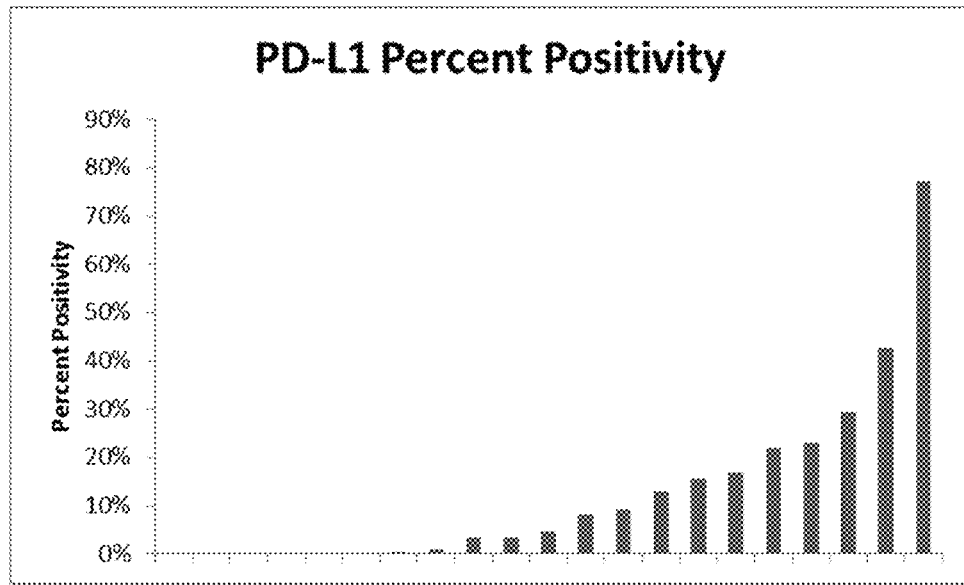
FIG. 27a shows a non-limiting example of values of % biomarker positivity (PBP) for all cells expressing PD-L1 in tissue samples from 21 melanoma patients, sorted by increasing PD-L1 expression.

The % biomarker positivity (PBP) for all tumor cells expressing PD-L1 was derived, using positivity calculator 1936, by dividing the total area, measured in pixels and determined by area evaluator 1932, of the mask of all PD-L1-positive tumor cells (FIG. 9c) with the total area, measured in pixels and determined by area evaluator 1932, of the mask of all tumor cells (FIG. 8c). Representative values of PBP for all cells expressing PD-L1 are shown in FIG. 27a (data sorted according to increasing expression).

Figure 8D:
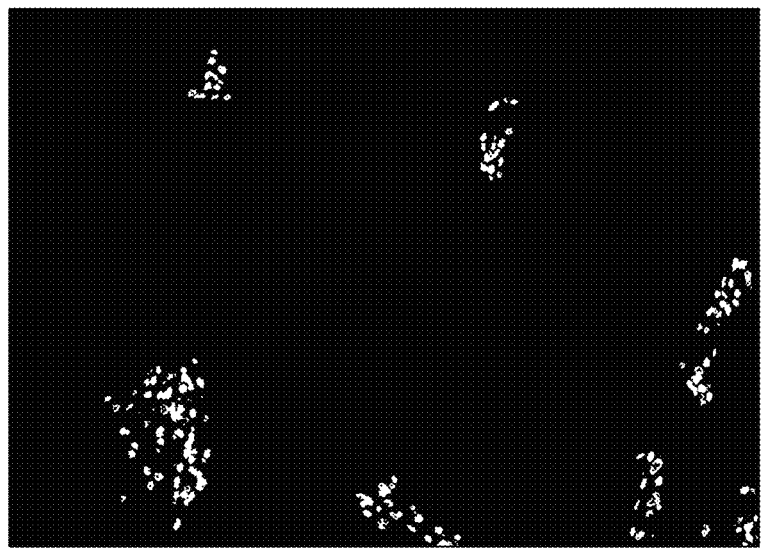
Figure 27B:
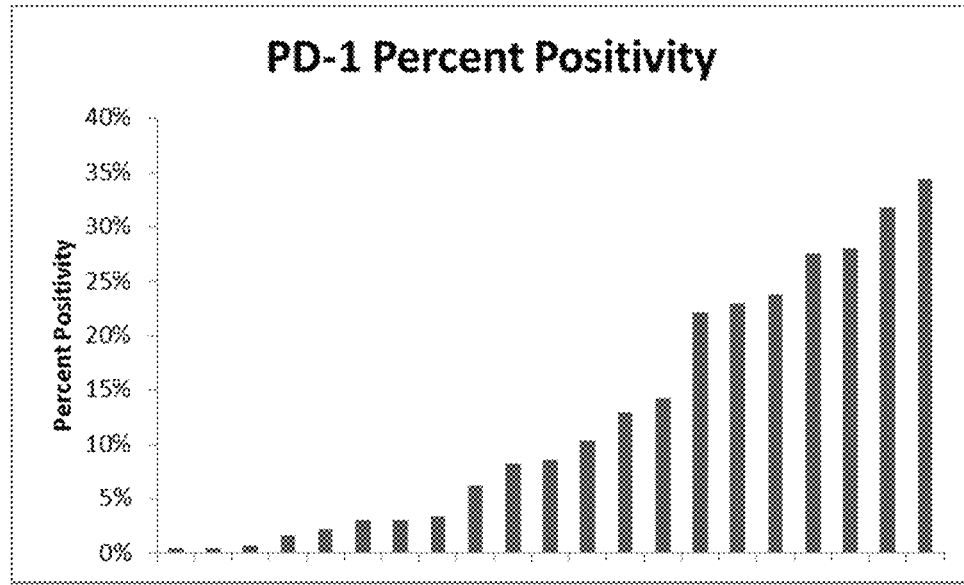
FIG. 27b shows a non-limiting example of values of PBP for all non-tumor cells expressing PD-1 in tissue samples from the same 21 melanoma patients of FIG. 27a, sorted by increasing PD-1 expression.

The PBP for all non-tumor cells expressing PD-1 was derived by dividing the total area, measured in pixels, of the mask of all PD-1-positive non-tumor cells (FIG. 10b) with the total area, measured in pixels, of the mask of all non-tumor cells (FIG. 8d). Representative values of PBP for all non-tumor cells expressing PD-1 are shown in FIG. 27b (data sorted according to increasing expression).

FIGS. 16 and 17 show a representative examples of overlaid masks indicating PD-L1-positive cells (red), PD-L-positive cells (yellow), tumor cells (S100, green), and all cells (DAPI, blue). FIG. 16 readily indicates the presence of PD-L1-positive cells (red), PD-1-positive cells (yellow), and all tumor cells (green). In contrast, for a negative responder to immunotherapy, the mask in FIG. 17 indicates the presence of tumor cells (S 100, green) and all cells (DAPI, blue), but shows little to no PD-L1-positive cells (red) or PD-1-positive cells (yellow).

Example 17. Sample Preparation, Imaging, and Analysis of Imaging for Non-Small Cell Lung Carcinoma (NSCLC) Tissue Samples from Human Patients Analogous procedures as Example 15 were performed, substituting the mouse anti-S100 directly labeled with 488 dye with a mouse anti-pan cytokeratin directly labeled with 488 dye for epithelial tumor samples. PBP values for PD-1 and PD-L1 are shown in FIG. 18. A subset of these patients exhibited high levels of receptor-ligand interaction reminiscent of immune suppression.

Example 18. Comparison of Analysis Techniques

To generate control specimens, lymphoma cell lines with previously established expression of PD-L1 (Karpas 299) or lack of expression (Ramos RA #1) were cultured according to manufacturer's instructions. The cells were then counted and the two cell lines were mixed at varying percentages to generate a series of FFPE cell line pellet block ranging in PD-L1 expression from 0-100%. Cores (600 μm) from these cell line mixtures as well as from normal tonsil tissue resections were then used to create a tissue microarray (TMA). A section of this TMA was then stained, imaged and each core was then scored for % PD-L1 positivity using AQUAnalysis™ (all steps as described in Example 15) and the results are shown on the Y-axis of FIG. 38, where each point represents a single core (single field of view).

Figure 28:
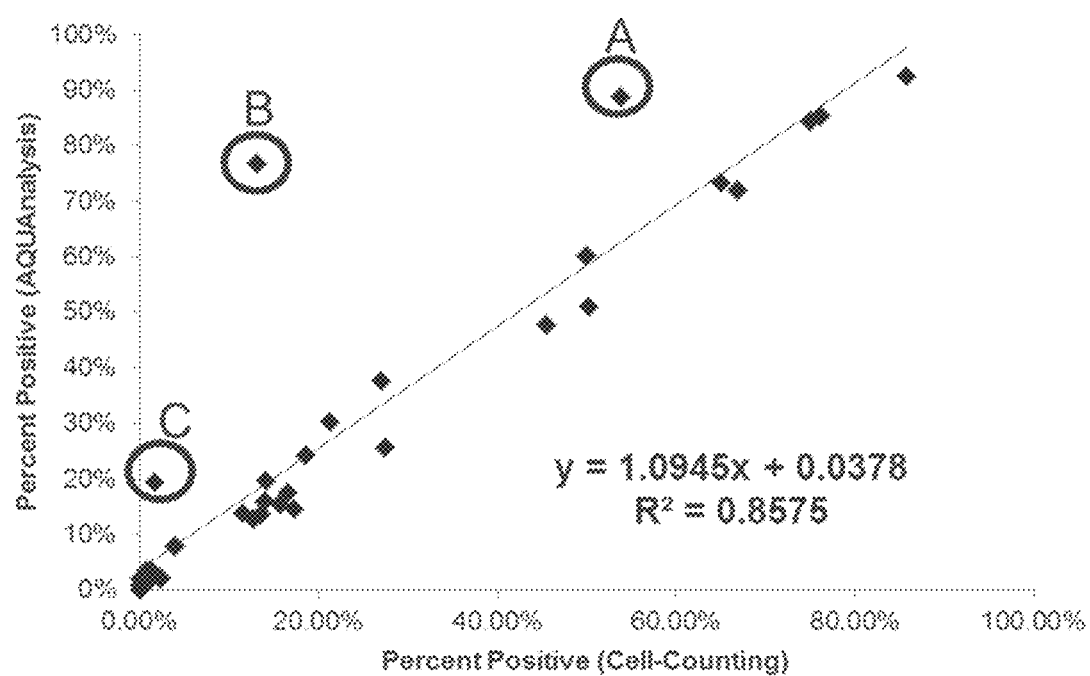
FIG. 28 shows a comparison of % PD-L1 positivity as ascertained by an automated cell counting method versus a method described herein.

Alternatively, the same images were quantified for % PD-L1 expression using a cell counting based software for comparison as follows. DAPI was used to first identify each cell nuclei and a morphological cytoplasm was then created surrounding the identified cell nuclei. An intensity threshold was established to identify cells with PD-L1 expression in the cytoplasm of the cells. The total number of cells identified above this threshold was then divided by the total number of cells in the image to determine the % PD-L1 positive cells in each core and the results are shown on the X-axis of FIG. 28. Overall, there was a high level of concordance between the two methods of cell counting ($R2=0.86$, slope 1.1); however, there were three noticeable outliers labeled as A, B, C in FIG. 28 where the % PD-L1 positivity determined by AQUA® scoring was significantly higher than that of the cell counting method. Points A and B were cell line cores where 100% of the cells were Karpas299 and thus values determined by AQUA® scoring were much closer to expected and the cell counting method failed to identify the cytoplasm of the cells as PD-L1 positive. Similarly, in point C, the cell mixture included a theoretical 40% of Karpas299 cells where the value determined by AQUA® scoring was again much closer to expected over the cell counting method. These results demonstrated the superiority of methods disclosed herein over the cell counting based software.

Example 19. Sample Preparation, Imaging, and Analysis of Imaging for Tissue Samples with Cells Expressing PD-L1 and Cells Expressing CD80

Analogous procedures as Example 15 are performed, substituting the staining and analysis of PD-1 with the staining and analysis of CD80.

Example 20. Sample Preparation, Imaging, and Analysis of Imaging for Tissue Samples with Cells Expressing CTLA-4 and Cells Expressing CD80

Sample Preparation

Formalin fixed paraffin embedded (FFPE) tissue samples were dewaxed, rehydrated and antigen retrieval was performed with elevated temperature conditions. Staining was then performed where the following steps were carried out. First, tissues were subjected to CTLA-4 expression detection using 20 pairs of hybridization probes spanning approximately 1 kb of the CTLA-4 mRNA using RNAScope® (Advanced Cell Diagnostics). In situ hybridization was visualized with TSA-Cy®3. The slides were washed and any residual HRP was then quenched using two washes of fresh 100 mM benzhydrazide with 50 mM hydrogen peroxide. The slides were again washed before staining with a mouse anti-CD80 primary antibody. Slides were washed and then incubated with an anti-mouse HRP secondary antibody. Slides were washed and then CD80 staining was detected using TSA-Cy® 5 (Perkin Elmer). Any residual HRP was then quenched using two washes of fresh 100 mM benzhydrazide with 50 mM hydrogen peroxide. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-AlexaFluor488® (Life Technologies). Slides were washed a final time before they were cover-slipped with mounting media and allowed to dry overnight at room temperature.

Figure 44A:
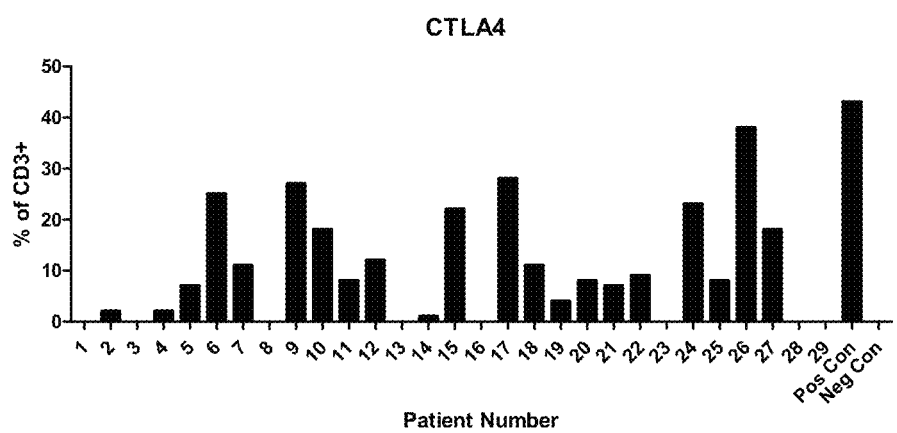
FIG. 44a shows a non-limiting example of quantitative assessment of CTLA-4 in T cells on melanoma tissues.
Figure 44B:
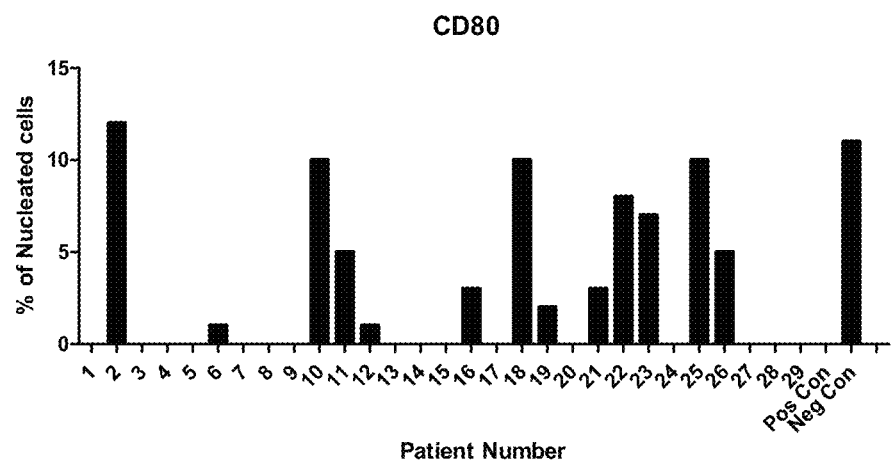
FIG. 44b shows a non-limiting example of quantitative assessment of CD80 on melanoma tissues.

Analogous imaging and analysis procedures as Example 1 were performed, imaging across DAPI, FITC, Cy® 3, and Cy® 5 wavelengths. Expression of CTLA-4 and CD80 was used to develop an enrichment algorithm for acquiring 20× images. Analysis was performed to survey the prevalence of CTLA-4 in CD3 positive T cells and CD80 expression in tumor samples taken from patients with metastatic melanoma. Results are shown in FIGS. 44*a* and 44*b*.

Example 21. Sample Preparation, Imaging, and Analysis of Imaging for Tissue Samples with Cells Expressing PD-L2 and Cells Expressing PD-1

Analogous procedures as Example 15 are performed, substituting the staining and analysis of PD-L1 with the staining and analysis of PD-L2.

Example 22. Sample Preparation, Imaging, and Analysis of Imaging for Tissue Samples with Cells Expressing CTLA-4 and Cells Expressing CD86

Analogous procedures as Example 15 are performed, substituting the staining and analysis of PD-L1 and PD-1 with the staining and analysis of CTLA-4 and CD86.

Example 23. Sample Preparation, Imaging, and Analysis of Imaging for Tissue Samples with Cells Expressing LAG-3 and Cells Expressing HLA-DR Analogous procedures as Example 15 are performed, substituting the staining and analysis of PD-L1 and PD-1 with the staining and analysis of LAG-3 and HLA-DR.

Example 24. Sample Preparation, Imaging, and Analysis of Imaging for Tissue Samples with Cells Expressing TIM-3 and Cells Expressing Galectin 9

Analogous procedures as Example 15 are performed, substituting the staining and analysis of PD-L1 and PD-1 with the staining and analysis of TIM-3 and Galectin 9.

Example 25. Sample Preparation, Imaging, and Analysis of Imaging for Tissue Samples with Cells Expressing 41BB and Cells Expressing 4.1BBL Analogous procedures as Example 15 are performed, substituting the staining and analysis of PD-L1 and PD-1 with the staining and analysis of 41BB and 4.1BBL.

Example 26. Sample Preparation, Imaging, and Analysis of Imaging for Tissue Samples with Cells Expressing OX40 and Cells Expressing OX40L Analogous procedures as Example 15 are performed, substituting the staining and analysis of PD-L1 and PD-1 with the staining and analysis of OX40 and OX40L.

Example 27. Sample Preparation, Imaging, and Analysis of Imaging for Tissue Samples with Cells Expressing CD40 and Cells Expressing CD40L Analogous procedures as Example 15 are performed, substituting the staining and analysis of PD-L1 and PD-1 with the staining and analysis of CD40 and CD40L.

Example 28. Sample Preparation, Imaging, and Analysis of Imaging for Tissue Samples with Cells Expressing ICOS and Cells Expressing ICOSL Analogous procedures as Example 15 are performed, substituting the staining and analysis of PD-L1 and PD-1 with the staining and analysis of ICOS and ICOSL.

Example 29. Sample Preparation, Imaging, and Analysis of Imaging for Tissue Samples with Cells Expressing GITR and Cells Expressing GITRL Analogous procedures as Example 15 are performed, substituting the staining and analysis of PD-L1 and PD-1 with the staining and analysis of GITR and GITRL.

Example 30. Sample Preparation, Imaging, and Analysis of Imaging for Tissue Samples with Cells Expressing HLA-DR and Cells Expressing TCR Analogous procedures as Example 15 are performed, substituting the staining and analysis of PD-L1 and PD-1 with the staining and analysis of HLA-DR and TCR.

Figure 31A:
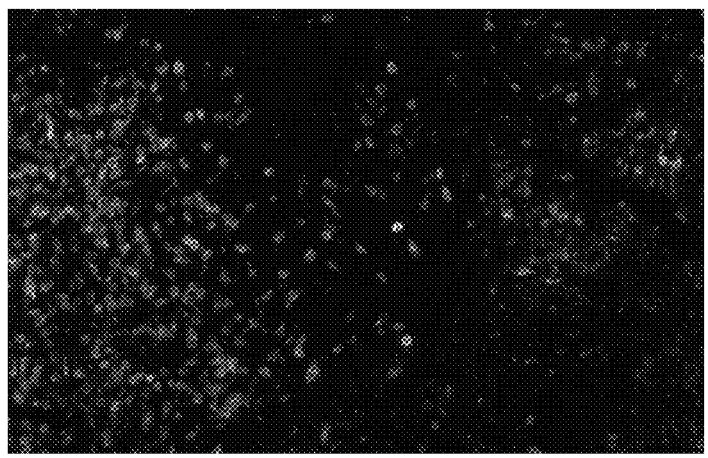
FIG. 31a shows a non-limiting example of an image of CD3 detected with Cy® 3.

Example 31. Sample Preparation, Imaging, and Analysis of CD3 and PD-1 on Tissue Samples from Diffuse Large B-Cell Lymphoma (DLBCL) Patients Sample preparation. Formalin fixed paraffin embedded (FFPE) tissue samples from DLBCL patients (n=43) were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce non-specific antibody staining. Next, the slides were stained with a mouse anti-PD1 primary antibody. Slides were then washed before incubation with an anti-mouse HRP secondary antibody. Slides were washed and then PD-1 staining was detected using TSA+Cy® 3 (Perkin Elmer). Primary and secondary antibody reagents were then removed via microwave. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 31.

Sample Imaging and Analysis.
Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue). Cy®3 (green), and Cy® 5 (red) to create RGB images. These 4× magnification images were processed using an automated enrichment algorithm (developed using inForm) in field of view selector 104 to identify and rank possible 20× magnification fields of view according to the highest Cy® 3 expression.

The top 40 fields of view were imaged at 20× magnification across DAPI, Cy®3, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 210 into individual channels and saved as a separate file.

The processed files were further analyzed using AQUAnalysis™ or through a fully automated process using AQUAserve™. Details were as follows.

Figure 29A:
FIG. 29a shows a non-limiting example of all nuclei detected with DAPI within an image.
Figure 29B:
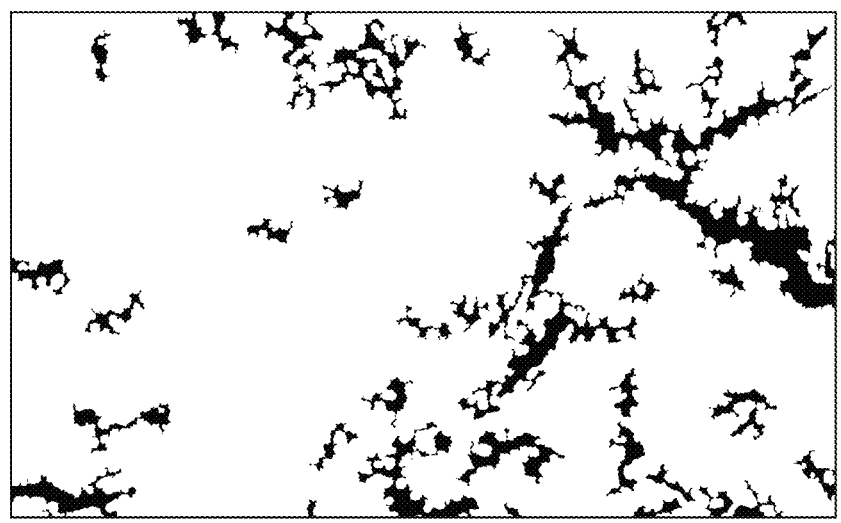

Each DAPI image was processed by cell masker 1912 to identify all cell nuclei within that image (FIG. 29a), and then dilated by 2 pixels to represent the approximate size of an entire cell. This resulting mask represented all cells within that image (FIG. 29b).

Figure 30A:
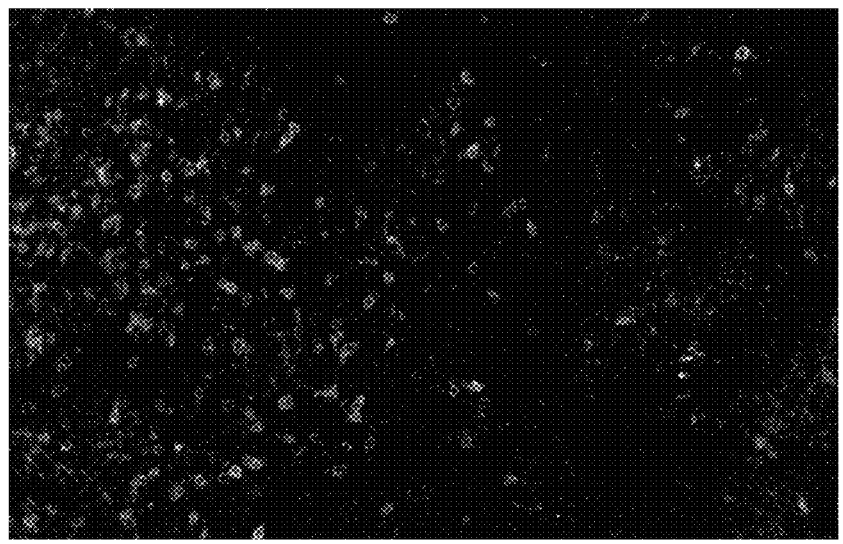
FIG. 30a shows a non-limiting example of an image of PD-1 detected with Cy® 5.
Figure 30B:
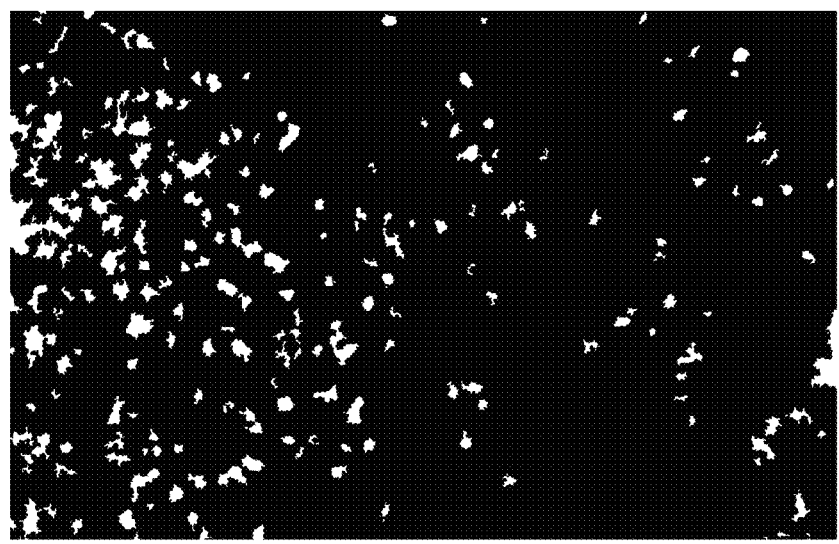

Each Cy® 5 image (FIG. 30a) was processed by biomarker masker 1922 to create a binary mask of all cells that are PD-1-positive (FIG. 30b).

Figure 31B:
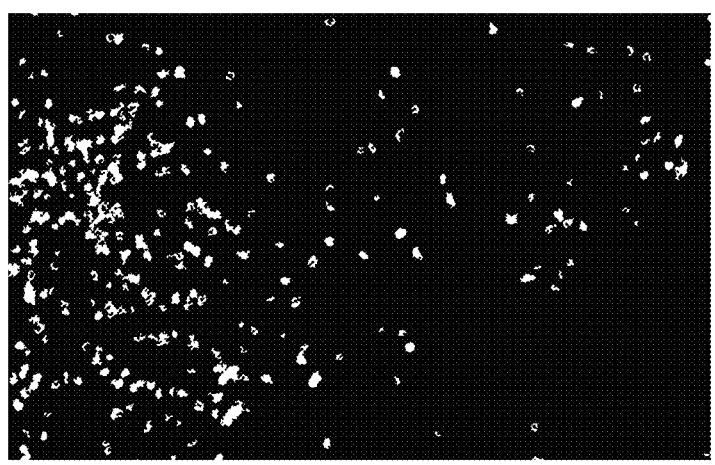

Each Cy® 3 image (FIG. 31a) was processed by biomarker masker 1922 to create a binary mask of all cells that are CD3-positive (FIG. 31b).

Figure 32:
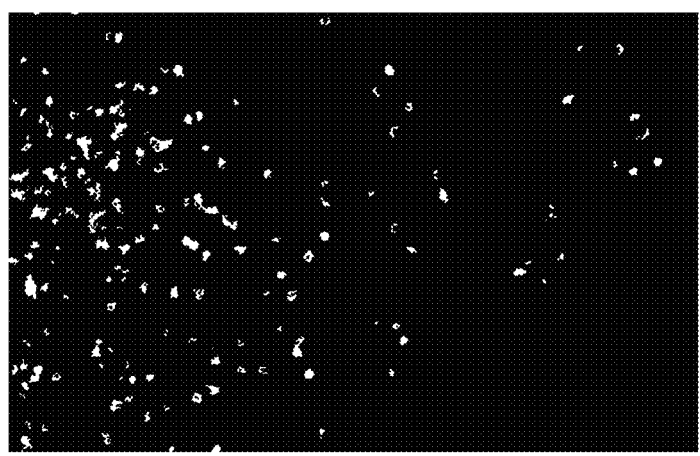
FIG. 32 shows a non-limiting example of a binary mask of all cells that are double positive for PD-1 and CD3.

The binary masks for all cells PD-1-positive and CD3-positive were combined to create a binary mask of all cells that are double positive for PD-1 and CD3 (FIG. 32).

Figure 33A:
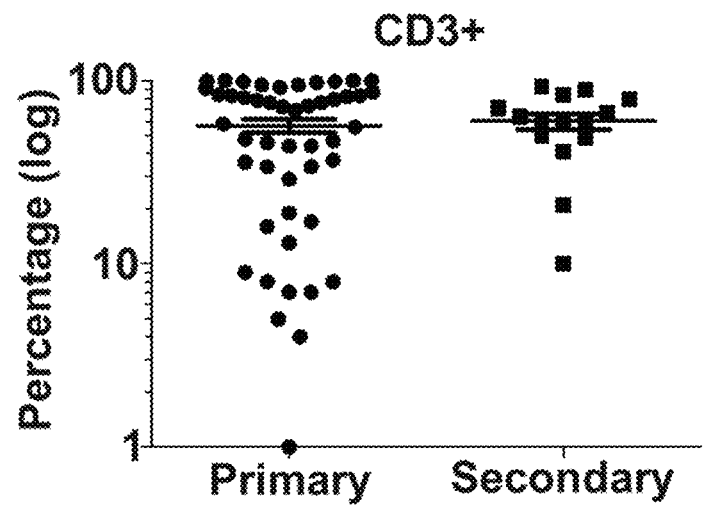
FIG. 33a shows a non-limiting example of quantitative assessment of CD3+ T-cells in tissue samples from DLBCL patients (n=43).
Figure 33B:
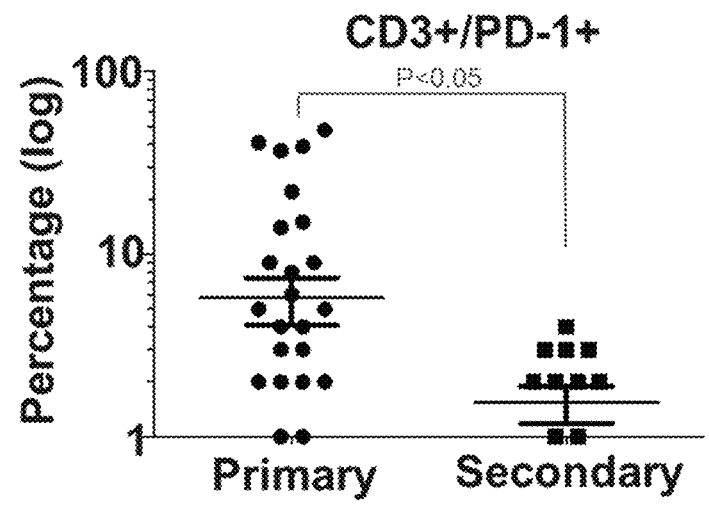
FIG. 33b shows a non-limiting example of quantitative assessment of CD3+/PD1+ T-cells in tissue samples from DLBCL patients (n=43).

The % biomarker positivity (PBP) for all CD3 cells expressing PD-1 was derived, using positivity calculator 1936, by dividing the total area, measured in pixels and determined by area evaluator 1932, of the mask of all PD-1-positive cells (FIG. 30b) with the total area, measured in pixels and determined by area evaluator 1932, of the mask of all CD3-positive cells (FIG. 31b). Differential distribution of exhausted T-cells (CD3+/PD1+) were observed in primary (low levels) versus secondary sites (high levels). Results are shown in FIGS. 33a and 33b.

Example 32. Platform Comparison

The accuracy of analogous procedures as Examples 15 and 30 was confirmed by comparison with flow cytometry. The frequencies of regulatory T-cells (based on FoxP3 and CD25 expression) was ascertained in whole blood stimulated with IL-2, TGF β, and CD28 for 5 days on a CD3-coated plate.

| Platform | FoxP3 | CD25 |
|---|---|---|
| Flow cytometry | 22% | 66% |
| PBP method | 24% | 66% |

Example 33. Assessment of CD25/FoxP3 T-Cells in Multiple Tumor Indications

Figure 34A:
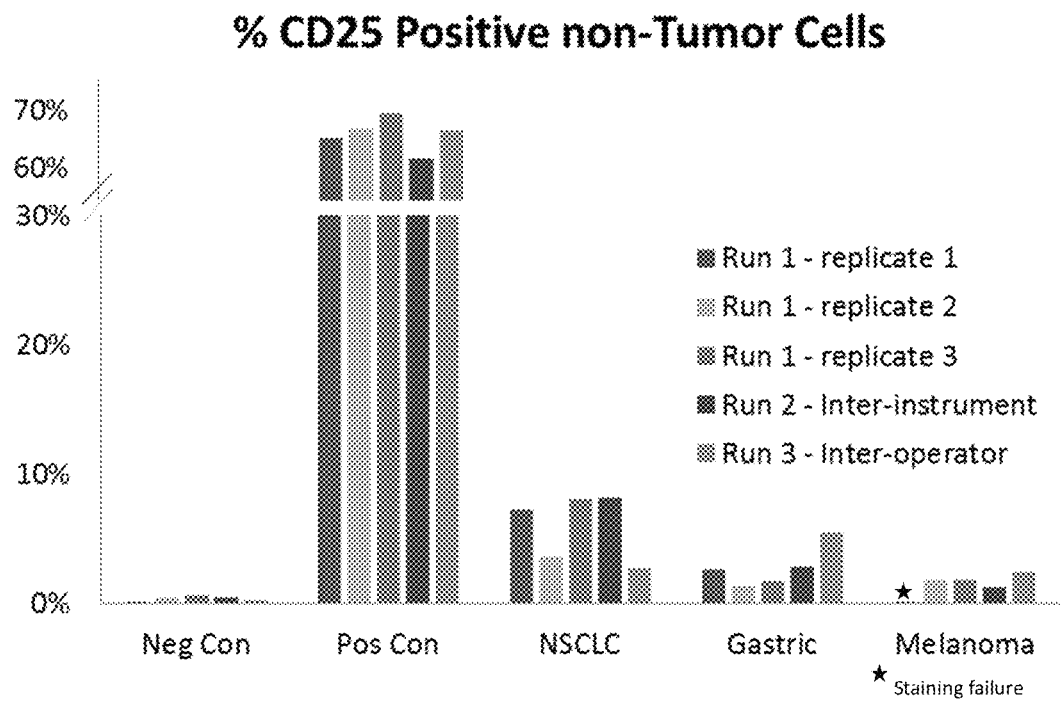
FIG. 34a shows a non-limiting example of quantitative assessment of CD25 on NSCLC, gastric, and melanoma tissues.
Figure 34B:
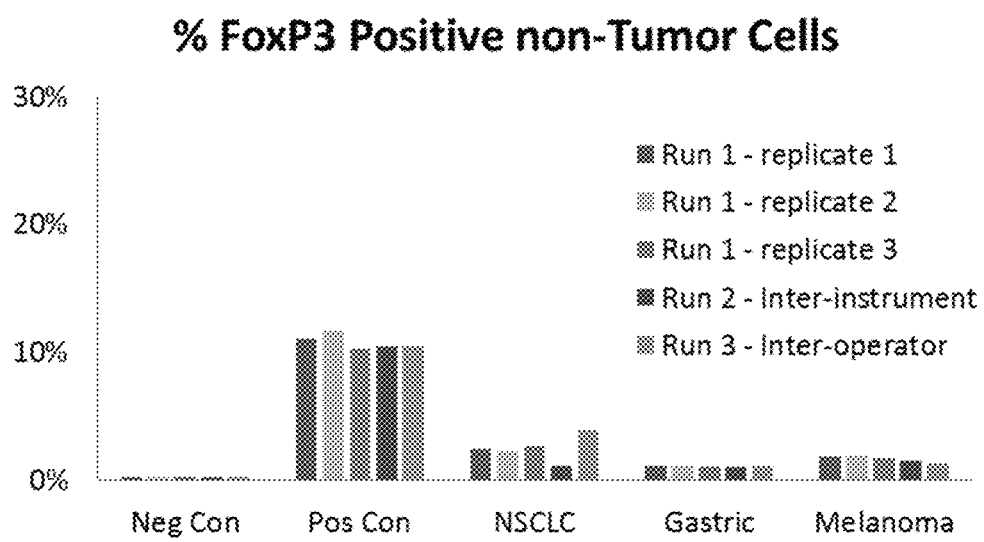
FIG. 34b shows a non-limiting example of quantitative assessment of FoxP3 on NSCLC, gastric, and melanoma tissues.
Figure 35:
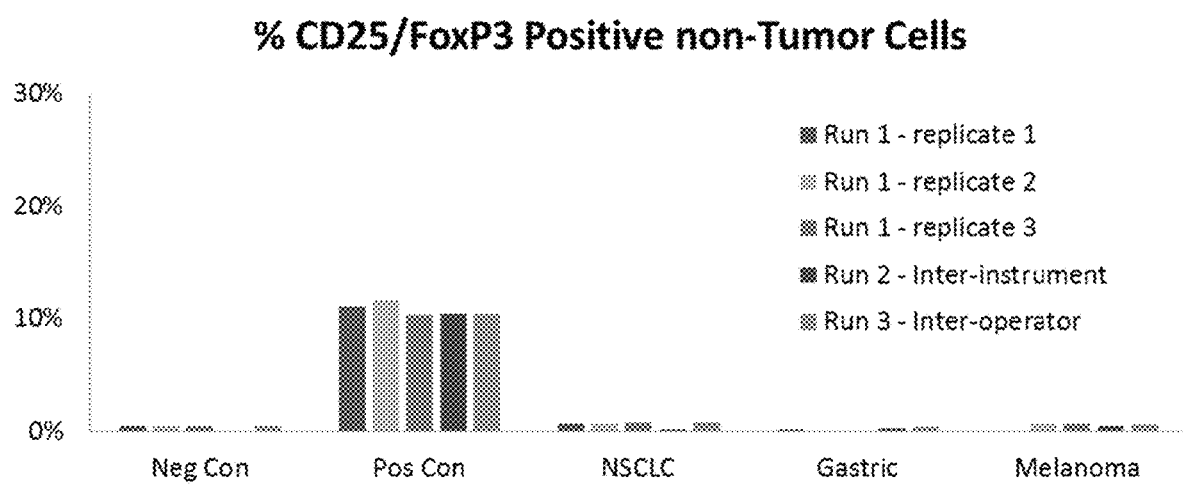
FIG. 35 shows a non-limiting example of quantitative assessment of CD25+/FoxP3+ T-cells in NSCLC, gastric, and melanoma tissues.

Analogous procedures as Example 30 were performed with the additional identification of tumor cells with either anti-S100 or anti-cytokeratin antibodies detected with an AlexaFluor488 secondary antibody and imaged across DAPI, FITC, Cy® 3, and Cy® 5 wavelengths for quantitative assessment of CD25 and FoxP3 on NSCLC, gastric, and melanoma tissues. The tissues were stained with antibodies recognizing CD25 and FoxP3 and their expression in non-tumor areas were calculated as % expression. The prevalence of CD25/FoxP3+ T-cells ranged from 1% to 10% in archival lung, gastric, and melanoma tissue specimens. Results are shown in FIGS. 34 and 35.

Example 34. Assessment of CD4/CD8 T-Cells in Multiple Tumor Indications

Figure 36A:
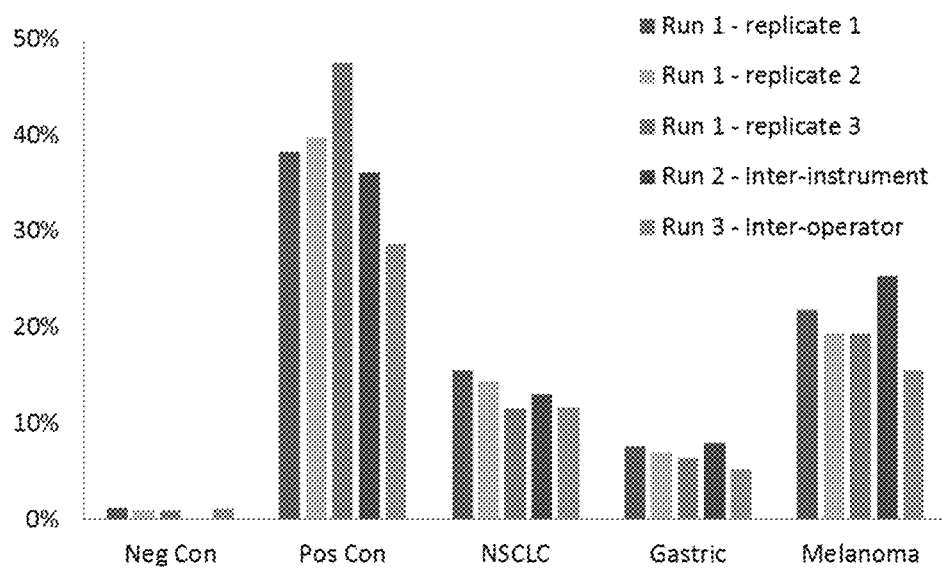
FIG. 36a shows a non-limiting example of quantitative assessment of CD4 on NSCLC, gastric, and melanoma tissues.
Figure 36B:
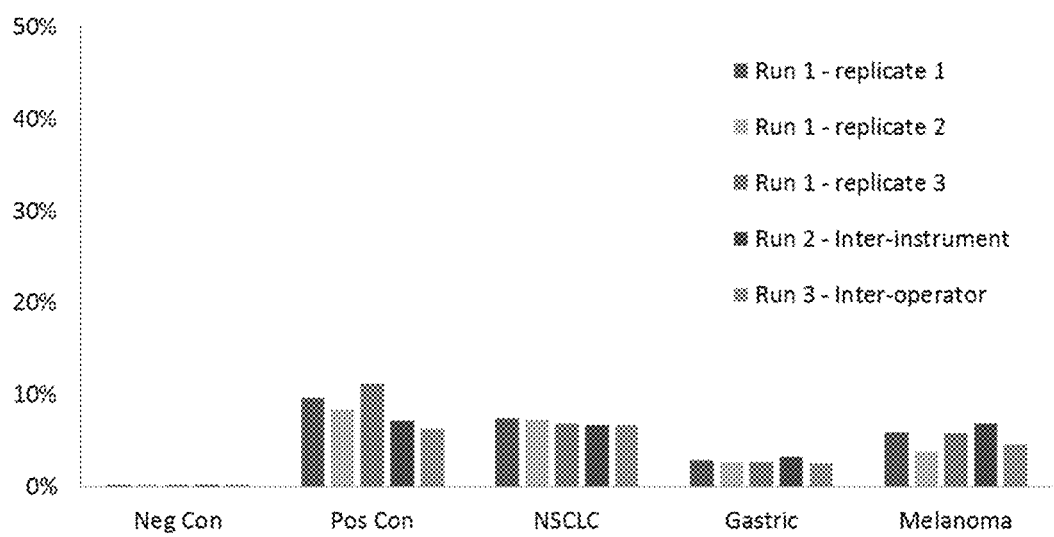
FIG. 36b shows a non-limiting example of quantitative assessment of CD8 on NSCLC, gastric, and melanoma tissues.

Analogous procedures as Example 30 were performed with the additional identification of tumor cells with either anti-S100 or anti-cytokeratin antibodies detected with an AlexaFluor488 secondary antibody and imaged across DAPI, FITC, Cy® 3, and Cy® 5 wavelengths for quantitative assessment of CD4 and CD8 on NSCLC, gastric, and melanoma tissues. The tissues were stained with antibodies recognizing CD4 and CD8 and their expressions in non-tumor areas were calculated as % expression. A broad range of expression (10%-50%) was observed for CD4+ and CD8+ T-cells in sequential sections of the tumor specimens. Results are shown in FIGS. 36a and 36b.

Example 35. Assessment of Myeloid Derived Suppressor Cell (MDSC)-Like Cells in Tumor Samples from Patients Diagnosed with Metastatic Melanoma or Non-Small Cell Lung Cancer To identify MDSC-like cells expressing phenotypic markers characteristic of myeloid cells (e.g., CD11b, CD33, and HLA-DR) and biochemical markers (e.g., ARG1 and IDO-1) that render suppressive function upon these cells, samples were stained with either CD11b, HLA-DR, and IDO, or CD11b, CD33, and ARG1.

Differential expression of CD11b, HLA-DR and IDO-1 was utilized to survey presence of a subset of suppressive myeloid cells known as TAMs (tumor associated macrophages) in tumor biopsies from metastatic melanoma patients. Representative sub-phenotypes that may be relevant for predicting response to cancer immunotherapies are shown in FIGS. 37a, 37b, 38a, and 38b.

Figure 39A:
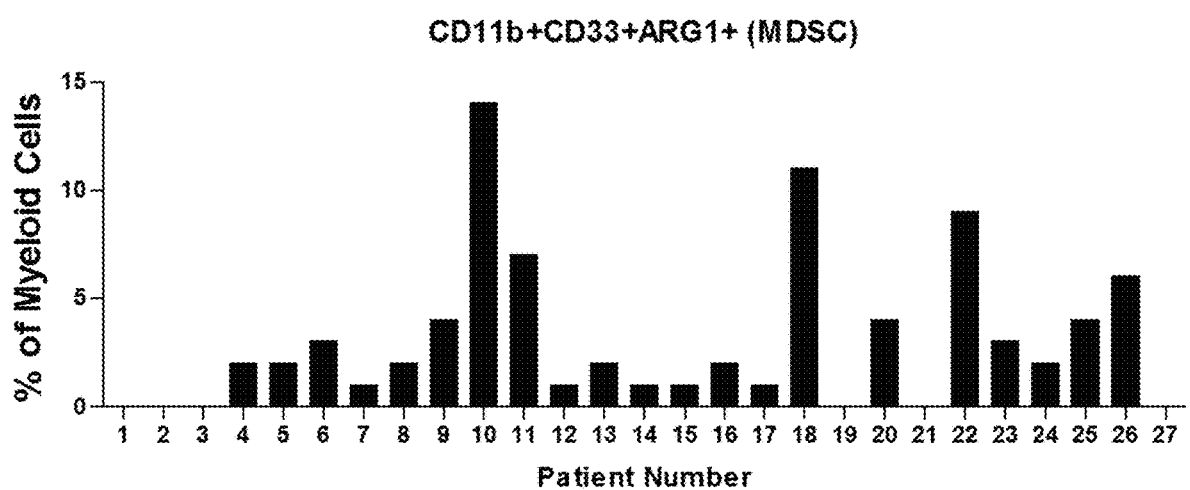
FIG. 39a shows a non-limiting example of quantitative assessment of CD11b+/CD33+/ARG1+ phenotype on NSCLC tissues.
Figure 39B:
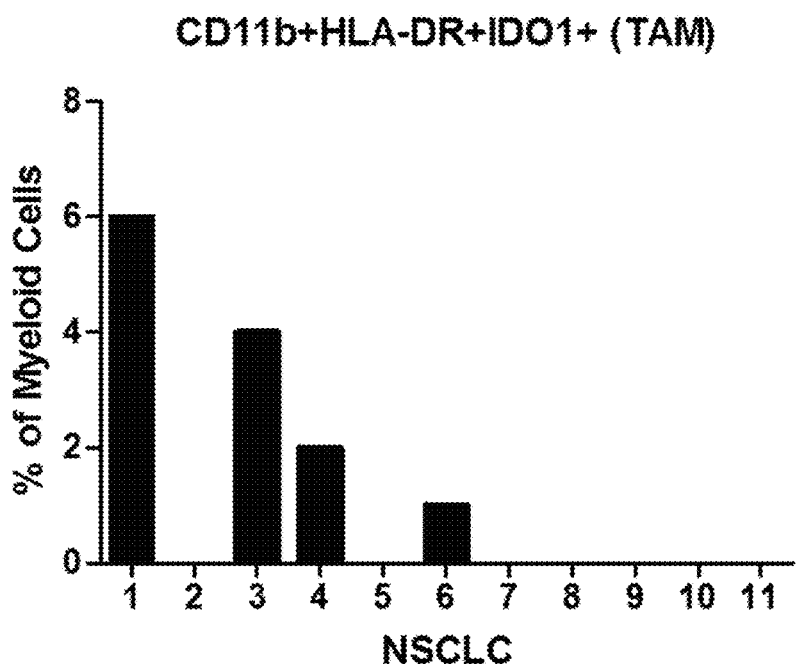
FIG. 39b shows a non-limiting example of quantitative assessment of CD11b+/HLA-DR+/IDO-1+ phenotype on NSCLC tissues.
Figure 40:
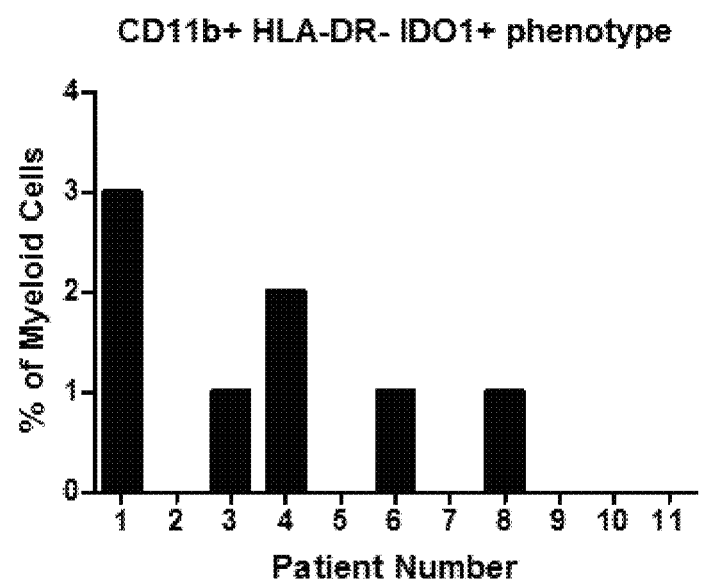
FIG. 40 shows a non-limiting example of quantitative assessment of CD11b+/HLA-DR−/IDO-1+ phenotype on NSCLC tissues.

Differential expression of CD11b, CD33, and ARG-1 or CD11b, HLA-DR, and IDO-1 were utilized to survey presence of MDSC like cells and TAMs in tumor specimens from advanced lung cancer (NSCLC) patients. Representative sub-phenotypes that may be relevant for predicting response to cancer immunotherapies are shown in FIGS. 39a, 39b, and 40.

Sample Preparation.

Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with either a rabbit anti-IDO-1 or mouse anti-CD33 primary antibody. Slides were then washed before incubation with anti-rabbit or anti-mouse HRP secondary antibody. Slides were washed and then anti-IDO-1 or anti-CD33 staining was detected using TSA+Cy® 5 (Perkin Elmer). Any residual HRP was then quenched using two washes of fresh 100 mM benzhydrazide with 50 mM hydrogen peroxide. The slides were again washed before staining with a mouse anti-HLA-DR or a rabbit anti-ARG1 primary antibody. Slides were washed and then incubated with anti-mouse or anti-rabbit HRP secondary antibody. Slides were washed and then the anti-HLA-DR or anti-ARG1 staining was detected using TSA-Cy® 3 (Perkin Elmer). Primary and secondary antibody reagents were then removed via microwave. The slides were again washed before staining with a rabbit anti-CD111b antibody. Slides were washed and then incubated with a cocktail of anti-rabbit HRP secondary antibody plus 4',6-diamidino-2-phenylindole (DAPI). Slides were washed and then anti-CD11b staining was detected using TSA-AlexaFluor488 (Life Technologies). Slides were washed a final time before they were cover-slipped with mounting media and allowed to dry overnight at room temperature.

Analogous procedures to Example 16 were used for sample imaging and analysis across DAPI, FITC, Cy®3, and Cy®5 wavelengths. 4× magnification images were processed using an automated enrichment algorithm (developed using inForm) in field of view selector 104 to identify and rank possible 20× magnification fields of view according to the highest Cy® 3 and Cy® 5 expression.

Each DAPI image was processed by cell masker 212 to identify all cell nuclei within that image and then dilated to represent the approximate size of an entire cell. This resulting mask represented all cells within that images Each AlexaFluor488® image was processed by biomarker masker 222 to create a binary mask of all cells that are CD11b positive.

Each Cy® 3 image was processed by biomarker masker 222 to create a binary mask of all cells that are HLA-DR or CD33 positive.

Each Cy® 5 image was processed by biomarker masker 222 to create a binary mask of all cells that are IDO-1 or ARG1 positive.

The binary masks for all cells CD11b positive and HLA-DR positive were combined to create a binary mask of all cells that are either double positive for CD11b and HLA-DR or are CD11b positive and HLA-DR negative.

Figure 37A:
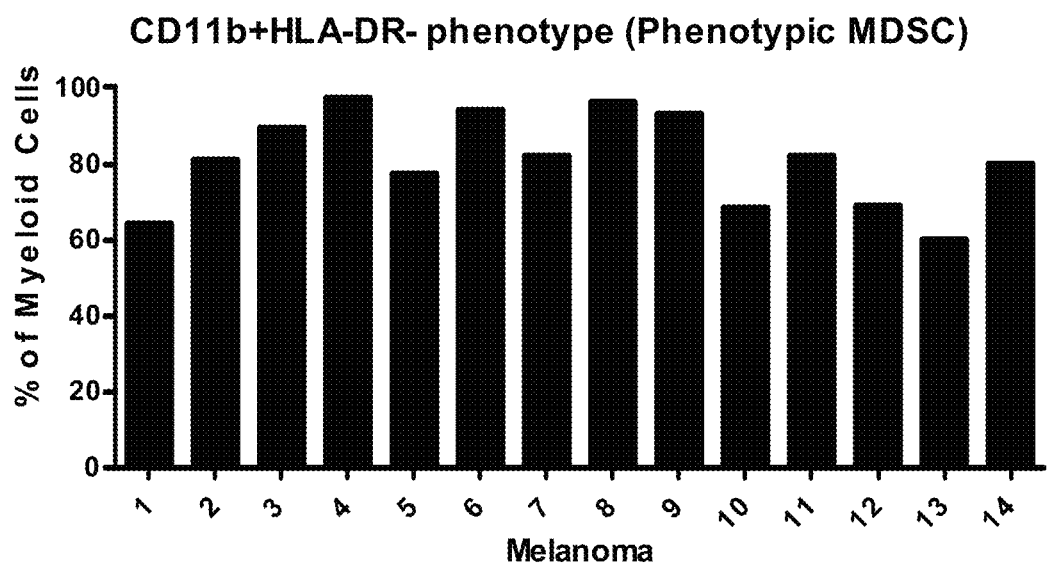
FIG. 37a shows a non-limiting example of quantitative assessment of CD11b+/LA-DR− phenotype on metastatic melanoma tissues.

The % biomarker positivity (PBP) for all CD11b cells lacking expression of HLA-DR was derived, using positivity calculator 236, by dividing the total area, measured in pixels and determined by area evaluator 232, of the mask of all CD11b-positive, HLA-DR-negative cells with the total area, measured in pixels and determined by area evaluator 232, of the mask of all CD11b-positive cells. Results are shown in FIG. 37a for tumor samples obtained from patients diagnosed with metastatic melanoma.

The binary masks for all cells CD11b positive, IDO positive, and HLA-DR positive were combined to create a binary mask of all cells that are CD11b-positive, HLA-DR-negative, and IDO-1-positive.

Figure 37B:
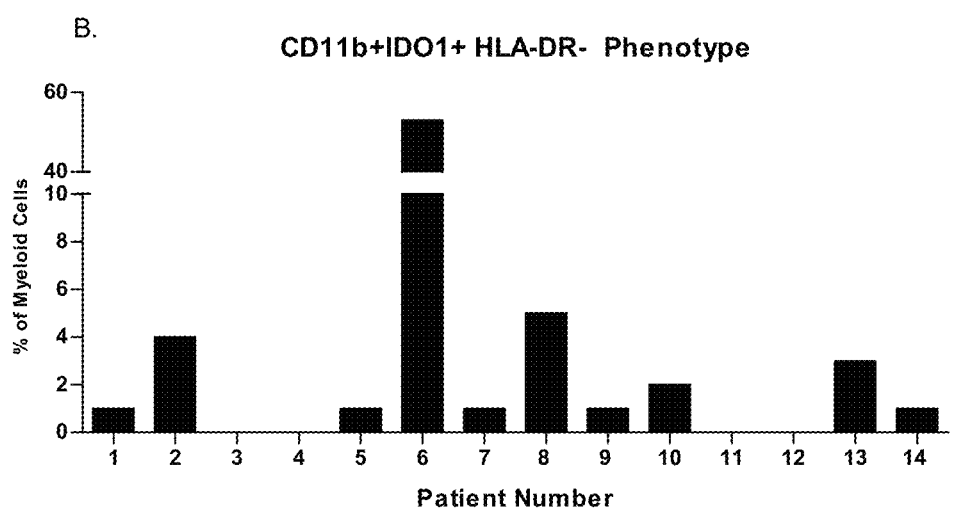
FIG. 37b shows a non-limiting example of quantitative assessment of CD11b+/IDO-1+/HLA-DR− phenotype on metastatic melanoma tissues.

The PBP for all CD11b cells expressing IDO-1, but lacking expression of HLA-DR was derived by dividing the total area, measured in pixels, of the mask of all CD11b-positive, HLA-DR-negative, IDO-1-positive cells with the total area, measured in pixels, of the mask of all CD11b-positive cells. Results are shown in FIG. 37b for tumor samples obtained from patients diagnosed with metastatic melanoma and FIG. 40 for patients diagnosed with non-small cell lung cancer.

The binary masks for all cells HLA-DR positive and IDO-1 positive were combined to create a binary mask of all cells that are double positive for HLA-DR and IDO-1.

Figure 38A:
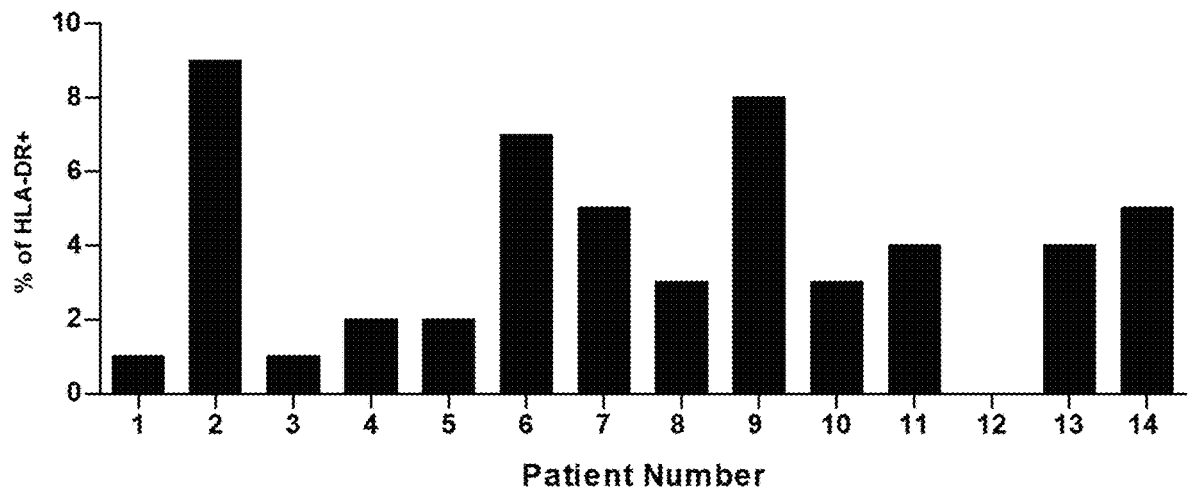
FIG. 38a shows a non-limiting example of quantitative assessment of IDO-1+/HLA-DR+ phenotype on metastatic melanoma tissues.

The % biomarker positivity (PBP) for all HLA-DR cells expressing IDO-1 was derived, using positivity calculator 236, by dividing the total area, measured in pixels and determined by area evaluator 232, of the mask of all IDO-1-positive, HLA-DR-positive cells with the total area, measured in pixels and determined by area evaluator 232, of the mask of all HLA-DR-positive cells. Results are shown in FIG. 38a for tumor samples obtained from patients diagnosed with metastatic melanoma.

The binary masks for all cells CD11b positive, IDO positive, and HLA-DR positive were combined to create a binary mask of all cells that are CD11b-positive, HLA-DR-positive, and IDO-1-positive.

Figure 38B:
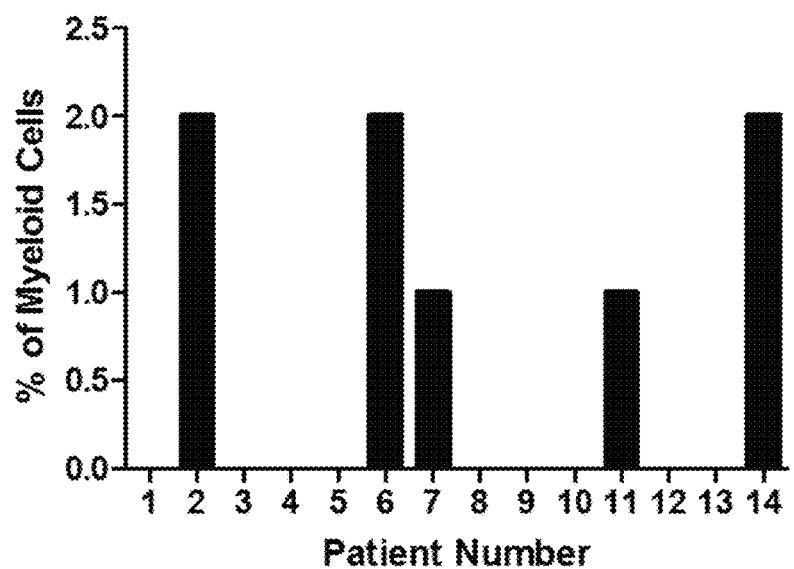
FIG. 38b shows a non-limiting example of quantitative assessment of CD11b+/IDO-1+/HLA-DR+ phenotype on metastatic melanoma tissues.

The PBP for all CD11b cells expressing IDO-1 and HLA-DR was derived by dividing the total area, measured in pixels, of the mask of all CD11b-positive, HLA-DR-positive, IDO-1-positive cells with the total area, measured in pixels, of the mask of all CD11b-positive cells. Results are shown in FIG. 38b for tumor samples obtained from patients diagnosed with metastatic melanoma and FIG. 39b for tumor samples obtained from patients diagnosed with non-small cell lung cancer.

The binary masks for all cells CD11b positive, CD33 positive, and ARG1 positive were combined to create a binary mask of all cells that are CD11b-positive, CD33-positive, and ARG1-positive.

The PBP for all CD11b cells expressing CD33 and ARG1 was derived by dividing the total area, measured in pixels, of the mask of all CD11b-positive. CD33-positive. ARG1-positive cells with the total area, measured in pixels, of the mask of all CD11b-positive cells. Results are shown in FIG. 39a for tumor samples obtained from patients diagnosed with non-small cell lung cancer.

Figure 41:
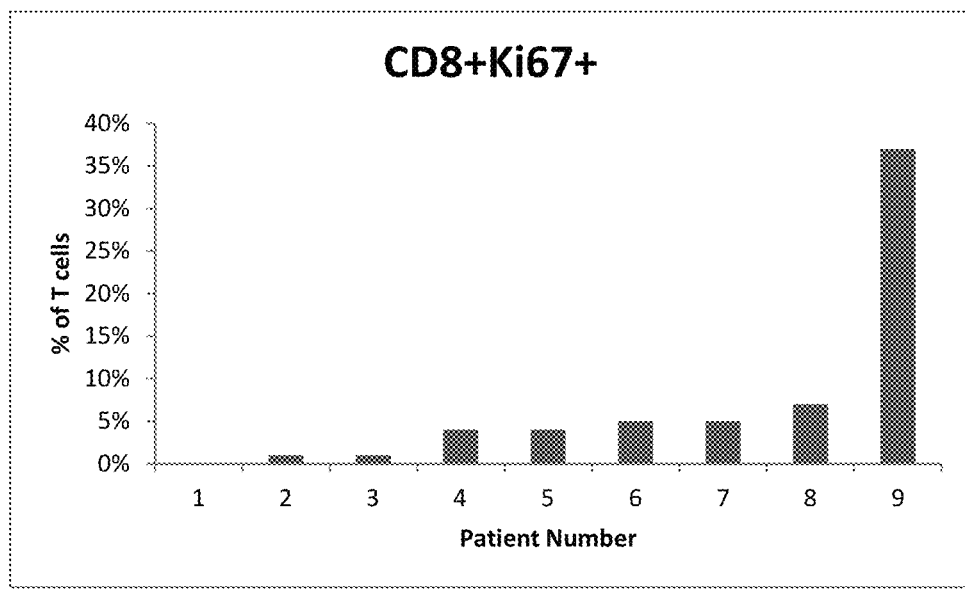
FIG. 41 shows a non-limiting example of quantitative assessment of CD8+Ki67+ T cells on metastatic melanoma tissues.

Example 36. Assessment of Activated T Cells in Tumor Samples from Patients Diagnosed with Metastatic Melanoma Analogous procedures as Example 20 were performed to stain each sample with a combination of DAPI. CD3, CD8, and Ki67 to identify sub-populations of activated T cells. Prevalence of CD8+Ki67+ was surveyed in tumor biopsies obtained from patients diagnosed with metastatic melanoma (FIG. 41).

Figure 42A:
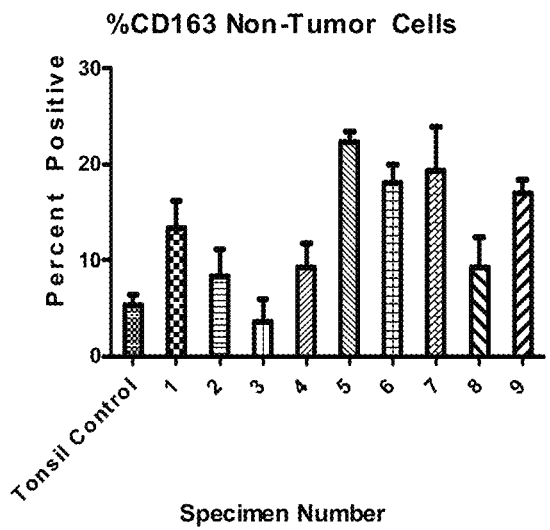
FIG. 42a shows a non-limiting example of quantitative assessment of CD163+ cells on metastatic melanoma tissues.
Figure 42B:
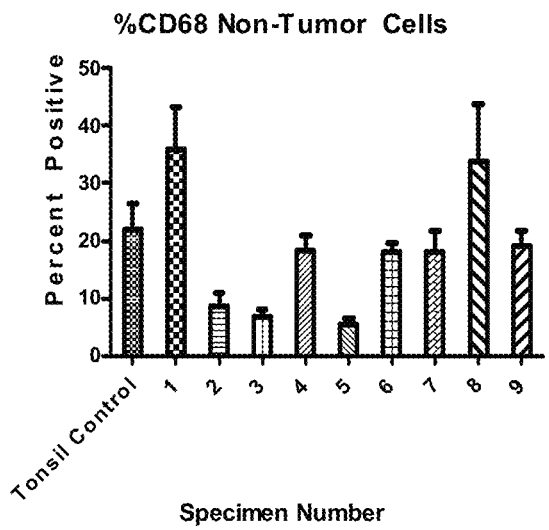
FIG. 42b shows a non-limiting example of quantitative assessment of CD68+ cells on metastatic melanoma tissues.
Figure 42C:
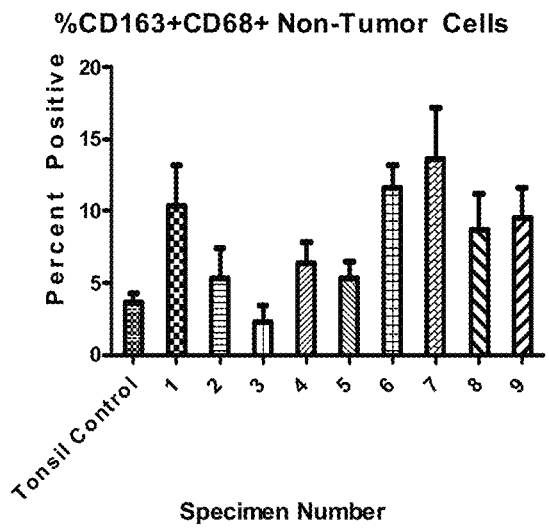
FIG. 42c shows a non-limiting example of quantitative assessment of CD163+CD68+ cells on metastatic melanoma tissues.

Example 37. Assessment of Macrophage Prevalence in Tumor Samples from Patients Diagnosed with Metastatic Melanoma Analogous procedures as Example 16 were performed with the additional identification of tumor cells with anti-S100 antibody detected with an AlexaFluor488 secondary antibody and imaged across DAPI, FITC. Cy® 3, and Cy® 5 wavelengths for quantitative assessment of CD163 and CD68 on melanoma tissues. The tissues were stained with antibodies recognizing CD163 and CD68 and their expression in non-tumor areas were calculated as single PBP expression or double PBP expression. Results are shown in FIGS. 42a, 42b, and 42c.

Example 38. Assessment of T Cell Suppression Prevalence in Tumor Samples from Patients Diagnosed with Diffuse Large B-Cell Lymphoma (DLBCL) and Neuroendocrine Tumors (NET)

Figure 43A:
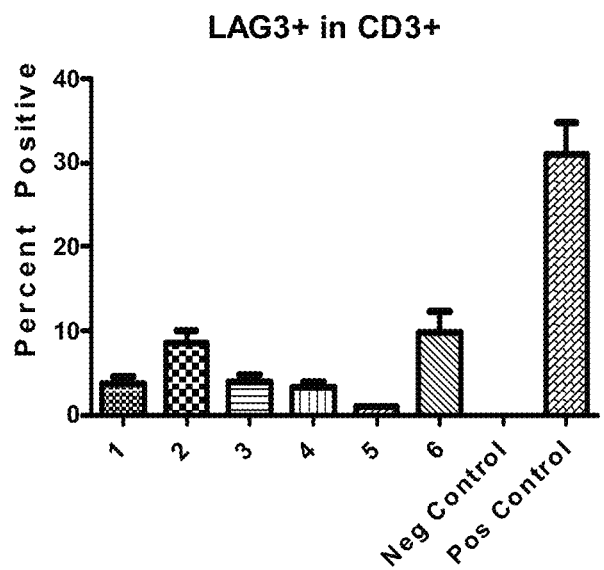
FIG. 43a shows a non-limiting example of quantitative assessment of LAG-3 positive T cells on DLBCL and NET tissues.
Figure 43B:
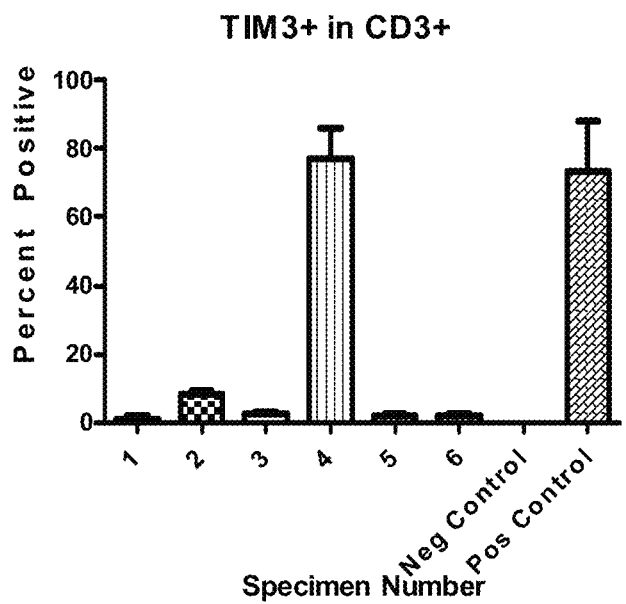
FIG. 43b shows a non-limiting example of quantitative assessment of TIM-3 positive T cells on DLBCL and NET tissues.

Analogous procedures as Example 1 were performed to stain the DLBCL and NET tumor specimens with a mouse anti-LAG-3 primary antibody, anti-mouse HRP secondary, detected with TSA+Cy®3.5, with remaining HRP quenched with 100 mM benzhydrazide and 50 mM hydrogen peroxide. Following this, slides were stained with a rabbit anti-TIM-3 primary antibody, anti-rabbit HRP secondary, detected with TSA-Cy®5. Primary and secondary antibodies were then removed via microwave. Tissues were then stained with a rabbit anti-CD3 primary antibody, anti-rabbit HRP secondary plus 4',6-diamidino-2-phenylindole (DAPI), detected with Opal™520. Imaging was performed analogous to Example 1 across DAPI, FITC, Texas Red, and Cy® 5 wavelengths. Analysis was performed analogous to Example 1 to determine PBP prevalence of T cells that were LAG-3 and TIM-3 positive respectively. Results are shown in FIGS. 43a and 43b.

Para. A. An image processing system, comprising:
an image processing controller comprising a processing circuit configured to execute instructions stored on a computer-readable medium which cause the controller of the image processing system to: receive image data from an imaging device, the image data describing a sample of tumor tissue taken from a cancer patient; and
determine, using the image data, a score representative of a nearness between at least one pair of cells in the tumor tissue, a first member of the at least one pair of cells expressing a first biomarker and a second member of the at least one pair of cells expressing a second biomarker that is different from the first biomarker;
wherein the score is indicative of a likelihood that the cancer patient will respond positively to immunotherapy.

Para. B. The system of Para. A in which the score representative of a nearness between at least one pair cells is representative of an extent that the pair of cells are within a predetermined proximity of one another.

Para. C. The system of Para. A in which the nearness is assessed on a pixel scale.

Para. D. The system of Para. B in which the predetermined proximity between the pair of cells ranges from about 1 pixel to about 100 pixels.

Para. E. The system of Para. B in which the predetermined proximity between the pair of cells ranges from about 5 pixel to about 40 pixels.

Para. F. The system of Para. B in which the predetermined proximity between the pair of cells ranges from about 0.5 µm to about 50 µm.

Para. G. The system of Para. B in which the predetermined proximity between the pair of cells ranges from about 2.5 µm to about 20 µm.

Para. H. The system of Para. A in which the score is determined by obtaining a proximity between the boundaries of the pair of cells.

Para. I. The system of Para. A in which the score is determined by obtaining a proximity between the centers of mass of the pair of cells.

Para. J. The system of Para. A in which the score is determined using boundary logic based on a perimeter around a selected first cell of the pair of cells.

Para. K. The system of Para. A in which the score is determined by determining an intersection in the boundaries of the pair of cells.

Para. L. The system of Para. A in which the score is determined by determining an area of overlap of the pair of cells.

Para. M. The system of Para. A in which the processing circuit is further configured to execute instructions which cause the controller of the image processing system to:
separate the image data into unmixed image data; and
provide the data through a plurality of data channels, in which the unmixed image data in a first data channel describes fluorescence signals attributable to the first biomarker and the unmixed image data in a second data channel describes fluorescence signals attributable to the second biomarker.

Para. N. The system of Para. M in which, to determine the score, the processing circuit is further configured to execute instructions which cause the controller of the image processing system to: dilate fluorescence signals attributable to the first biomarker from the first data channel by a predetermined margin that is selected to encompass proximally located cells expressing the second biomarker to generate a dilated first biomarker mask;
determine an interaction area, wherein the interaction area is a first total area for all cells which express the second biomarker and are encompassed within the dilated fluorescence signals attributable to the cells expressing the first biomarker; and
divide the interaction area by a normalization factor, and multiplying the resulting quotient by a predetermined factor to arrive at a spatial proximity score.

Para. O. The system of Para. N in which the normalization factor is a total area for all cells that have a capacity to express the second biomarker.

Para. P. The system of Para. N in which the interaction area is determined by combining the dilated first biomarker mask with a mask representative of cells that express the second biomarker, determined from signals of the second data channel.

Para. Q. The system of Para. M in which a third data channel describes fluorescence signals attributable to cell nuclei and a fourth data channel describes fluorescence signals attributable to tumor area in the sample.

Para. R. The system of Para. O in which the total area for all cells that have a capacity to express the second biomarker is determined by combining a cell mask representative of all cells in the sample, based on signals from the third data channel, and a tumor area mask representative of the tumor area on the sample, based on signals from the fourth data channel.

Para. S. The system of Para. R in which combining the cell mask and the tumor area mask comprises removing the tumor area mask from the cell mask.

Para. T. The system of any of Paras. N-S in which each mask is generated by assigning a binary value to each pixel of image data from a selected channel.

Para. U. The system of Para. T in which the binary value is assigned to each value by a threshold function, wherein the threshold function assigns a value of 1 to each pixel that has an intensity equal to or greater than a predetermined intensity threshold, and assigns a value of 0 to each pixel that has an intensity below the predetermined intensity threshold.

Para. V. The system of Para. T in which the binary value is assigned to each value by a histogram threshold function, wherein the histogram threshold function uses a sliding scale of pixel intensity to determine a threshold, and assigns a value of 1 to each pixel that has an intensity equal to or greater than an intensity threshold, and assigns a value of 0 to each pixel that has an intensity below the intensity threshold.

Para. W. The system of Para. V in which the threshold is determined by:
summing an intensity of every pixel into a total intensity;
multiplying a threshold percentage by the total intensity to obtain a cut-off sum;

grouping all pixels by intensity in a histogram; and summing the pixel intensities from lowest to highest until the cut-off sum is achieved:

wherein the last highest pixel intensity visited in the process is the intensity threshold.

Para. X. The system of any of Paras. N-W in which combining the masks is performed using an "and" operation: wherein the "and" operation is a multiplication of the pixel intensity of a pixel in a first mask by the pixel intensity of the pixel in a second mask.

Para. Y. The system of any of Paras. N-W in which combining the masks is performed using an "out" operation; wherein the "out" operation removes the a second mask from a first mask.

Para. Z. The system of Para. A in which the processing circuit is further configured to execute instructions which cause the controller of the image processing system to:

obtain image data at a low magnification representative of the concentration of the first or the second biomarker in the image:

identify areas that include the highest concentration of the first or the second biomarker;

select a predetermined number of the areas including the highest concentration of the first or the second biomarker;

send instructions to imaging device to obtain high magnification image data for the predetermined number of areas; and wherein the high magnification image data is provided to the controller to be analyzed and used to determine the score.

Para. AA. The system of Para. Z in which the low magnification is less than or equal to 10× magnification and wherein the high magnification is greater than 10×.

Para. AB. The system of Para. AA in which the low magnification is 10× magnification and wherein the high magnification is 40×.

Para. AC. The system of Para. AA in which the low magnification is 10× magnification and wherein the high magnification is 20×.

Para. AD. The system of Para. AA in which the low magnification is 4× magnification and wherein the high magnification is 40×.

Para. AE. The system of Para. AA in which the low magnification is 4× magnification and wherein the high magnification is 20×.

Para. AF. The system of Para. A wherein the image processing unit is further configured to associate the score with metadata associated with the images of the sample.

Para. AG. The system of Para. A wherein the image processing unit generates a report including the score.

Para. AH. The system of Para. A wherein the image processing unit is further configured to provide the score to an operator to determine immunotherapy strategy.

Para. AI. The system of Para. A wherein the image processing unit is further configured to record the score in a database.

Para. A. The system of Para. A wherein the image processing unit is further configured to associate the score with a patient's medical record.

Para. AK. The system of Para. A wherein the image processing unit is further configured to display the score on a display device.

Para. AL. The system of Para. A in which the first member of the at least one pair of cells comprises a tumor cell and the second member of the at least one pair of cells comprises a non-tumor cell.

Para. AM. The system of Para. AL in which the non-tumor cell comprises an immune cell.

Para. AN. The system of Para. A in which the first and second members of the at least one pair of cells comprise immune cells.

Para. AO. The system of Para. A in which the first member of the at least one pair of cells comprises a tumor cell, a myeloid cell, or a stromal cell and the second member of the at least one pair of cells comprises an immune cell.

Para. AP. The system of Para. AO in which the tumor cell, myeloid cell, or stromal cell expresses PD-L1 and the immune cell expresses PD-1.

Para. AQ. The system of Para. A in which the image processing unit is further configured to select a predetermined number of fields of view available from the sample comprising tumor tissue taken from the cancer patient and determine the score from data associated with each field of view.

Para. AR. The system of Para. AQ in which the sample is stained with a plurality of fluorescence tags, and wherein each of the fluorescence tags is directed to a specific biomarker.

Para. AS. The system of Para. AQ or Para. AR, in which the plurality of fluorescence tags comprises a first fluorescence tag for the first biomarker and a second fluorescence tag for the second biomarker.

Para. AT. The system of any one of Paras. AQ-AS in which the margin ranges from about 1 to about 100 pixels.

Para. AU. The system of any one of Paras. AQ-AT in which the proximally located cells expressing the second biomarker are within about 0.5 to about 50 m of a plasma membrane of the cells that express the first biomarker.

Para. AV. The system of any one of Paras. N-AU in which the predetermined factor is $10^4$.

Para. AW. The system of Para. A in which the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3. 41BB, OX40, CTLA-4. CD40L, CD28, GITR, ICOS, CD28, and combinations thereof.

Para. AX. The system of any one of Paras. A-AW in which the threshold value ranges from about 500 to about 5000.

Para. AY. The system of Para. AX in which the threshold value is about 900 plus or minus 100.

Para. AZ. The system of any one of Paras. A-AY in which the immunotherapy comprises immune checkpoint therapy.

Para. BA. A system for determining a score representative of a proximity between at least one pair of cells in a tumor tissue sample, the system comprising:

a processing circuit comprising a memory, the memory comprising:

a spectral unmixer configured to receive image data from an imaging device, separate the image data into unmixed image data, and provide the data through a plurality of data channels, in which the unmixed image data in a first data channel describes fluorescence signals attributable to a cell nucleus, the unmixed data in a second data channel describes fluorescence signals attributable to tumor tissue, the unmixed data in a third data channel describes fluorescence signals attributable to a first biomarker, and the unmixed image data in a fourth data channel describes fluorescence signals attributable to a second biomarker;

a cell masker configured to receive image data from the first data channel and generating an image representative of all nuclei in a field of view and dilating the image to generate a cell mask;

a tumor area masker configured to receive image data from the second data channel and generating a mask of all tumor area in the field of view;

a first biomarker masker configured to receive image data from the third data channel and generating a first biomarker mask of all cells in the field of view that express the first biomarker;

a second biomarker masker configured to receive image data from the fourth data channel and generating a second biomarker mask of all cells in the field of view that express the second biomarker;

a tumor masker configured to combine the cell mask and the tumor area mask to generate at least one of a non-tumor cell mask and a tumor cell mask;

a dilator configured to dilate the first biomarker mask to generate a dilated first biomarker mask;

an interaction masker configured to the dilated first biomarker mask and the second biomarker mask to generate an interaction mask;

an interaction calculator configured to calculate a spatial proximity score.

Para. BB. The system of Para. BA in which the interaction calculator is configured to divide the area of the interaction mask by the area of one of the non-tumor cell mask, the tumor cell mask, and the cell mask.

Para. BC. The system of Para. BA in which the spatial proximity score is calculated according to the equation:

$$SPS = \frac{A_I}{A_C} \times 10^4$$

wherein $A_I$ is a total interaction area (area of the interaction mask) and $A_C$ is the total area of the at least one of the non-tumor cell mask, the tumor cell mask, and the cell mask.

Para. BD. A method of processing an image of a tissue sample to determine a score representative of a proximity between at least one pair of cells in the tissue, the method comprising:

receiving image data associated with a tissue sample comprising tumor tissue taken from the cancer patient;

selecting at least one field of view from the sample which is stained with a plurality of fluorescence tags, which selection is biased toward selecting at least one field of view that contains a greater number of cells that express the first biomarker relative to other fields of view;

dilating, for each of the selected fields of view, fluorescence signals attributable to the first biomarker by a margin sufficient to encompass proximally located cells expressing the second biomarker;

dividing a first total area for all cells from each of the selected fields of view, which express the second biomarker and are encompassed within the dilated fluorescence signals attributable to the cells expressing the first biomarker, with a normalization factor, and multiplying the resulting quotient by a predetermined factor to arrive at a spatial proximity score; and recording the score, which score when compared to a threshold value is indicative of a likelihood that the cancer patient will respond positively to immunotherapy.

Para. BE. The system of Para. A, wherein the method provides a superior predictive power compared to a quantitation of expression of the first biomarker or a quantitation of expression of the second biomarker.

Para. BF. The system of Para. BA, wherein the method provides a superior predictive power compared to a quantitation of expression of the first biomarker or a quantitation of expression of the second biomarker.

Para. BG. The method of Para. BD, wherein the method provides a superior predictive power compared to a quantitation of expression of the first specific biomarker or a quantitation of expression of the second specific biomarker.

Para. BH. The method of Para. BG or the system of Para. BE or Para. BF, wherein the predictive power is quantified as a positive predictive value, a negative predictive value, or a combination thereof.

Para. BI. The method or system of Para. BH, wherein the positive predictive value is 65% or greater.

Para. BJ. The method or system of Para. BI, wherein the positive predictive value is 70% or greater.

Para. BK. The method or system of Para. BJ, wherein the positive predictive value is 75% or greater.

Para. BL. The method or system of Para. BH, wherein the negative predictive value is 65% or greater.

Para. BM. The method or system of Para. BL, wherein the negative predictive value is 80% or greater.

Para. BN. A system for determining a value of biomarker positivity in a tumor tissue sample, the system comprising:

a processing circuit comprising a memory, the memory comprising:

a spectral unmixer configured to receive image data from an imaging device, separating the image data into unmixed image data, and providing the data through a plurality of data channels, in which the unmixed image data in a first data channel describes fluorescence signals attributable to a cell nucleus, the unmixed data in a second data channel describes fluorescence signals attributable to a subset tissue of interest, and the unmixed data in a third data channel describes fluorescence signals attributable to a first biomarker;

a cell masker configured to use image data from the first data channel and generate an image representative of all nuclei in a field of view and dilating the image to generate a cell mask;

a subset area masker configured to use image data from the second data channel and generate a mask of all subset tissue area in the field of view;

a first biomarker masker configured to use image data from the third data channel and generate a first biomarker mask of all cells in the field of view that express the first biomarker;

a subset cell masker configured to combine the cell mask and the subset tissue area mask to generate at least one of a non-subset cell mask and a subset cell mask; an combination masker configured to combine the biomarker mask and at least one of the non-subset cell mask and the subset cell mask;

a positivity calculator configured to calculate a biomarker positivity value.

Para. BO. The system of Para. BN in which the calculator is configured to divide an area of the biomarker mask by an area of the at least one of the non-subset cell mask and the subset cell mask to calculate the biomarker positivity value.

Para. BP. The system of Para. BN in which the first biomarker comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4. CD8, FoxP3, CD25, CD16, CD56, CD68, CD163, CD80, and CD86.

Para. BQ. The system of Para. BN in which the second biomarker is different from the first biomarker and comprises a biomarker selected from PD-L. PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. BR. The system of Para. BN in which the subset tissue of interest is tumor tissue, the subset cell is a tumor cell, and the non-subset cell is a non-tumor cell.

Para. BS. A system comprising an image processing unit configured to:
receive image data from an imaging device, the image data describing a sample of tissue taken from a patient; and
determine a biomarker positivity value representative of an amount of cells of a type in the sample expressing a biomarker of interest relative to the total amount of cells of the type in the sample.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least." "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method for determining a score representative of a proximity between at least one pair of cells in a tumor tissue sample, the method comprising:
receiving image data from an imaging device, separating the image data into unmixed image data, and providing the unmixed data through a plurality of data channels;
generating, based on first data channel image data, an image representative of all nuclei in a field of view and dilating the image to generate a cell mask;
generating, based on second data channel image data, a mask of all tumor area in the field of view;
generating, based on third data channel image data, a first biomarker mask of all cells in the field of view that express a first biomarker;
generating, based on fourth data channel image data, a second biomarker mask of all cells in the field of view that express a second biomarker;
combining the cell mask and the tumor area mask to generate at least one of a non-tumor cell mask and a tumor cell mask;
dilating the first biomarker mask to encompass proximally located cells expressing the second biomarker to generate a dilated first biomarker mask;
combining the dilated first biomarker mask and the second biomarker mask to generate an interaction mask; and
calculating a spatial proximity score according to the equation:

$$SPS = \frac{A_I}{A_C} \times 10^4$$

wherein $A_I$ is a total interaction area (area of the interaction mask) and $A_C$ is the total area of the at least one of the non-tumor cell mask, the tumor cell mask, and the cell mask.

2. The method of claim 1, further comprising dividing the area of the interaction mask by the area of one of the non-tumor cell mask, the tumor cell mask, and the cell mask.

3. The method of claim 1, wherein the first data channel image data describes fluorescence signals attributable to a cell nucleus, the second data channel image data describes fluorescence signals attributable to tumor tissue, the third channel image data describes fluorescence signals attributable to the first biomarker, and the fourth data channel image data describes fluorescence signals attributable to the second biomarker.

4. The method of claim 1, wherein a first member of the at least one pair of cells comprises a tumor cell and a second member of the at least one pair of cells comprises a non-tumor cell.

5. The method of claim 1, further comprising generating each mask by assigning a binary value to each pixel of image data from a selected channel.

6. The method of claim 5, wherein assigning the binary value to each pixel of image data uses a threshold function, the threshold function comprising:
assigning a value of 1 to each pixel that has an intensity equal to or greater than a predetermined intensity threshold, and
assigning a value of 0 to each pixel that has an intensity below the predetermined intensity threshold.

7. The method of claim 5, wherein assigning the binary value to each pixel of image data uses a histogram threshold function, the histogram threshold function comprising:
using a sliding scale of pixel intensity to determine an intensity threshold;
assigning a value of 1 to each pixel that has an intensity equal to or greater than the intensity threshold; and
assigning a value of 0 to each pixel that has an intensity below the intensity threshold.

8. The method of claim 7, wherein determining the intensity threshold comprises:
summing an intensity of every pixel into a total intensity;
multiplying a threshold percentage by the total intensity to obtain a cut-off sum;
grouping all pixels by intensity in a histogram; and
summing the pixel intensities from lowest to highest until the cut-off sum is achieved,
wherein the last highest pixel intensity visited in the process is the intensity threshold.

9. The method of claim 1, wherein combining the masks is performed using an "and" operation, the "and" operation multiplying a pixel intensity of a pixel in a first mask by a pixel intensity of the pixel in a second mask; or using an "out" operation, the "out" operation removing a second mask from a first mask.

10. A method for determining a value of biomarker positivity in a tumor tissue sample, the method comprising:
receiving image data from an imaging device, separating the image data into unmixed image data, and providing the unmixed data through a plurality of data channels;
generating, from first data channel image data, an image representative of all nuclei in a field of view and dilating the image to generate a cell mask;
generating, from second data channel image data, a mask of all subset tissue area in the field of view;
generating, from third data channel image data, a first biomarker mask of all cells in the field of view that express a first biomarker;
combining the cell mask and the subset tissue area mask to generate at least one of a non-subset cell mask and a subset cell mask;
combining the biomarker mask and the non-subset cell mask or the subset cell mask to generate a combined mask of non-subset cells or subset cells that are positive for the first biomarker; and
calculating a biomarker positivity value by either (i) dividing an area of the combined mask by an area of the non-subset cell mask or the subset cell mask, or (ii) dividing an area of the first biomarker mask by an area of the cell mask;
wherein at least one of combining the cell mask and the subset tissue area mask and combining the biomarker mask and the non-subset cell mask or the subset cell mask is performed using an "and" operation; wherein the "and" operation comprises multiplying a pixel intensity of a pixel in a first mask by a pixel intensity of the pixel in a second mask; or using an "out" operation; wherein the "out" operation comprises removing a second mask from a first mask.

11. The method of claim 10, wherein the first data channel image data describes fluorescence signals attributable to a cell nucleus, the second data channel image data describes fluorescence signals attributable to a subset tissue of interest, and the third data channel image data describes fluorescence signals attributable to the first biomarker.

12. The method of claim 10, wherein the subset tissue of interest is tumor tissue, the subset cell is a tumor cell, and the non-subset cell is a non-tumor cell.

13. The method of claim 10, wherein generating each mask comprises assigning a binary value to each pixel of image data from a selected channel.

14. The method of claim 13, wherein assigning the binary value to each pixel of image data uses a threshold function, the threshold function comprising:
assigning a value of 1 to each pixel that has an intensity equal to or greater than a predetermined intensity threshold, and
assigning a value of 0 to each pixel that has an intensity below the predetermined intensity threshold.

15. The method of claim 13, wherein assigning the binary value to each pixel uses a histogram threshold function, the histogram threshold function comprising:
using a sliding scale of pixel intensity to determine an intensity threshold;
assigning a value of 1 to each pixel that has an intensity equal to or greater than the intensity threshold; and
assigning a value of 0 to each pixel that has an intensity below the intensity threshold.

16. A method of treating cancer in a patient in need thereof, the method comprising
(a) scoring a sample comprising tumor tissue taken from the patient comprising
(i) determining a score representative of a spatial proximity between at least one pair of cells from the sample comprising tumor tissue taken from the patient, a first member of the at least one pair of cells expressing a first biomarker and a second member of the at least one pair of cells expressing a second biomarker that is different from the first biomarker; and
(ii) recording the score;
(b) comparing the score to a threshold value; and
(c) administering immunotherapy to the patient if the score when compared to the threshold value is indicative of a likelihood that the patient will respond positively to the immunotherapy;
wherein determining the score representative of the spatial proximity between the at least one pair of cells comprises positioning the sample in an imaging field of an imaging device, the sample being stained with a plurality of biomarkers;

radiating the sample with electromagnetic radiation;

receiving, from the imaging device, separating the image data into unmixed image data and providing the unmixed data through a plurality of data channels;

generating, based on first data channel image data, an image representative of all nuclei in a field of view and dilating the image to generate a cell mask;

generating, based on second data channel image data, a mask of all tumor area in the field of view;

generating, based on third data channel image data, a first biomarker mask of all cells in the field of view that express a first biomarker;

generating, based on fourth data channel image data, a second biomarker mask of all cells in the field of view that express a second biomarker;

combining the cell mask and the tumor area mask to generate at least one of a non-tumor cell mask and a tumor cell mask;

dilating the first biomarker mask to encompass proximally located cells expressing the second biomarker to generate a dilated first biomarker mask;

combining the dilated first biomarker mask and the second biomarker mask to generate an interaction mask; and calculating the score (SPS) representative of the spatial proximity between the at least one pair of cells according to the equation:

$$SPS = \frac{A_I}{A_C} \times 10^4$$

wherein $A_I$ is a total interaction area (area of the interaction mask) and $A_C$ is the total area of the at least one of the non-tumor cell mask, the tumor cell mask, and the cell mask.

17. The method of claim 16, wherein the score is determined by obtaining a proximity between centers of mass of the pair of cells or a proximity between plasma membranes of the pair of cells.

18. The method of claim 16, further comprising at least one of:
generating a report including the score;
recording the score in a database;
displaying the score on a display device; and
associating the score with the patient's medical record.

19. The method of claim 16, wherein the first member of the at least one pair of cells expresses a first biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, and combinations thereof, and the second member of the at least one pair of cells expresses a second biomarker selected from the group consisting of PD-1, TIM3, LAG3, 41BB, OX40, CTLA-4, CD40L, CD28, GITR, ICOS, CD28, and combinations thereof.

* * * * *